US005608816A

United States Patent [19]
Kawahara et al.

[11] Patent Number: 5,608,816
[45] Date of Patent: Mar. 4, 1997

[54] APPARATUS FOR INSPECTING A WIRING PATTERN ACCORDING TO A MICRO-INSPECTION AND A MACRO-INSPECTION PERFORMED IN PARALLEL

[75] Inventors: Toyoki Kawahara; Atsuharu Yamamoto, both of Kawasaki; Yuji Maruyama; Hidehiko Kawakami, both of Tokyo; Hideaki Kawamura, Kyoto, all of Japan

[73] Assignee: Matsushita Electric Industrial Co., Ltd., Osaka, Japan

[21] Appl. No.: 305,968

[22] Filed: Sep. 15, 1994

[30] Foreign Application Priority Data

Dec. 24, 1993 [JP] Japan .................................. 5-328500

[51] Int. Cl.⁶ .............................. G06K 9/03; H04N 7/18
[52] U.S. Cl. ......................... 382/149; 382/147; 382/150; 382/257; 348/126
[58] Field of Search .................................. 382/147, 149, 382/150, 145, 151, 257; 348/126

[56] References Cited

U.S. PATENT DOCUMENTS

| 4,630,306 | 12/1986 | West et al. ............................... 382/145 |
| 4,642,813 | 2/1987 | Wilder ..................................... 382/147 |
| 5,185,811 | 2/1993 | Beers et al. .............................. 382/151 |
| 5,185,812 | 2/1993 | Yamashita et al. ..................... 382/145 |
| 5,214,712 | 5/1993 | Yamamoto et al. .................... 382/149 |
| 5,272,763 | 12/1993 | Maruyama et al. .................... 382/147 |
| 5,347,591 | 9/1994 | Onishi et al. ............................ 382/147 |

FOREIGN PATENT DOCUMENTS

| 60-61604 | 4/1985 | Japan .............................. G01B 11/24 |
| 61-15343 | 1/1986 | Japan .............................. H01L 21/66 |
| 62-140009 | 6/1987 | Japan .............................. G01B 11/24 |
| 62-263404 | 11/1987 | Japan .............................. G01B 7/14 |
| 1-180404 | 7/1989 | Japan .............................. G01B 11/24 |
| 3-252545 | 11/1991 | Japan .............................. G01N 21/88 |
| 4-120448 | 4/1992 | Japan .............................. G01N 21/88 |
| 5-60535 | 3/1993 | Japan .............................. G01B 11/24 |
| 6-203141 | 7/1994 | Japan .............................. G06F 15/62 |

OTHER PUBLICATIONS

"A Visual Inspecting Technique Of Electronic Circuit Boards", O plus E, No. 132, Y, Nakagawa et al., No. 132, pp. 138–152, Nov. 1990.
"Digital Image Processing", Kindaikagaku Co, Ltd., 1992, A. Rosefeld et al.
"Further Consideration On Line Thinning Schemes", H. Tamura, Technical Report, Institute of Electronic Information and Communication Engineers of Japan, PRL75–66, 1975.
"On The Encoding Of Arbitrary Geometric Configurations", IRE Trans. Electron. Comput. EC–10, pp. 260–268, 1961.
"An Algorism Of Pattern Recognition And Learning", published by Bunichisougosyuppan, pp. 91–108, 1990.

Primary Examiner—Leo Boudreau
Assistant Examiner—Monica S. Davis
Attorney, Agent, or Firm—Lowe, Price, LeBlanc & Becker

[57] ABSTRACT

Pieces of feature information in a bi-level image such as a width, a branching point and an ending point of a wiring pattern are detected in a design rule checking section according to a micro inspection to find out pieces of feature information departing from a design rule. Also, feature codes in the bi-level image such as a corner of the wiring pattern are detected in a specific shape detecting section according to a macro inspection. The feature information are compared with pieces of referential feature information pertaining to a non-defective wiring pattern in a first comparing and judging section to judge whether the wiring pattern indicated by the feature information is defective or non-defective. The feature codes are compared with referential feature codes pertaining to a non-defective wiring pattern in a second comparing and judging section to judge whether the wiring pattern indicated by the feature codes is defective or non-defective. Therefore, defective types and portions of the wiring pattern can be detected by performing the macro inspection and the micro inspection in parallel without dividing the wiring pattern into processed regions.

24 Claims, 42 Drawing Sheets

FIG. 5A

|   |   |   | 5 | 5 | 5 | 5 | 5 |   |   |
|---|---|---|---|---|---|---|---|---|---|
|   |   | 5 | 4 | 4 | 4 | 4 | 4 | 5 |   |
|   | 5 | 4 | 4 | 3 | 3 | 3 | 4 | 4 | 5 |
| 5 | 4 | 4 | 3 | 2 | 2 | 2 | 3 | 4 | 4 | 5 |
| 5 | 4 | 3 | 2 | 1 | 1 | 1 | 2 | 3 | 4 | 5 |
| 5 | 4 | 3 | 2 | 1 | 0 | 1 | 2 | 3 | 4 | 5 |
| 5 | 4 | 3 | 2 | 1 | 1 | 1 | 2 | 3 | 4 | 5 |
| 5 | 4 | 4 | 3 | 2 | 2 | 2 | 3 | 4 | 4 | 5 |
|   | 5 | 4 | 4 | 3 | 3 | 3 | 4 | 4 | 5 |   |
|   |   | 5 | 4 | 4 | 4 | 4 | 4 | 5 |   |   |
|   |   |   | 5 | 5 | 5 | 5 | 5 |   |   |   |

FIG. 5B

| 5 | 5 | 5 | 5 | 5 | 5 | 5 | 5 | 5 | 5 |
|---|---|---|---|---|---|---|---|---|---|
| 5 | 4 | 4 | 4 | 4 | 4 | 4 | 4 | 4 | 5 |
| 5 | 4 | 3 | 3 | 3 | 3 | 3 | 3 | 4 | 5 |
| 5 | 4 | 3 | 2 | 2 | 2 | 2 | 2 | 3 | 4 | 5 |
| 5 | 4 | 3 | 2 | 1 | 1 | 1 | 2 | 3 | 4 | 5 |
| 5 | 4 | 3 | 2 | 1 | 0 | 1 | 2 | 3 | 4 | 5 |
| 5 | 4 | 3 | 2 | 1 | 1 | 1 | 2 | 3 | 4 | 5 |
| 5 | 4 | 3 | 2 | 2 | 2 | 2 | 2 | 3 | 4 | 5 |
| 5 | 4 | 3 | 3 | 3 | 3 | 3 | 3 | 4 | 5 |
| 5 | 4 | 4 | 4 | 4 | 4 | 4 | 4 | 4 | 5 |
| 5 | 5 | 5 | 5 | 5 | 5 | 5 | 5 | 5 | 5 |

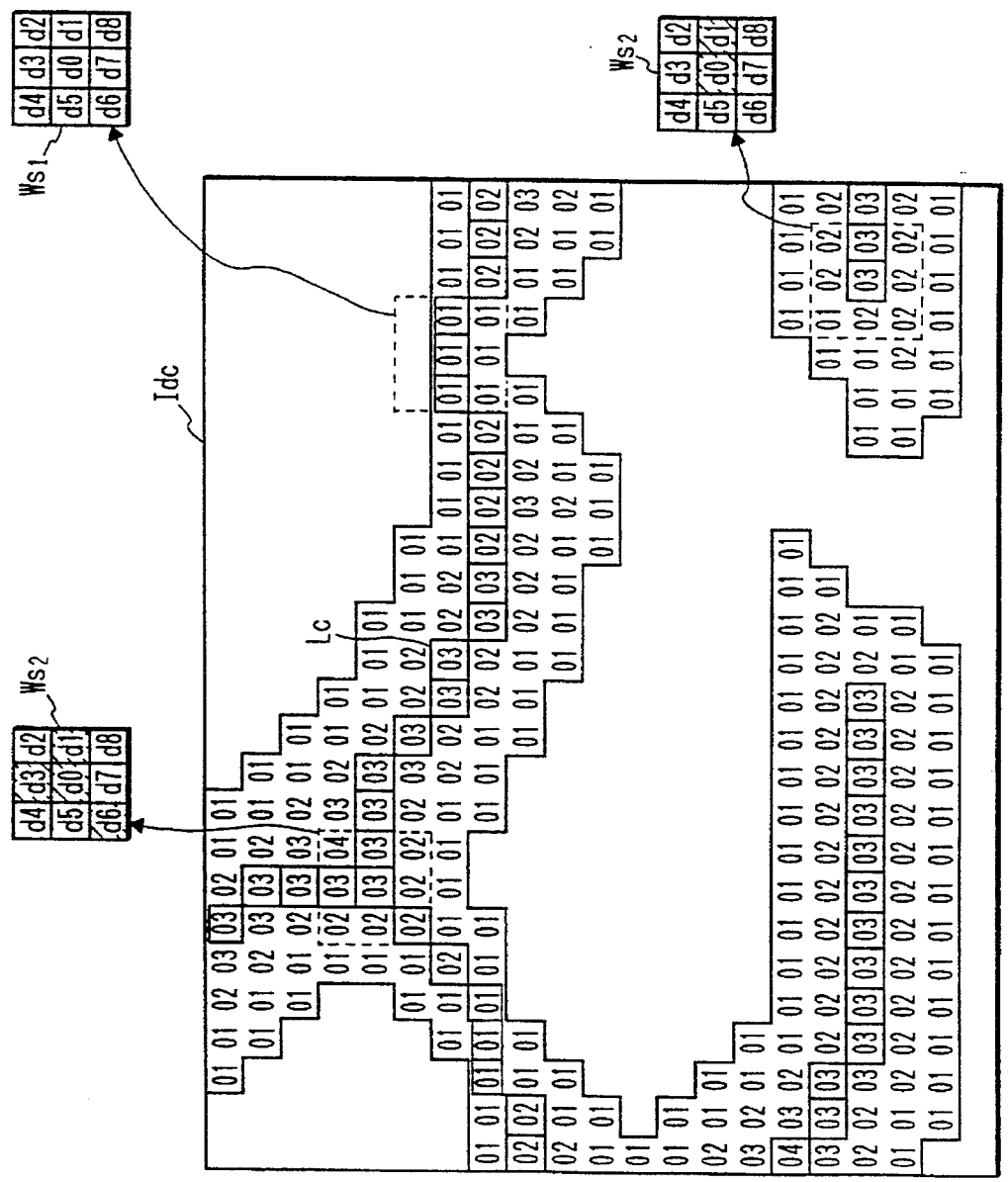

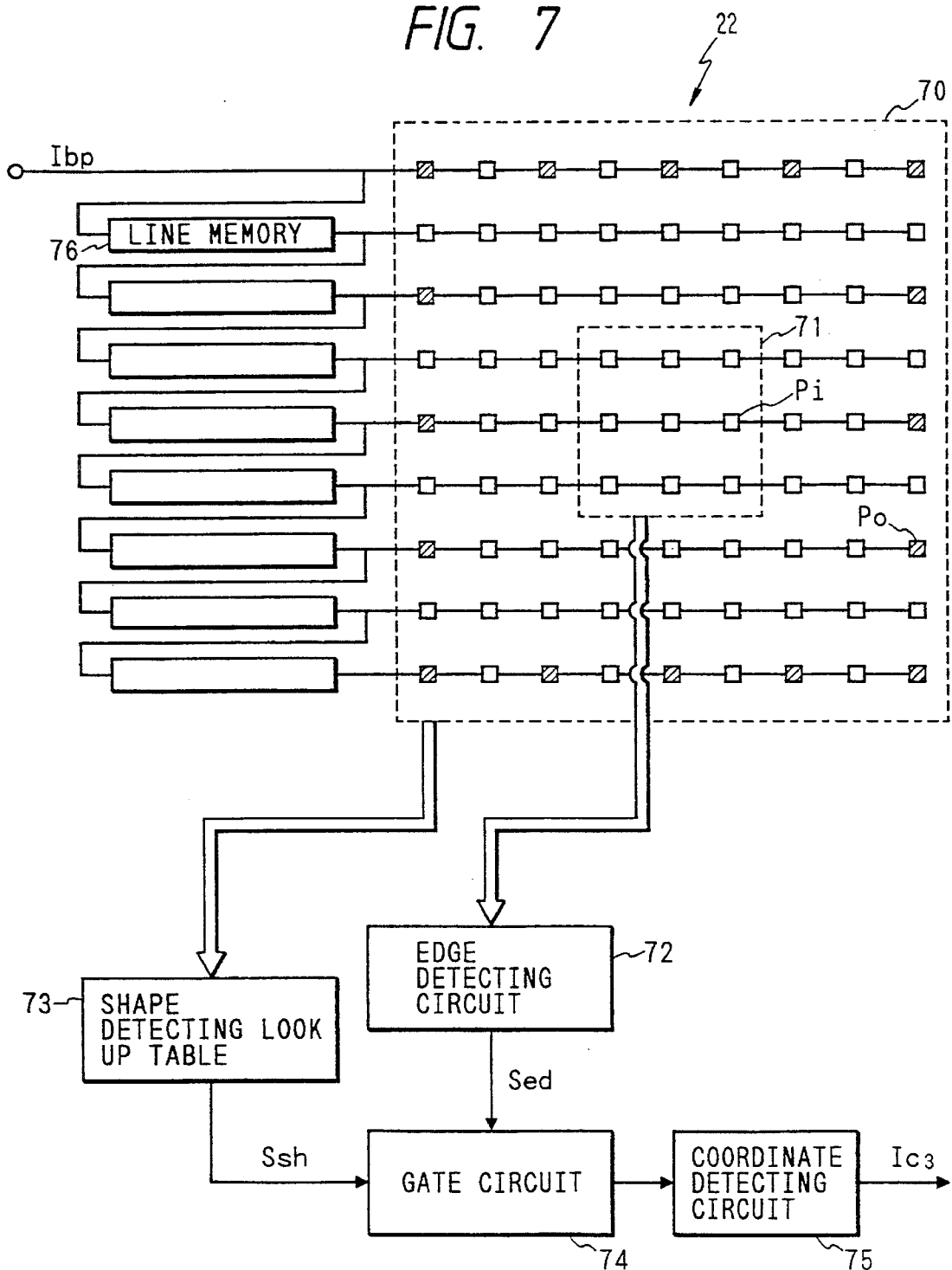

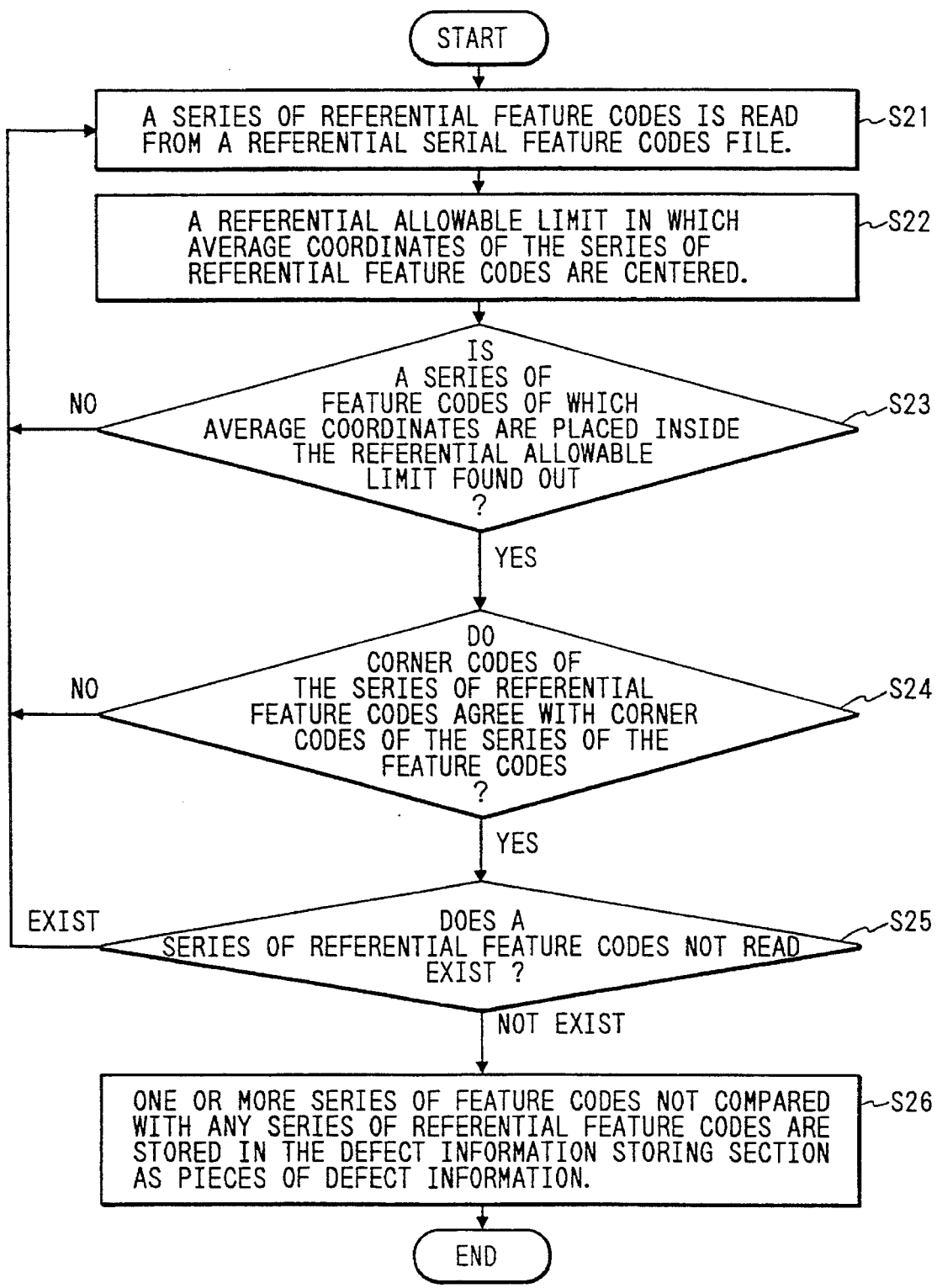

FIG. 18

| NO. | INSPEC-TION CODES | VERIFI-CATION CODES | THE NUMBER OF THE SERIES OF FEATURE CODES CORRESPONDING TO THE SERIES OF REFERENTIAL FEATURE CODES | THE SERIES OF REFERENTIAL FEATURE CODES | AVERAGE ADDRESSES (x, y) |
|---|---|---|---|---|---|
| 0001 | 1 | 1 | 0001 | $I_{18}$-$I_{81}$-$I_{12}$-$I_{21}$ | (256, 202) |
| 0002 | 1 | 1 | 0003 | $I_{56}$-$I_{67}$-$I_{78}$-$I_{87}$ | (747, 292) |
| 0003 | 1 | 1 | 0002 | $I_{23}$-$I_{32}$ | (1038, 354) |
| 0004 | 1 | 0 | 0006 | $I_{76}$ | (794, 390) |
| 0005 | 1 | 1 | 0005 | $I_{21}$-$I_{12}$-$I_{23}$-$I_{34}$-$I_{43}$ | (296, 446) |
| 0006 | 0 | 0 |  | $I_{12}$-$I_{21}$ | (344, 679) |
| ⋮ | ⋮ | ⋮ | ⋮ | ⋮ | ⋮ |
| 0789 | 1 | 1 | 0782 | $I_{87}$-$I_{78}$-$I_{81}$-$I_{12}$-$I_{21}$-$I_{18}$ | (1529, 604) |

FIG. 19

| NO. | INSPEC-TION CODES | VERIFI-CATION CODES | THE SERIES OF FEATURE CODES | AVERAGE ADDRESSES (x, y) |
|---|---|---|---|---|
| 0001 | 1 | 1 | $I_{18}$-$I_{81}$-$I_{12}$-$I_{21}$ | (250, 226) |
| 0002 | 1 | 1 | $I_{23}$-$I_{32}$ | (1025, 325) |
| 0003 | 1 | 1 | $I_{56}$-$I_{67}$-$I_{78}$-$I_{87}$ | (752, 312) |
| 0004 |  |  | $I_{65}$-$I_{56}$ | (304, 775) |
| 0005 | 1 | 1 | $I_{21}$-$I_{12}$-$I_{23}$-$I_{34}$-$I_{43}$ | (297, 456) |
| 0006 | 1 | 0 | $I_{76}$-$I_{67}$-$I_{76}$ | (798, 376) |
| ⋮ | ⋮ | ⋮ | ⋮ | ⋮ |
| 0782 | 1 | 1 | $I_{87}$-$I_{78}$-$I_{81}$-$I_{12}$-$I_{21}$-$I_{18}$ | (1521, 1614) |

FIG. 22

| INSPECTED CODES SERIES A : $I_{18}$-$I_{81}$-$I_{18}$-$I_{87}$ |
|---|
| REFERENTIAL CODES SERIES B : $I_{18}$-$I_{87}$ |

FIG. 23

| i | j | G(i, j) | THE CORRESPONDENCE OF CHARACTERISTIC CODES TO REFERENTIAL FEATURE CODES | SURPLUS CODES SERIES |
|---|---|---|---|---|
| 1 | 1 | $S(I_{18}, I_{18})$ | $I_{18}$<br>$I_{18}$ | |
| 1 | 2 | $S(I_{18}, I_{18})+S(*, I_{87})$ | $I_{18}$-*<br>$I_{18}$-$I_{87}$ | $I_{87}$ |
| 2 | 1 | $S(I_{18}, I_{18})+S(I_{81}, *)$ | $I_{18}$-$I_{81}$<br>$I_{18}$-* | $I_{81}$ |
| 2 | 2 | $S(I_{18}, I_{18})+S(I_{81}, *)+S(*, I_{87})$ | $I_{18}$-$I_{81}$-*<br>$I_{18}$-*-$I_{87}$ | $I_{81}$<br>$I_{87}$ |
| 3 | 1 | $S(I_{18}, I_{18})+S(I_{81}, *)+S(I_{18}, *)$ | $I_{18}$-$I_{81}$-$I_{18}$<br>$I_{18}$-*-* | $I_{81}$-$I_{18}$ |
| 3 | 2 | $S(I_{18}, I_{18})+S(I_{81}, *)+S(I_{18}, *)+S(*, I_{87})$ | $I_{18}$-$I_{81}$-$I_{18}$-*<br>$I_{18}$-*-*-$I_{87}$ | $I_{81}$-$I_{18}$<br>$I_{87}$ |
| 4 | 1 | $S(I_{18}, I_{18})+S(I_{81}, *)+S(I_{18}, *)+S(I_{87}, *)$ | $I_{18}$-$I_{81}$-$I_{18}$-$I_{87}$<br>$I_{18}$-*-*-* | $I_{81}$-$I_{18}$-$I_{87}$ |
| 4 | 2 | $S(I_{18}, I_{18})+S(I_{81}, *)+S(I_{18}, *)+S(I_{87}, I_{87})$ | $I_{18}$-$I_{81}$-$I_{18}$-$I_{87}$<br>$I_{18}$-*-*-$I_{87}$ | $I_{81}$-$I_{18}$ |

FIG. 24A
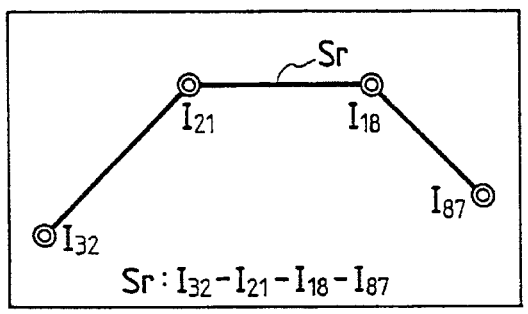
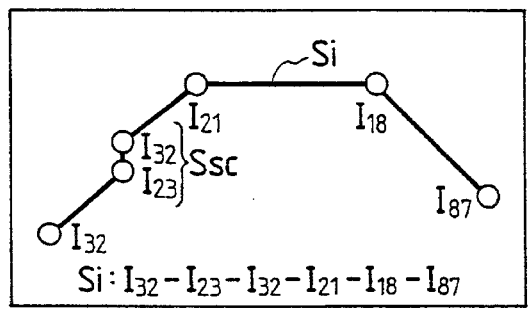
Sr: $I_{32}-I_{21}-I_{18}-I_{87}$
Si: $I_{32}-I_{23}-I_{32}-I_{21}-I_{18}-I_{87}$
FIG. 24B
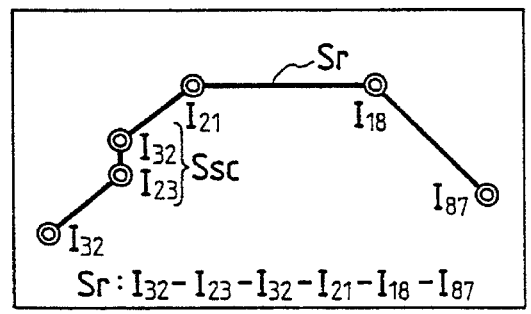
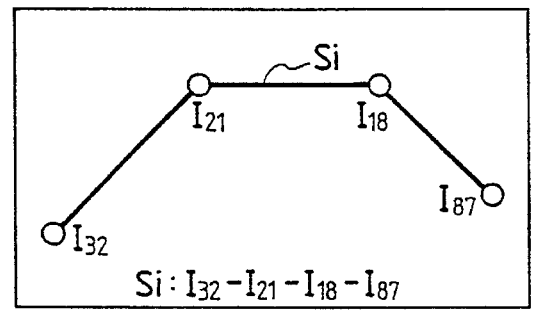
Sr: $I_{32}-I_{23}-I_{32}-I_{21}-I_{18}-I_{87}$
Si: $I_{32}-I_{21}-I_{18}-I_{87}$

SURPLUS CODE SERIES : $I_{12}-I_{21}$

SURPLUS CODE SERIES : $I_{12}-I_{21}$

FIG. 27

| NO. | PROCESS-ED "1" | VERIFI-CATION CODES | NO. OF CORRESPONDING REFERENTIAL FEATURE CODES SERIES | INSPECTED FEATURE CODE SERIES | SURPLUS CODES SERIES | AVERAGE ADDRESSES (x, y) |
|---|---|---|---|---|---|---|
| 0001 | 1 | 1 | 0001 | $I_{18}-I_{81}-I_{12}-I_{21}$ | NOT EXIST | (256, 202) |
| 0002 | 1 | 1 | 0003 | $I_{56}-I_{67}-I_{78}-I_{87}$ | NOT EXIST | (747, 292) |
| 0003 | 1 | 1 | 0002 | $I_{23}-I_{32}$ | NOT EXIST | (1038, 354) |
| 0004 | 1 | 0 | | $I_{87}-I_{76}$ | $I_{65}-I_{54}-I_{43}-I_{32}$ | (794, 390) |
| 0005 | 1 | 1 | 0005 | $I_{21}-I_{12}-I_{23}-I_{34}-I_{43}$ | NOT EXIST | (296, 446) |
| 0006 | 1 | 1 | 0004 | $I_{78}-I_{81}-I_{12}-I_{21}$ | NOT EXIST | (344, 679) |
| 0789 | 1 | 1 | 0782 | $I_{87}-I_{78}-I_{81}-I_{12}-I_{21}-I_{18}$ | NOT EXIST | (1529, 604) |

FIG. 28

| NO. | PROCESSED "1" | VERIFICATION CODES | REFERENTIAL FEATURE CODE SERIES | SURPLUS CODES SERIES | AVERAGE ADDRESSES |
|---|---|---|---|---|---|
| 0001 | 1 | 1 | $I_{18}-I_{81}-I_{12}-I_{21}$ | NOT EXIST | (250, 226) |
| 0002 | 1 | 1 | $I_{23}-I_{32}$ | NOT EXIST | (1025, 325) |
| 0003 | 1 | 1 | $I_{56}-I_{67}-I_{78}-I_{87}$ | NOT EXIST | (752, 312) |
| 0004 | 1 | 1 | $I_{78}-I_{81}$ | $I_{12}-I_{21}$ | (348, 680) |
| 0005 | 1 | 1 | $I_{21}-I_{12}-I_{23}-I_{34}-I_{43}$ | NOT EXIST | (297, 456) |
| 0006 | 1 | 0 | $I_{87}-I_{76}-I_{65}-I_{54}-I_{45}-I_{32}$ | NOT EXIST | (798, 376) |
| ... | ... | ... | ... | ... | ... |
| 0782 | 1 | 1 | $I_{87}-I_{78}-I_{81}-I_{12}-I_{21}-I_{18}$ | NOT EXIST | (1521, 1614) |

FIG. 30C OPEN-END $I_{18}-I_{87}-I_{76}-I_{65}, I_{54}-I_{43}-I_{32}-I_{21}$

FIG. 30D PROTRUSION $I_{12}-I_{21}-I_{18}-I_{81}$

FIG. 30F

PINHOLE $I_{45}-I_{56}-I_{67}-I_{78}-I_{81}-I_{12}-I_{23}-I_{34}$

FIG. 30E

RESIDUE $I_{18}-I_{87}-I_{76}-I_{65}-I_{54}-I_{43}-I_{32}-I_{21}$

FIG. 31A

| IDENTIFICATION CODES | A1 | A2 | A3 | A4 |
|---|---|---|---|---|
| FUNDAMENTAL CODES SERIES | $I_{12}-I_{23}-I_{34}-I_{45}$ | $I_{23}-I_{34}-I_{45}-I_{56}$ | $I_{34}-I_{45}-I_{56}-I_{67}$ | $I_{45}-I_{56}-I_{67}-I_{78}$ |

| IDENTIFICATION CODES | A5 | A6 | A7 | A8 |
|---|---|---|---|---|
| FUNDAMENTAL CODES SERIES | $I_{56}-I_{67}-I_{78}-I_{81}$ | $I_{67}-I_{78}-I_{81}-I_{12}$ | $I_{78}-I_{81}-I_{12}-I_{23}$ | $I_{81}-I_{12}-I_{23}-I_{34}$ |

SHORT

FIG. 31B

| IDENTIFICATION CODES | B1 | B2 | B3 | B4 |
|---|---|---|---|---|
| FUNDAMENTAL CODE SERIES | $I_{18}-I_{87}-I_{76}-I_{65}$ | $I_{21}-I_{18}-I_{87}-I_{76}$ | $I_{32}-I_{21}-I_{18}-I_{87}$ | $I_{43}-I_{32}-I_{21}-I_{18}$ |

| IDENTIFICATION CODES | B5 | B6 | B7 | B8 |
|---|---|---|---|---|
| FUNDAMENTAL CODE SERIES | $I_{54}-I_{43}-I_{32}-I_{21}$ | $I_{65}-I_{54}-I_{43}-I_{32}$ | $I_{76}-I_{65}-I_{54}-I_{43}$ | $I_{87}-I_{76}-I_{65}-I_{54}$ |

OPEN-END

FIG. 31C

DISCONNECTION

| IDENTIFICATION CODES | C1 | C2 | C3 | C4 |
|---|---|---|---|---|
| FUNDAMENTAL CODE SERIES | $I_{18}-I_{81}-I_{12}-I_{21}$ | $I_{21}-I_{12}-I_{23}-I_{32}$ | $I_{32}-I_{23}-I_{34}-I_{43}$ | $I_{43}-I_{34}-I_{45}-I_{54}$ |

| IDENTIFICATION CODES | C5 | C6 | C7 | C8 |
|---|---|---|---|---|
| FUNDAMENTAL CODE SERIES | $I_{54}-I_{45}-I_{56}-I_{65}$ | $I_{65}-I_{56}-I_{67}-I_{76}$ | $I_{76}-I_{67}-I_{78}-I_{87}$ | $I_{81}-I_{78}-I_{81}-I_{18}$ |

FIG. 31D

PROTRUSION

| IDENTIFICATION CODES | D1 | D2 | D3 | D4 |
|---|---|---|---|---|
| FUNDAMENTAL CODES SERIES | $I_{12}-I_{21}-I_{18}-I_{81}$ | $I_{23}-I_{32}-I_{21}-I_{12}$ | $I_{34}-I_{43}-I_{32}-I_{23}$ | $I_{45}-I_{54}-I_{43}-I_{34}$ |

| IDENTIFICATION CODES | D5 | D6 | D7 | D8 |
|---|---|---|---|---|
| FUNDAMENTAL CODES SERIES | $I_{56}-I_{65}-I_{54}-I_{45}$ | $I_{67}-I_{76}-I_{65}-I_{56}$ | $I_{78}-I_{87}-I_{76}-I_{67}$ | $I_{81}-I_{18}-I_{87}-I_{78}$ |

FIG. 31E

RESIDUE

| IDENTIFICATION CODE | E1 |
|---|---|
| FUNDAMENTAL CODES SERIES | $I_{18}-I_{87}-I_{76}-I_{65}-I_{54}-I_{43}-I_{32}-I_{21}$ |

FIG. 31F

PINHOLE

| IDENTIFICATION CODE | F1 |
|---|---|
| FUNDAMENTAL CODES SERIES | $I_{45}-I_{56}-I_{67}-I_{78}-I_{81}-I_{12}-I_{23}-I_{34}$ |

FIG. 47A

|   | 3 |   |
|---|---|---|
|   | 3 |   |
| 2 |   |   |

FIG. 47B

|   | 2 |   |
|---|---|---|
|   | 3 |   |
| 2 |   |   |

FIG. 47C

|   | 7 |   |
|---|---|---|
|   |   | 6 |
| 7 |   |   |

FIG. 47D

|   | 3 |   |
|---|---|---|
|   | 3 |   |
| 2 |   |   |

FIG. 47E

|   | 2 |   |
|---|---|---|
|   | 2 |   |
| 2 |   |   |

FIG. 47F

|   | 7 |   |
|---|---|---|
|   |   | 7 |
| 7 |   |   |

FIG. 33

| NO. | AVERAGE ADDRESSES (x, y) | VERIFICATION CODES OR IDENTIFICATION CODES | THE NUMBER OF THE CORRESPONDING INSPECTED FEATURE CODE SERIES | DEFECT SHAPE TYPES | THE REFERENTIAL FEATURE CODE SERIES |
|---|---|---|---|---|---|
| 2419 | (1497, 2825) | A1 | 2420 | SHORT | $I_{12}-I_{23}-I_{34}-I_{45}$ |
| 2420 | (1531, 2824) | A5 | 2419 | SHORT | $I_{56}-I_{67}-I_{78}-I_{81}$ |
| 2793 | (1617, 3106) | C7 |  | DISCONNECTION | $I_{76}-I_{65}-I_{56}-I_{67}-I_{76}-I_{65}-I_{67}-I_{78}-I_{87}-I_{78}-I_{87}-I_{78}-I_{87}$ |
| 2977 | (1632, 5779) | 00 |  | (DELETED) | $I_{34}-I_{43}$ |
| 3205 | (1758, 3208) | 00 |  | (DELETED) | $I_{45}-I_{67}-I_{78}-I_{87}-I_{76}-I_{65}-I_{54}-I_{45}-I_{54}-I_{45}-I_{54}$ |
| 4308 | (2057, 2921) | B1 | 4309 | OPEN-END | $I_{81}-I_{18}-I_{87}-I_{76}-I_{65}-I_{54}$ |
| 4309 | (2079, 2923) | B5 | 4308 | OPEN-END | $I_{45}-I_{54}-I_{43}-I_{32}-I_{21}-I_{18}$ |
| 4664 | (2302, 4468) | 00 |  | (DELETED) | $I_{54}-I_{45}$ |
| 5156 | (2507, 2376) | 00 |  | (DELETED) | $I_{45}-I_{54}-I_{45}-I_{54}-I_{45}-I_{54}$ |
| 6131 | (2842, 4083) | C1 |  | DISCONNECTION | $I_{18}-I_{81}-I_{18}-I_{81}-I_{18}-I_{81}-I_{12}-I_{21}-I_{12}-I_{21}-I_{12}-I_{21}$ |
| 6400 | (2951, 4342) | A1 | 6401 | SHORT | $I_{12}-I_{23}-I_{34}-I_{45}$ |
| 6401 | (3039, 4342) | A5 | 6400 | SHORT | $I_{56}-I_{67}-I_{78}-I_{81}$ |
| 6648 | (3079, 3916) | B1 | 6649 | OPEN-END | $I_{18}-I_{87}-I_{76}-I_{65}$ |
| 6649 | (3118, 3917) | B5 | 6648 | OPEN-END | $I_{54}-I_{43}-I_{32}-I_{21}$ |
| 6991 | (3305, 4209) | E1 |  | RESIDUE | $I_{18}-I_{87}-I_{76}-I_{65}-I_{54}-I_{43}-I_{32}-I_{21}$ |
| 7696 | (3563, 3774) | F1 |  | PINHOLE | $I_{45}-I_{56}-I_{67}-I_{78}-I_{81}-I_{12}-I_{23}-I_{34}$ |

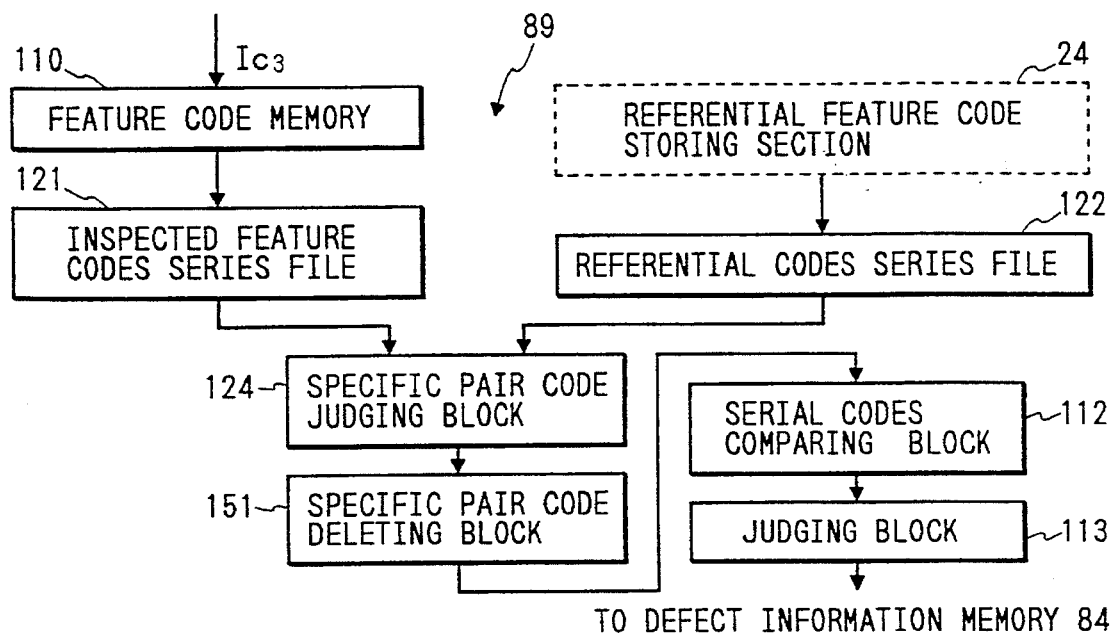
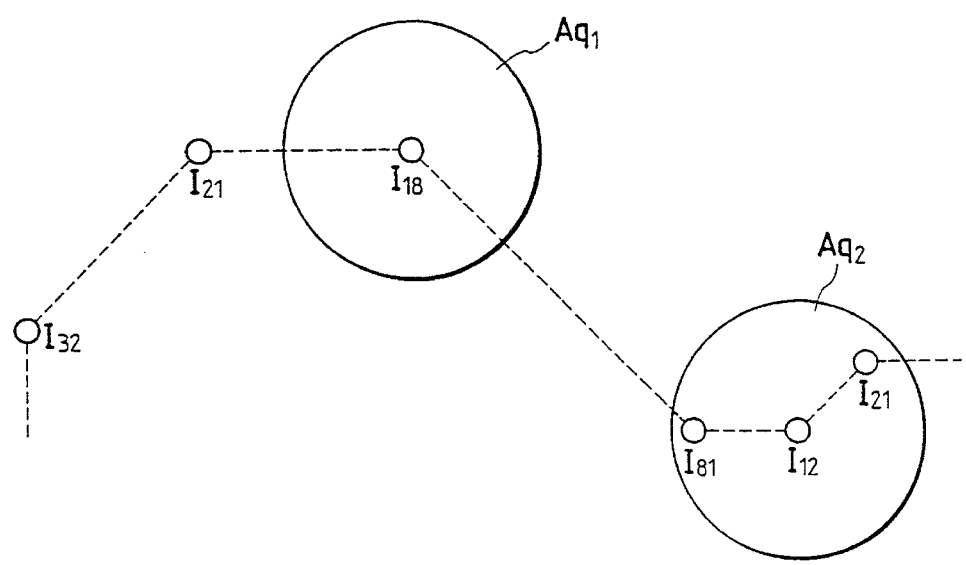

FIG. 44

| COMPARATORS | | | | | | | | L.S.B. OF DCO | Vs | OUTPUT OF MULTI-PLEXER |
|---|---|---|---|---|---|---|---|---|---|---|
| 166 | 167 | 168 | 169 | 170 | 171 | 172 | 173 | | | |
| - | - | - | - | - | - | - | - | 0 | 0 | DC 0 |
| 0 | 0 | 0 | 0 | 0 | 0 | 0 | 0 | 1 | 0 | DC 0 |
| 1 | 0 | 0 | 0 | 0 | 0 | 0 | 0 | 1 | 3 | DC 3 |
| 0 | 1 | 0 | 0 | 0 | 0 | 0 | 0 | 1 | 2 | DC 2 |
| 0 | 0 | 1 | 0 | 0 | 0 | 0 | 0 | 1 | 8 | DC 8 |
| 0 | 0 | 0 | 1 | 0 | 0 | 0 | 0 | 1 | 1 | DC 1 |
| 0 | 0 | 0 | 0 | 1 | 0 | 0 | 0 | 1 | 6 | DC 6 |
| 0 | 0 | 0 | 0 | 0 | 1 | 0 | 0 | 1 | 7 | DC 7 |
| 0 | 0 | 0 | 0 | 0 | 0 | 1 | 0 | 1 | 4 | DC 4 |
| 0 | 0 | 0 | 0 | 0 | 0 | 0 | 1 | 1 | 5 | DC 5 |

FIG. 45

| COMPARATORS | | | | | | | | L.S.B. OF DCO | Vs | OUTPUT OF MULTI-PLEXER |
|---|---|---|---|---|---|---|---|---|---|---|
| 166 | 167 | 168 | 169 | 170 | 171 | 172 | 173 | | | |
| - | - | - | - | - | - | - | - | 1 | 0 | DC 0 |
| 0 | 0 | 0 | 0 | 0 | 0 | 0 | 0 | 0 | 0 | DC 0 |
| 1 | 0 | 0 | 0 | 0 | 0 | 0 | 0 | 0 | 3 | DC 3 |
| 0 | 1 | 0 | 0 | 0 | 0 | 0 | 0 | 0 | 2 | DC 2 |
| 0 | 0 | 1 | 0 | 0 | 0 | 0 | 0 | 0 | 8 | DC 8 |
| 0 | 0 | 0 | 1 | 0 | 0 | 0 | 0 | 0 | 1 | DC 1 |
| 0 | 0 | 0 | 0 | 1 | 0 | 0 | 0 | 0 | 6 | DC 6 |
| 0 | 0 | 0 | 0 | 0 | 1 | 0 | 0 | 0 | 7 | DC 7 |
| 0 | 0 | 0 | 0 | 0 | 0 | 1 | 0 | 0 | 4 | DC 4 |
| 0 | 0 | 0 | 0 | 0 | 0 | 0 | 1 | 0 | 5 | DC 5 |

FIG. 46

APPARATUS FOR INSPECTING A WIRING PATTERN ACCORDING TO A MICRO-INSPECTION AND A MACRO-INSPECTION PERFORMED IN PARALLEL

BACKGROUND OF THE INVENTION

1. Field of the Invention

The present invention relates to a wiring pattern inspection apparatus in which a defective in a wiring pattern formed on a printed wiring board, a photomask or the like is inspected.

2. Description of the Prior Art

The inspection to find out a defective in a printed wiring board has conventionally relied on a visual inspection performed by a human. However, as products are miniaturized and lightened, a wiring pattern formed on the printed wiring board is miniaturized and complicated more and more. Therefore, it is difficult to inspect the miniaturized wiring pattern with a high inspecting precision. Also, it is difficult to inspect the miniaturized wiring pattern for a long time. As a result, the automatization of the inspection has been strongly required.

As a conventional example of a visual inspection apparatus for inspecting a printed wiring board, various types of inspection apparatuses are proposed in a literature (Y. Nakagawa, and T. Ninomiya: "A Visual Inspecting Technique of Electronic Circuit Boards", O plus E, No.132, pp.138–152 (November 1990)). Pattern inspecting method are roughly classified into a characteristic extracting method (or a design rule checking method) and a comparison inspecting method. In the design rule checking method, it is Judged whether or not a wiring pattern departs from a design rule by inspecting characteristics of a line width and the wiring pattern such as a connecting point, an ending point and the like. For example, the design rule checking method has been proposed in the Japanese Published Unexamined Patent Application No. 15343 of 1986 and in the Japanese Published Unexamined Patent Application No. 263404 of 1987.

Also, in the comparison inspecting method, an inspected pattern displayed in an image plane is compared with a reference pattern of a good product or a design pattern for each of pixels. For example, the comparison inspecting method has been proposed in the Japanese Published Unexamined Patent Application No. 61604 of 1985 and in the Japanese Published Unexamined Patent Application No. 140009 of 1987.

3. Problems to be solved by the Invention

However, each of the above methods has both merits and demerits, so that various methods have been proposed to compensate the above methods for the demerits. For example, in the literature (Y. Nakagawa, and T. Ninomiya: "A Visual Inspecting Technique of Electronic Circuit Boards", O plus E, No.132, pp.138–152 (November 1990)), the characteristic extracting method and the comparison inspecting method are combined to adopt the merits of the characteristic extracting method and the comparison inspecting method for the purpose of compensating for the demerits. Also, a hopeful method has been proposed in the Japanese Published Unexamined Patent Application No. 180404 of 1989. In this application, a plurality of inspecting methods are prepared in advance to apply one of the inspecting methods for each of pattern regions to be inspected, and a group of pattern regions which are inspected according to a prescribed inspecting method is determined. This determination is performed for each of the inspecting methods. To be concrete, either the characteristic extracting method or the comparison inspecting method is selected for each of the pattern regions.

However, because a wiring pattern is miniaturized and complicated in recent years, there is a drawback that it is difficult to manually set one of the inspecting methods for each of a plurality of pattern regions in the range of several tens to several hundreds in number. Also, there is another drawback that a position of a wiring region for which one of the inspecting methods is set does not accord with that of a printed wiring board to be inspected.

SUMMARY OF THE INVENTION

An object of the present invention is to provide, with due consideration to the drawbacks of such a conventional wiring pattern inspection apparatus, a wiring pattern inspection apparatus in which various types of defects existing in a printed wiring board are easily found out without any oversight at a high reliability to perform in parallel both a micro-inspection and a macro-inspection suitable for each of wiring patterns formed on the printed wiring board.

The object is achieved by the provision of a wiring pattern inspection apparatus comprising:

image producing means for producing a gray level image of a printed wiring board on which a holed wiring pattern including a pad seat and a through hole placed in the pad seat are formed;

bi-level image producing means for converting the gray level image produced in the image producing means into a bi-level image in which the holed wiring pattern including the pad seat is expressed by a group of black pixels and the through hole is expressed by a group of white pixels;

narrow width area detecting means for detecting a narrow width area of the pad seat in which a seat remaining width of the pad seat narrowed by the through hole in the bi-level image produced in the bi-level image producing means is lower than a reference width;

through hole filling means for virtually filling the through hole of the bi-level image produced in the bi-level image producing means by changing the group of white pixels expressing the through hole in the bi-level image to a group of black pixels to form a filled through hole, a processed bi-level image in which a wiring pattern composed of the holed wiring pattern and the filled through hole is expressed by a group of black pixels being formed;

design rule detecting means for detecting one or more feature types and those particular positions in the wiring pattern of the processed bi-level image formed in the through hole filling means as pieces of feature information, one or more defective feature types which break one or more design rules of the wiring pattern or denote one or more open-ends or branches of the wiring pattern being included in the feature types;

specific shape detecting means for detecting one or more specific shapes and those particular positions in the wiring pattern of the processed bi-level image formed in the through hole filling means as pieces of feature codes, one or more defective shapes of the wiring pattern being included in the specific shapes;

referential feature information storing means for storing one or more referential feature types and those referential positions in a non-defective printed wiring board of which a non-defective wiring pattern is formed according to the design rules as pieces of referential feature information;

referential feature code storing means for storing one or more referential shapes and those referential positions in a non-defective printed wiring board of which a non-defective wiring pattern is formed according to a desired design as one or more referential feature codes;

first comparing and judging means for comparing the feature information detected in the design rule detecting means with the referential feature information stored in the referential feature information storing means and judging the narrow width area detected in the narrow width area detecting means and one or more pieces of feature information pertaining to the defective feature types which differ from the referential feature information as one or more pieces of defect information; and second comparing and judging means for comparing the feature codes detected in the specific shape detecting means with the referential feature codes stored in the referential feature code storing means and judging one or more feature codes pertaining to the defective shapes which differ from the referential feature codes as one or more defects.

In the above configuration, a gray level image of a printed wiring board is produced in the image producing means. On the printed wiring board, a holed wiring pattern including a pad seat and a through hole placed in the pad seat are formed. Thereafter, in the bi-level image producing means, the gray level image is converted into a bi-level image in which the holed wiring pattern including the pad seat is expressed by a group of black pixels and the through hole is expressed by a group of white pixels. In the bi-level image, a seat remaining width of the pad seat is narrowed by the through hole and is sometimes lower than a reference width. Therefore, a narrow width area of the pad seat in which a seat remaining width of the pad seat is lower than the reference width is detected in the narrow width area detecting means because the narrow width area is equivalent to a defect position. Thereafter, the through hole of the bi-level image is virtually filled in the through hole filling means by changing the group of white pixels expressing the through hole in the bi-level image to a group of black pixels to form a filled through hole. Therefore, a processed bi-level image in which a wiring pattern composed of the holed wiring pattern and the filled through hole is expressed by a group of black pixels is formed.

Thereafter, a micro-inspection is performed in the design rule detecting means and the first comparing and judging means. In detail, one or more feature types and those particular positions in the wiring pattern of the processed bi-level image are detected as pieces of feature information in the design rule detecting means. In this case, one or more defective feature types which break one or more design rules of the wiring pattern or denote one or more open-ends or branches of the wiring pattern are included in the feature types. The feature information are compared with pieces of referential feature information in the first comparing and judging means. The referential feature information are stored in the referential feature information storing means and denote one or more referential feature types and those referential positions in a non-defective printed wiring board formed according to the design rules. Thereafter, one or more pieces of feature information pertaining to the defective feature types are judged as one or more pieces of defect information because the feature information differ from the referential feature information. Also, the narrow width area is judged as a piece of defect information.

Also, a macro-inspection is performed in the specific shape detecting means and the second comparing and judging means in parallel to the micro-inspection. In detail, one or more specific shapes and those particular positions in the wiring pattern of the processed bi-level image are detected as pieces of feature codes in the specific shape detecting means. In this case, there is an probability that one or more defective shapes of the wiring pattern are included in the specific shapes. Therefore, the feature codes are compared with referential feature codes in the second comparing and judging means. The referential feature codes are stored in the referential feature code storing means and denote one or more referential shapes and those referential positions in a non-defective printed wiring board formed according to a desired design. Thereafter, one or more feature codes pertaining to the defective shapes are judged as one or more defects because the feature codes differ from the referential feature codes.

Accordingly, because a micro-inspection in which one or more feature types of the wiring pattern such as a line width of a signal line are detected in the design rule detecting means is performed in parallel to a macro-inspection in which one or more specific shapes of the wiring pattern such as a corner of a rectangular wiring pattern are detected in the specific shape detecting means even though the wiring pattern is not divided into a plurality of pattern regions, various types of defects existing in the printed wiring board can be strictly detected with a high accuracy without overlooking any defect regardless of whether the defects are large sized defects detected by the macro-inspection or small sized defects detected by the micro-inspection.

Also, it is preferred that the specific shape detecting means comprise:

a direction code adding circuit for adding one of eight types direction codes to each of contour pixels placed in edges of the wiring pattern in the processed bi-level image, each of the direction codes indicating a direction of an edge of the wiring pattern; and a feature code producing circuit for producing a corner code from a pair of different types direction codes added to a pair of contour pixels adjacent to each other in the direction code adding circuit to indicate a corner of the wiring pattern existing in a feature point and outputting the corner code and positional coordinates of the feature point as a feature code to the second comparing and judging means.

In the above configuration, one of eight types direction code is added to each of contour pixels of the wiring pattern in the direction code adding circuit. Because the contour pixels are placed in edges of the wiring pattern, the direction codes indicate directions of the edged. Thereafter, a corner code is produced from a pair of different types direction codes added to a pair of contour pixels adjacent to each other in the feature code producing circuit. Because the corner code is produced from the different types direction codes, the corner code indicates a corner of the wiring pattern.

Accordingly, in cases where the feature codes are compared with the referential feature codes in the second comparing and judging means, a macro defect indicated by a plurality of corners can be detected in the wiring pattern.

Also, it is preferred that the second comparing and judging means comprise:

an inspected serial codes register for registering a series of feature codes produced by serially connecting a plurality of feature codes output from the feature code producing circuit, each of pairs of feature codes adjacent to each other being placed within a permitted distance and being placed nearest to each other;

a referential serial codes register for serially connecting a plurality of referential feature codes stored in the referential feature code storing means to register a series of referential feature codes, each of pairs of referential feature codes adjacent to each other being placed within the permitted distance and being placed nearest to each other;

a serial codes comparing circuit for comparing the series of feature codes produced in the serial codes producing circuit with the series of referential feature codes registered in the referential serial codes register; and a judging circuit for judging whether or not the corner codes and the positional coordinates of the series of feature codes agree with those of the series of referential feature codes according to a compared result obtained in the serial codes comparing circuit and reporting a piece of defect information in cases where the corner codes and the positional coordinates of the series of feature codes do not agree with those of the series of referential feature codes.

In the above configuration, a plurality of feature codes are serially connected to produce a series of feature codes, and the series of feature codes is registered in the inspected serial codes register. Therefore, many series of feature codes are registered in the inspected serial codes register. Also, many series of referential feature codes are registered in the referential serial codes register in the same manner. Thereafter, each of the referential feature codes is compared with a series of feature codes in the serial codes comparing circuit. Thereafter, it is judged in the judging circuit whether or not the corner codes and the positional coordinates of the series of feature codes agree with those of the series of referential feature codes, and a piece of defect information is reported.

Accordingly, because a series of corner changes is indicated by a series of feature codes, a defect at an edge of the wiring pattern can be strictly detected by finding out the difference between a series of corner changes indicated by a series of feature codes and a series of referential corner changes indicated by a series of referential feature codes. Also, even though the defect minutely occurs, the defect can be reliably detected.

Also, it is preferred that the second comparing and judging means comprise:

an inspected feature codes series file for registering an inspected feature codes series produced by serially connecting a plurality of feature codes output from the feature code producing circuit, each of pairs of feature codes adjacent to each other being placed within a permitted distance and being placed nearest to each other;

a referential feature codes series file for registering a series of referential feature codes produced by serially connecting a plurality of referential feature codes stored in the referential feature code storing means, each of pairs of referential feature codes adjacent to each other being placed within the permitted distance and being placed nearest to each other;

a serial codes correspondence examining circuit for examining correspondence of the feature codes in the inspected feature codes series registered in the inspected feature codes series file to the referential feature codes in the series of referential feature codes registered in the referential feature codes series file to find out paired feature codes not corresponding to any referential feature codes from the inspected feature codes series or to find out paired referential feature codes not corresponding to any feature codes from the referential feature codes series;

a specific pair codes judging circuit for judging whether or not the paired feature codes or the paired referential feature codes found out in the serial codes correspondence examining circuit are equivalent to specific pair codes, the specific pair codes being defined as paired feature codes or paired referential feature codes placed in a narrow permitted limit; and a similarity judging circuit for judging that the inspected feature codes series registered in the inspected feature codes series file is similar to the referential feature codes series registered in the referential feature codes series file to regard the wiring pattern indicated by the inspected feature codes series non-defective in cases where it is judged in the specific pair codes judging circuit that the paired feature codes or the paired referential feature codes are equivalent to specific pair codes.

In the above configuration, the correspondence of the feature codes in the inspected feature codes series to the referential feature codes in the series of referential feature codes is examined in the serial codes correspondence examining circuit, and paired feature codes not corresponding to any referential feature codes or paired reverential feature codes not corresponding to any feature codes are find out. Thereafter, it is judged in the specific pair codes judging circuit whether or not the paired feature codes or the paired referential feature codes are equivalent to specific pair codes. The specific pair codes are defined as paired feature codes or paired referential feature codes placed in a narrow permitted limit. In cases where the paired feature codes or the paired referential feature codes are judged to be specific pair codes it is judged in the similarity judging circuit that the inspected feature codes series is similar to the referential feature codes series. Therefore, the wiring pattern indicated by the inspected feature codes series is regarded as non-defective.

Accordingly, even though specific pair codes are formed in an inspected feature codes series because of a quantization error, a false inspection resulting from the quantization error can be prevented at a high reliability. Also, even though specific pair codes are formed in a referential feature codes series because a meaningless concavo-convex portion actually exists in a non-defective wiring pattern, the inspection of the wiring pattern can be correctly performed by disregarding the meaningless concavo-convex portion.

Also, it is preferred that the second comparing and judging means comprise:

an inspected feature codes series file for registering an inspected feature codes series produced by serially connecting a plurality of feature codes output from the feature code producing circuit, each of pairs of feature codes adjacent to each other being placed within a permitted distance and being placed nearest to each other;

a referential feature codes series file for registering a series of referential feature codes produced by serially connecting a plurality of referential feature codes stored in the referential feature code storing means, each of pairs of referential feature codes adjacent to each other being placed within the permitted distance and being placed nearest to each other;

a serial codes comparing and judging circuit for comparing the inspected feature code series registered in the inspected feature codes series file with the referential feature code series registered in the referential feature codes series file, and judging whether or not the inspected feature codes series agrees with the referential feature code series; and a defective shape judging circuit for inspecting whether or not one of a plurality of fundamental codes series indicating a plurality of defective shape types of the wiring pattern is included in the inspected feature codes series which is judged in the serial codes comparing and judging circuit not to agree with the referential feature code series, the wiring pattern indicated by the inspected feature codes series in which a fundamental codes series is included being judged to have a type of defective shape.

In the above configuration, in cases where it is judged in the serial codes comparing and judging circuit that the inspected feature codes series does not agree with the referential feature code series, it is inspected in the defective shape judging circuit whether or not one of a plurality of fundamental codes series indicating a plurality of defective shape types of the wiring pattern is included in the inspected feature codes series.

Therefore, in cases where a fundamental codes series is found out, a defective shape type of the wiring pattern can be specified. Also, a process control for the inspection of the printed wiring board can be easily performed because a defective shape type of the wiring pattern is specified.

Also, it is preferred that the second comparing and judging means additionally include:

lack or projection detecting means for detecting a particular feature codes series with a fundamental codes series indicating a lack or a projection as a defective shape type from a plurality of inspected feature codes series with the fundamental codes series inspected in the defective shape judging circuit;

defect area calculating means for calculating a defect area of the lack or the projection indicated by the particular feature codes series detected in the lack or projection detecting means;

defect area size judging means for judging whether or not the defect area is larger than an allowable value; and codes series deleting means for deleting the particular feature codes series in cases where it is judged in the defect area size judging means that the defect area is not larger than the allowable value, the wiring pattern indicated by the particular feature codes series being regarded as non-defective.

In the above configuration, a particular feature codes series in which a fundamental codes series indicating a lack or a projection is included is detected in the lack or projection detecting means. Thereafter, a defect area of the lack or the projection is calculated in the defect area calculating means, and it is judged in the defect area size judging means whether or not the defect area is larger than an allowable value. In cases where the defect area is not larger than the allowable value, the defect area is not required to be reported as a piece of defect information. Therefore, the particular feature codes series is deleted in the codes series deleting means not to report the particular feature codes series as a piece of defect information in cases where the defect area is not larger than the allowable value.

Accordingly, because a particular feature codes series pertaining to a lack or a projection is deleted in cases where a defect area of the lack or the projection is not larger than an allowable value, lacks and projections really required to be reported to an operator can be reported as pieces of defect information, and a fault judgement in which a small sized deformation similar to a lack or a projection is detected as a defective shape can be prevented.

Also, it is preferred that the specific shape detecting means comprise:

a direction code adding circuit for adding one of eight types direction codes to each of contour pixels placed in edges of the wiring pattern in the processed bi-level image, each of the direction codes indicating a direction of an edge of the wiring pattern;

a direction code changing unit for changing a direction code DC0 of a remarked contour pixel added in the direction code adding circuit to another direction code DCn added to two neighboring contour pixels adjacent to the remarked contour pixel in the direction code adding circuit in cases where the direction codes DCn of the neighboring contour pixels are the same as each other and differ from the direction code DC0 of the remarked contour pixel; and a feature code producing circuit for producing a corner code from a pair of different types direction codes added to a pair of contour pixels adjacent to each other in the direction code adding circuit and changed in the direction code changing unit to indicate a corner of the wiring pattern existing in a feature point and outputting the corner code and positional coordinates of the feature point as a feature code to the second comparing and judging means.

In cases where a quantization error occurs when the bi-level image is produced in the bi-level image producing means, a direction code DC0 of a remarked contour pixel of the wiring pattern is erroneously set. That is, even though direction codes DCn of two neighboring contour pixels adjacent to the remarked contour pixel are the same as each other, the direction code DC0 of the remarked contour pixel undesirably differs from the direction codes DCn of the neighboring contour pixels because of the quantization error influencing the remarked contour pixel. In this case, an unstable feature code is undesirably formed because of the quantization error.

To prevent the formation of the unstable feature code, the direction code DC0 of the remarked contour pixel is changed to the direction code DCn in the direction code changing unit in cases where the direction codes DCn of the neighboring contour pixels are the same as each other and differ from the direction code DC0 of the remarked contour pixel.

Accordingly, the formation of the unstable feature code resulting from a quantization error can be prevented.

BRIEF DESCRIPTION OF THE DRAWINGS

The objects, features and advantages of the present invention will be apparent from the following description taken in conjunction with the accompanying drawings, in which:

FIG. 5A shows the arrangement of pixels placed in a circular scanning window, numerals given to the pixels respectively denoting an omnidirectional distance (or an approximate Euclid's distance) from a remarked pixel expressed by a numeral "0" to dilate or erode (or contract) a through hole area equidistantly to any direction;

FIG. 5B shows the arrangement of pixels placed in a square scanning window, numerals given to the pixels respectively denoting a lateral or longitudinal distance (or a chess-board distance) from a remarked pixel expressed by a numeral "0" to dilate or erode (or contract) a though hole area equidistantly to lateral and longitudinal directions. Also, the arrangement of pixels

FIG. 6B shows a distance converting image Idc produced in the design rule detecting section from the processed bi-level image Ibp which is output from the through hole filling section;

FIG. 7 is a constitutional circuit and block diagram of a specific shape detecting section shown in FIG. 1;

FIGS. 14A to 14H show examples of corners indicated by corner codes Cf(DC0,DCi);

FIG. 17 is a flow chart showing a procedure of the comparison of a series of feature codes and a series of referential feature codes performed in a serial codes comparing circuit 112 shown in FIG. 15A;

FIG. 18 shows an example of several series of referential feature codes registered in a referential serial feature codes file;

FIG. 19 shows an example of several series of feature codes registered in an inspected serial feature codes file;

FIG. 22 shows an example of an inspected code series A and a referential code series B;

FIG. 23 shows an example of the correspondence of feature codes in the inspected codes series A to the referential feature codes in the referential codes series B;

FIG. 24A shows a referential feature codes series Sr and an inspected feature codes series Si having a surplus codes series Ssc;

FIG. 24B shows a referential feature codes series Sr having a surplus codes series Ssc and an inspected feature codes series Si;

FIG. 27 shows an example of several referential feature codes series registered in a referential feature codes series file;

FIG. 28 shows an example of several inspected feature codes series registered in an inspected feature codes series file;

FIG. 30C shows the arrangement of direction codes indicating an open-end portion of a wiring pattern as a defective shape type;

FIG. 30D shows the arrangement of direction codes indicating a protrusion portion of a wiring pattern as a defective shape type;

FIG. 30E shows the arrangement of direction codes indicating a residue portion of a wiring pattern as a defective shape type;

FIG. 30F shows the arrangement of direction codes indicating a pinhole portion of a wiring pattern as a defective shape type;

FIG. 31A shows eight fundamental codes series respectively indicating the short shown in FIG. 30A;

FIG. 31B shows eight fundamental codes series respectively indicating the open-end shown in FIG. 30C;

FIG. 31C shows eight fundamental codes series respectively indicating the lack shown in FIG. 30B;

FIG. 31D shows eight fundamental codes series respectively indicating the projection shown in FIG. 30D;

FIG. 31E shows a fundamental codes series indicating the remaining copper shown in FIG. 30E;

FIG. 31F shows a fundamental codes series indicating the pinhole shown in FIG. 30F;

FIG. 33 shows an example of referential feature codes series registered in a defect information memory shown in FIG. 1;

FIG. 38 is a constitutional block diagram of the CPU shown in FIG. 9 according to a seventh embodiment of the present invention;

FIG. 39 shows an example of an inspected feature codes series in which paired codes I18 and I81 and specific pair codes I12 and I21 are included;

FIG. 44 shows the function of a look up table of the first direction code changing circuit shown in FIG. 41 in tabular form;

FIG. 45 shows the function of a look up table of the second direction code changing circuit shown in FIG. 41 in tabular form;

FIG. 46 shows an example of a direction code image Idc in which contour pixels of the wiring pattern have direction codes;

FIGS. 47A to 47C show a direction code of a remarked pixel and two direction codes of a pair of neighboring pixels picked up from the direction code image Idc shown in FIG. 46; and FIGS. 47D to 47F show a direction code of a remarked pixel and two direction codes of a pair of neighboring pixels, the direction code of the remarked pixel being changed in the direction code changing unit shown in FIG. 40.

DESCRIPTION OF THE PREFERRED EMBODIMENTS

Preferred embodiments of a wiring pattern inspection apparatus according to the present invention are described with reference to drawings.

A first embodiment of a wiring pattern inspection apparatus is described with reference to FIGS. 1 to 9.

Figure 1:
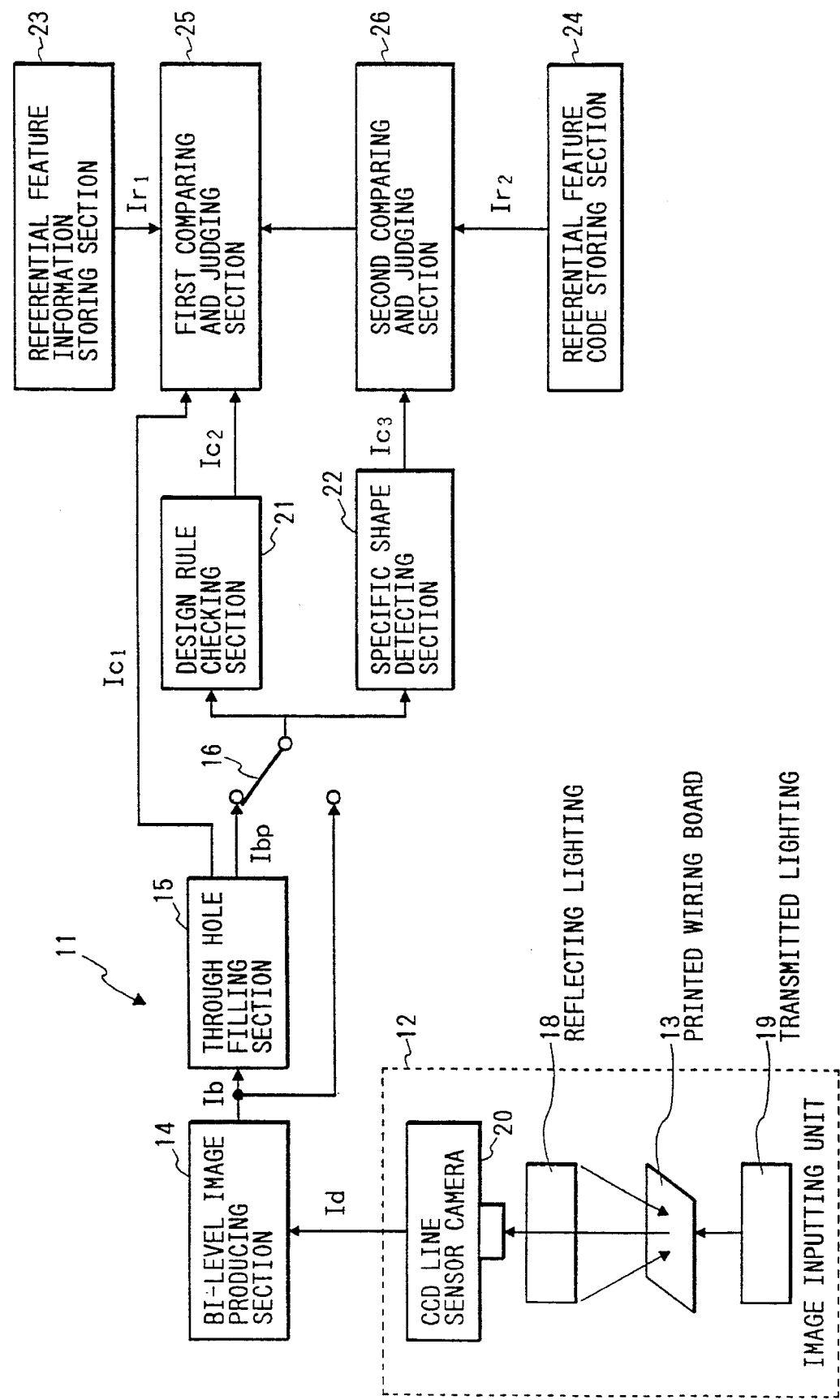
FIG. 1 is a constitutional block diagram of a wiring pattern inspection apparatus according to first to eighth embodiments of the present invention.
Figure 2A:
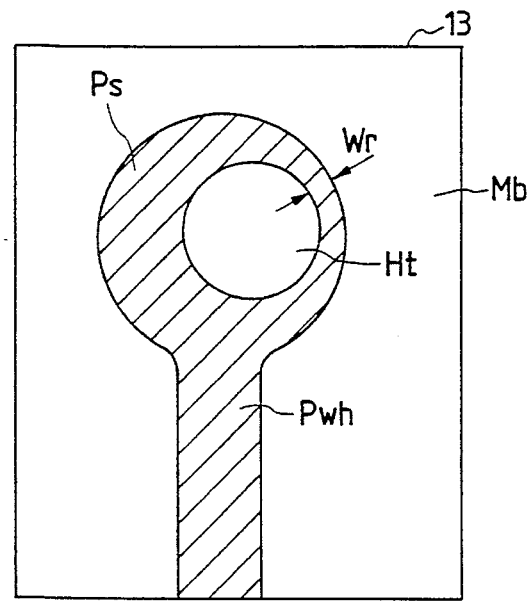
FIG. 2A shows a wiring pattern having a pad seat and a through hole surrounded by the pad seat which are formed on a base material of a printed wiring board.

FIG. 1 is a constitutional block diagram of a wiring pattern inspection apparatus according to a first embodiment of the present invention. FIG. 2A shows a holed wiring pattern having a pad seat and a through hole surrounded by the pad seat which are formed on a base material of a printed wiring board.

As shown in FIG. 1, a wiring pattern inspection apparatus 11 comprises an image inputting unit 12 for producing a gray level image Id of a printed wiring board 13 on which a holed wiring pattern including a pad seat and a through hole placed in the pad seat are formed, a bi-level section 14 for converting the gray level image Id into a bi-level image Ib in which the holed wiring pattern including the pad seat is expressed by a group of "1"-valued pixels (or a group of black pixels) and a base material surrounding the holed wiring pattern is expressed by a group of "0"-valued pixels (or a group of white pixels), a through hole filling section 15 for extracting pixels of the bi-level image Ib corresponding to the through hole by separating the pixels of the through hole from pixels of the holed wiring pattern, producing an image of a filled through hole which is formed by changing the values ("0") of the pixels in the through hole to "1"-values, and detecting a narrow width area of the pad seat in which a seat remaining width of the pad seat narrow ed by the through hole is lower than a reference width, and a switch 16 for bypassing the through hole filling section 15 in cases where the through hole is not actually formed in the printed wiring board 13.

The image inputting unit 12 comprises a reflecting lighting 18 for illuminating the printed wiring board 13 with diffused light from above the printed wiring board 13, a transmitted lighting 19 for illuminating the printed wiring board 13 with pulsed light from under the printed wiring board 13, and a charge coupled device (CCD) line sensor camera 20 for producing the gray level image Id of the holed wiring pattern and the through hole illuminated by the reflecting lighting 18 and the transmitted lighting 19.

As shown in FIG. 2A, a holed wiring pattern Pwh of which an end is widened to form a pad seat Ps is formed on a base material Mb of the printed wiring board 13. Also, a through hole Ht surrounded by the pad seat Ps is formed to electrically connect a first layer of circuit with a second layer of circuit through the holed wiring pattern Pwh and a conductive material packed into the through hole Ht. In this case, because a width of the holed wiring pattern Pwh is widened at the pad seat Ps, the pad seat Ps has a seat remaining width Wr between the through hole Ht and the base material Mb even though the through hole Ht is digged in the pad seat Ps. Also, in cases where a central axis of the through hole Ht is placed in the neighborhood of a center of the pad seat Ps, the seat remaining width Wr is equal to or larger than a reference width.

In the above configuration of the wiring pattern inspection apparatus 11, an action of the apparatus 11 performed prior to a micro-inspection and a macro-inspection of the printed wiring board 13 is described.

The printed wiring board 13 to be inspected is illuminated with diffused light of the reflecting lighting 18 and pulsed light of the transmitted lighting 19 from the upward and downward, and the printed wiring board 13 is photographed by the CCD line sensor camera 20 to produce a gray level image Id of the printed wiring board 13. A wavelength of the diffused light of the reflecting lighting 18 is near to 600 nm, so that a difference in reflecting luminance between the base material Mb (for example, glass epoxy) of the printed wiring board 13 and the holed wiring pattern Pwh made of copper becomes large. In other words, the gray level image Id can be easily converted into a bi-level image Ib. A light source of the reflecting lighting 18 is formed of a super high luminance type of light emitting diode (LED) (for example, GaAlAs of which a wavelength is 660 nm or an InGaAl of which a wavelength is 620 nm) which is merchandised. For example, the super high luminance type of LEDs of the reflecting lighting 18 are arranged in array to illuminate the printed wiring board 13 from various directions. Also, a diffused beam type of high luminance LEDs representing the transmitted lighting 19 are arranged in a line. The reason of the arrangement is described in the Japanese Published Unexamined Patent Application No. 120448 of 1992 and in the Japanese Published Unexamined Patent Application No. 60535 of 1993 which are submitted by the same inventors as those in this application. In detail, when the printed wiring board 13 is illuminated with pulsed transmitted light of the transmitted lighting 19 in synchronization with a horizontal synchronous signal (not shown) of the CCD line sensor camera 20, a response speed of the transmitted lighting 19 is heightened, and a pulse operation of the transmitted light can be performed at a high speed. In this embodiment, the transmitted lighting 19 is repeatedly switched on and off at line cycles in synchronization with the horizontal synchronous signal of the CCD line sensor camera 20.

Figure 2B:
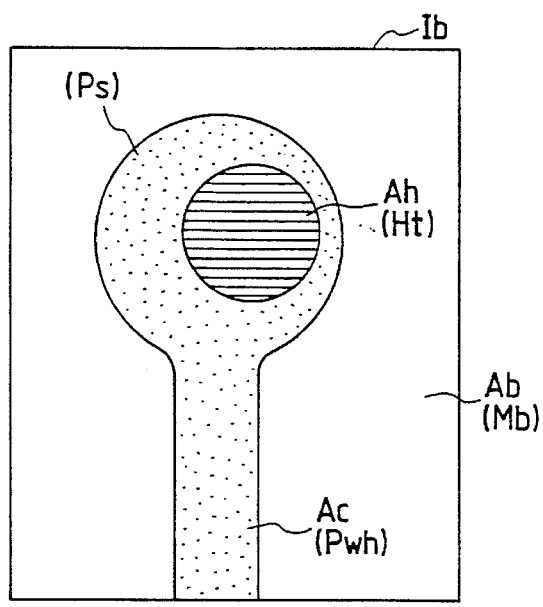
FIG. 2B shows a bi-level image Ib in which the wiring pattern and the through hole shown in FIG. 2A is drawn.

The gray level image Id produced in the CCD camera 20 is converted into a bi-level image Ib in the bi-level section 14. In detail, a threshold level is determined according to a gray level histogram prepared in advance, and values of pixels in the bi-level image Ib are determined by judging whether or not each of gray levels in the gray level image Id is higher than the threshold level. As a result, as shown in FIG. 2B, values of conducting side pixels of a conducting area Ac corresponding to the holed wiring pattern Pwh including the pad seat Ps are set to "1" in the bi-level image Ib, and values of base side pixels of a base side area Ab corresponding to the base material Mb are set to "0" in the bi-level image Ib. Also, because the through hole Ht of the printed wiring board 13 is illuminated with the pulsed light of the transmitted lighting 19, a stripped pattern is formed by a group of hole side pixels of a through hole area Ah corresponding to the through hole Ht in the bi-level image Ib. In other words, a line of "1"-valued hole side pixels and a line of "0"-valued hole side pixels are alternately arranged in the though hole area Ah.

Figure 2C:
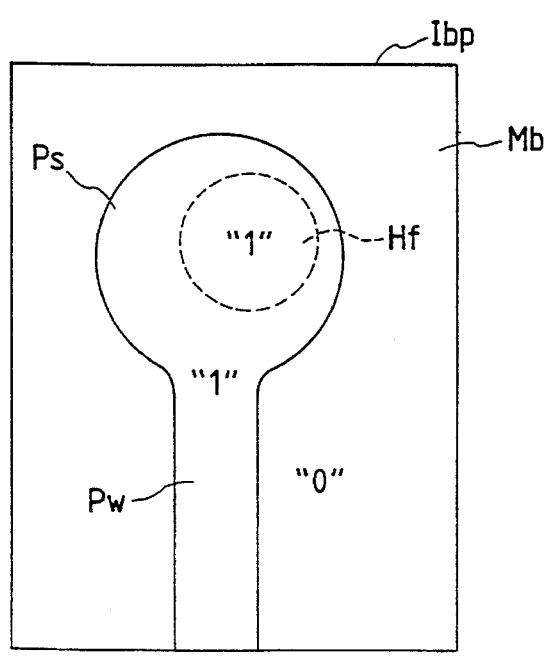
FIG. 2C shows a processed bi-level image Ibp in which the wiring pattern and the through hole virtually filled are drawn.

Thereafter, the bi-level image Ib is transferred to the through hole filling section 15. In the section 15, the through hole area Ah represented by the hole side pixels is extracted from the bi-level image Ib, and a seat remaining width Wr of the pad seat Ps is detected. In cases where the seat remaining width Wr is lower than a reference width, a shortage area in which the seat remaining width Wr is lower than the reference width is detected. Also, the values of the hole side pixels in the bi-level image Ib are set to "1" which is the same as those of the conducting side pixels. Therefore, as shown in FIG. 2C, the through hole Ht is virtually filled to produce a filled through hole Hr. The operation performed in the section 15 is described in detail with reference to FIGS. 3A, 3B.

Figure 3B:
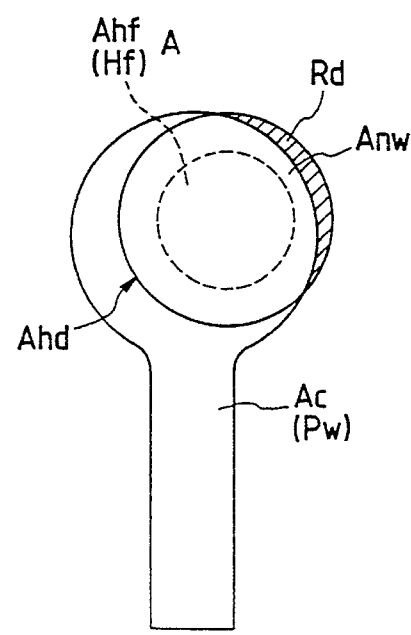
FIG. 3B shows a positional relationship between the wiring pattern having the filled through hole in a processed bi-level image and a dilated through hole area.
Figure 3A:
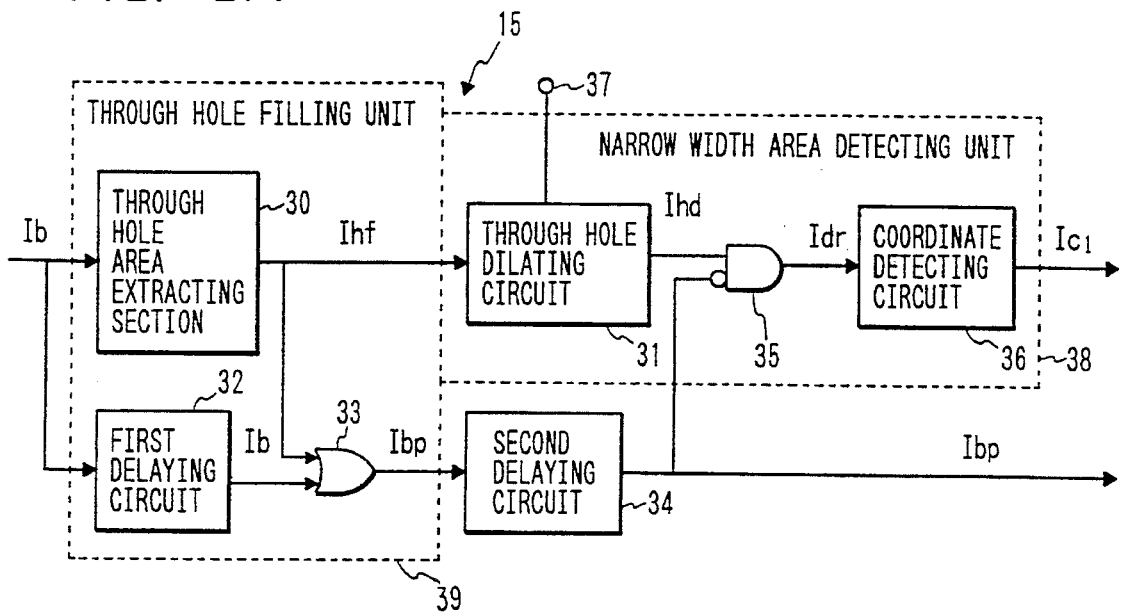
FIG. 3A is a constitutional block diagram of a through hole filling section shown in FIG. 1.

FIG. 3A is a constitutional block diagram of the through hole filling section 15, and FIG. 3B shows a positional relationship between a wiring pattern Pw having the filled through hole in a processed bi-level image and a dilated through hole area.

As shown in FIG. 3A, the through hole filling section is comprises a through hole area extracting section 30 for extracting the through hole area Ah from the bi-level image Ib, a through hole dilating circuit 31 for dilating the through hole area Ah by the reference width to produce a dilated through hole area Ahd, a first delaying circuit 32 for delaying the bi-level image Ib produced in the bi-level section 14, a OR gate 33 for receiving the bi-level image Ib delayed in the first delaying circuit 32 and the through hole area Ah extracted in the through hole area extracting section 30 and outputting a processed bi-level image Ibp in which a filled through hole area Ahf corresponding to the filled through hole Hf exists, a second delaying circuit 34 for delaying the processed bi-level image Ibp output from the OR gate 33 to synchronize the processed bi-level image Ibp with the dilated through hole area Ahd produced in the through hole dilating circuit 31, an AND gate 35 for receiving the dilated through hole area Ahd and the processed bi-level image Ibp synchronized in the second delaying circuit 34 to determine a discordant region Rd between the dilated through hole area Ahd and the wiring pattern Pw having the filled through hole Hf in the processed bi-level image Ibp as shown in FIG. 3B and outputting the discordant region Rd, a coordinate detecting circuit 36 for detecting coordinates of a narrow width area Anw placed in the holed wiring pattern Pwh adjacent to the discordant region Rd, and a terminal 37 for setting a degree of the dilatation performed in the through hole dilating circuit 31.

In the above configuration, the operation performed in the through hole filling section 15 is described.

The bi-level image Ib produced the bi-level section 14 has the conducting area Ac which is composed of the conducting side pixels set to "1", the base material area Ab which is composed of the base side pixels set to "0" and the through hole area Ah which is composed of the "1"-valued hole side pixels and the "0"-valued hole side pixels alternately arranged. The through hole area Ah of The bi-level image Ib is extracted in the through hole area extracting section 30, and all of the values of the hole side pixels are set to "1" to produce an image Ihf of a filled through hole area Ahf corresponding to the filled through hole Hr. The image Ihf is transferred to the OR gate 33 and the through hole dilating circuit 31. Also, the bi-level image Ib is delayed in the first delaying circuit 32 to synchronize the bi-level image Ib with the through hole area Ah of which the hole side pixels are set to "1" in the through hole area extracting section 30. Thereafter, the bi-level image Ib delayed is transferred to the OR gate 33.

In the OR gate 33, a processed bi-level image Ibp in which the through hole Ht is virtually filled is produced by adding the image Ihf and the bi-level image Ib synchronized with each other. That is, the hole side pixels of the through hole area Ah are set to the values "1" in the processed bi-level image Ibp, the conducting pixels of the conducting area Ac remain the values "1", and the base side pixels of the base side area Ab remain the values "0". Therefore, a group of the through hole area extracting section 30, the first delaying circuit 32 and the OR gate 33 functions as a through hole filling unit 39. Also, in the through hole dilating circuit 31, the through hole area Ah is dilated by the reference width set in the terminal 37, and a dilated through hole area Ahd is produced and transferred to the AND gate 35. In this case, because a degree of the dilatation in the circuit 31 is set to the reference width, the dilated through hole area Ahd is protruded from the conducting area Ac in cases where the seat remaining width Wr is lower than the reference width. Thereafter, the processed bi-level image Ibp output from the OR gate 33 is delayed in the second de laying circuit 34 to synchronize the processed bi-level image Ibp with an image Ihd of the dilated through hole area Ahd output from the through hole dilating circuit 31 and is transferred to the AND gate 35. Also, the processed bi-level image Ibp delayed is output from the through hole filling section 15.

In the AND gate 35, as shown in FIG. 3B, a discordant region Rd of the dilated through hole area Ahd which is protruded from the conducting area Ac is determined. That is, discordant pixels corresponding to the discordant region Rd have the values "1", and other pixels surrounding the discordant pixels have th values "0". In this case, the existence of the discordant region Rd denotes that the seat remaining width Wr is lower than the reference width. Therefore, the printed wiring board 13 can be inspected by judging whether or not the discordant region Rd exists. For example, in cases where the printed wiring board 13 in which the seat remaining width Wr is lower than a total width of five pixels is planned to be judged as a defective printed wiring board, the reference width is set to the total width of five pixels in the terminal 37. Thereafter, an image Idr of the discordant region Rd is transferred to the coordinate detecting circuit 36, and positional coordinates of a narrow width area Anw placed in the holed wiring pattern Pwh adjacent to the discordant region Rd are determined. The positional coordinates of the narrow width area Anw are output as a piece of feature information Ic1. The feature information Ic1 denotes a piece of defect information indicating that a defect denoting the shortage of the seat remaining width Wr exists in the holed wiring pattern Pwh of the printed wiring board 13. Therefore a group of the through hole dilating circuit 31, the AND gate 35, and the coordinate detecting circuit 36 functions as a narrow width area detecting unit 38. Pieces of feature information Ic1 are output from the through hole filling section 15 in the same manner in scanning order of the printed wiring board 13.

The operation performed in the through hole area extracting section 30 is described in detail with reference to FIGS. 4A, 4B.

Figure 4A:
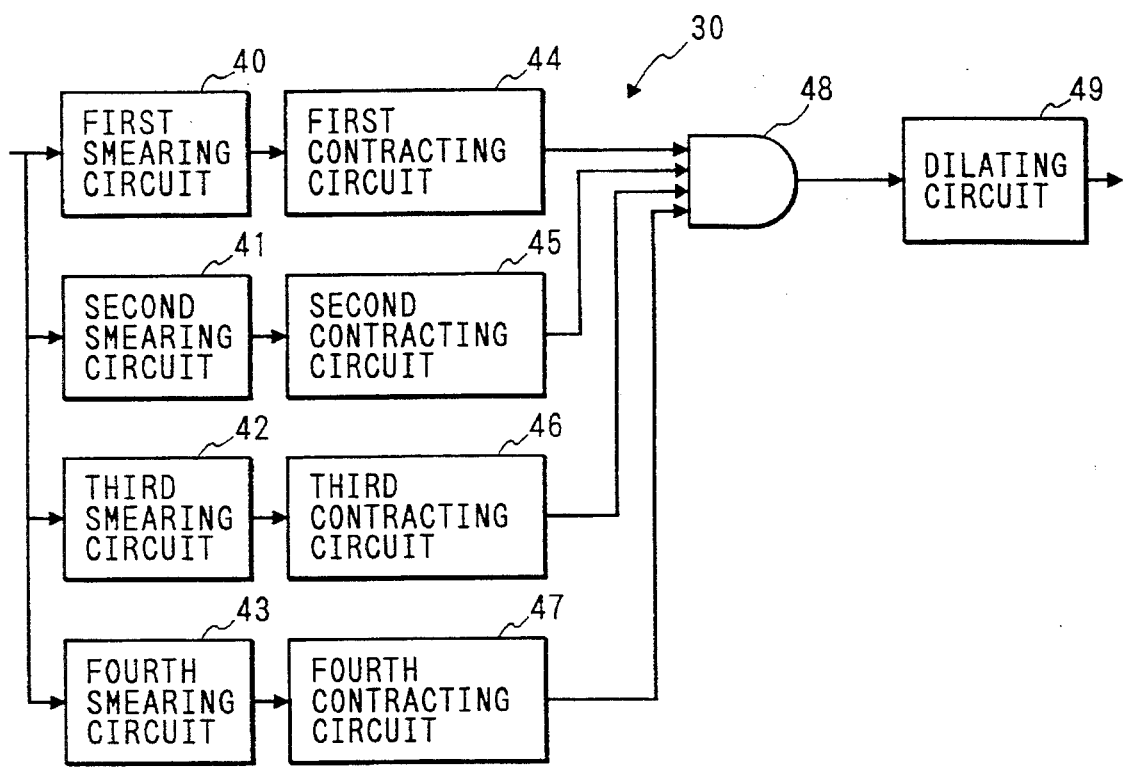
FIG. 4A is a constitutional block diagram of a through hole area extracting section shown in FIG. 3A.

FIG. 4A is a constitutional block diagram of the through hole area extracting section 30.

As shown in FIG. 4A, the through hole area extracting section 30 comprises a first smearing circuit 40 for smearing the striped pattern of the through hole area Ah in a first direction to produce an image of a first smeared through hole area by changing the values of the hole side pixels of the through hole area Ah to "1", a first contracting circuit 44 for contracting the first smeared through hole area by a pixel width in the first direction, a second smearing circuit 41 for smearing the striped pattern of the thorough hole area Ah in a second direction to produce an image o f a second smeared through hole area by changing the values of the hole side pixels of the through hole area Ah to "1", a second contracting circuit 45 for contracting the second smeared through hole area by a pixel width in the second direction, a third smearing circuit 42 for smearing the striped pattern of the through hole area Ah in a third direction to produce an image of a third smeared through hole area by changing the values of the hole side pixels of the through hole area Ah to "1", a third contracting circuit 46 for contracting the third smeared through hole area by a pixel width in the third direction, a fourth smearing circuit 43 for smearing the striped pattern of the through hole area Ah in a fourth direction to produce an image of a fourth smeared through hole area by changing the values of the hole side pixels of the through hole area Ah to "1", a fourth contracting circuit 47 for contracting the fourth smeared through hole area by a pixel width in the fourth direction, an AND gate 48 for detecting a common smeared through hole area among the first, second, third and fourth smeared through hole areas contracted in the contracting circuits 44 to 47, and a dilating circuit 49 for dilating the common smeared through hole area to produce an image of the filled through hole area Ahf corresponding to the filled through hole Hf.

Each of the smearing circuits 40 to 43 has a 3×3 window scanning circuit (not shown) for extracting nine pixels P0 to P8 arranged in a 3×3 scanning window from the bi-level image Ib, and an arithmetic logic circuit (not shown) for performing a logical operation with the pixels P0 to P8. Because an image processing with the 3×3 scanning window is conventionally known, a detail configuration of the 3×3 window scanning circuit and the arithmetic logic circuit is omitted.

Figure 4B:
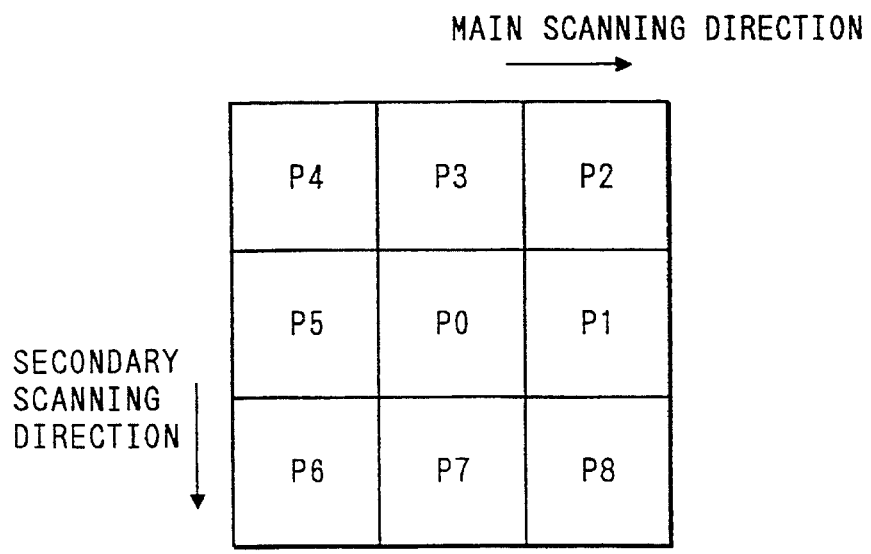
FIG. 4B shows a remarked pixel P0 and neighboring pixels P1 to P8 scanned with a 3×3 scanning window.

In the above configuration of the through hole area extracting section 30, as shown in FIG. 4B, all of pixels of the bi-level image Ib are scanned with a 3×3 scanning window by sliding the 3×3 scanning window in a main scanning direction and a secondary scanning direction according to the function of the 3×3 window scanning circuit. In cases where the 3×3 scanning window is placed at coordinates (x,y) of the bi-level image Ib to arrange a pixel P0 placed in the coordinates (x,y) of the bi-level image Ib in the center of the 3×3 scanning window, the pixel P0 functions as a remarked pixel, and a logical operation is performed in each of the smearing circuits 40 to 43 with pixels P1 to P8 surrounding the remarked pixel P0.

In the first smearing circuit 40, the striped pattern of the through hole area Ah is smeared in a first direction according to an equation (1) to produce an image of a first smeared through hole area.

$$d0'=(\overline{d0*d*d3})*(d0+d1+d3) \tag{1}$$

Here symbols d0,d1,d3 denote binary values of the pixel P0,P1,P3, a symbol d0' denotes a binary value of a pixel P0' placed in the coordinates (x,y) of the first smeared through hole area, a symbol * denotes a logical multiply, a symbol + denotes a logical sum, and a symbol $\overline{di}$ denotes a logical NOT of a binary value di.

Therefore, the image of the first smeared through hole area is produced by selecting each of pixels of the bi-level image Ib as a remarked pixel P0.

In the second smearing circuit 41, the striped pattern of the through hole area Ah is smeared in a second direction according to an equation (2) to produce an image of a second smeared through hole area.

$$d0'=(\overline{d0*d3*d5})*(d0+d3+d5) \tag{2}$$

Here a symbol d5 denotes a binary value of the pixel P5.

Therefore, the image of the second smeared through hole area is produced in the same manner.

In the third smearing circuit 42, the striped pattern of the through hole area Ah is smeared in a third direction according to an equation (3) to produce an image of a third smeared through hole area.

$$d0'=(\overline{d0*d5*d7})*(d0+d5+d7) \qquad (3)$$

Here a symbol d7 denotes a binary value of the pixel P7.

Therefore, the image of the third smeared through hole area is produced in the same manner.

In the fourth smearing circuit 43, the striped pattern of the through hole area Ah is smeared in a fourth direction according to an equation (4) to produce an image of a fourth smeared through hole area.

$$d0'=(\overline{d0*d7*d1})*(d0+d7+d1) \qquad (4)$$

Therefore, the image of the fourth smeared through hole area is produced in the same manner.

The operations in the smearing circuits 40 to 43 are independently performed in parallel. In this case, because a contour line of the striped pattern of the through hole area Ah remains in each of the smeared through hole areas, the contour line is deleted by performing an arithmetic operation according to an equation (5) in each of the contracting circuits 44 to 47.

$$d0''=(d0'*d1'*d3'*d5'*d7') \qquad (5)$$

Here symbols d0',d1',d3',d5' and d7' denote binary values of pixel P0',P1',P3', P5' and P7' of each of the smeared through hole areas, and a symbol d0" denotes a binary value of a pixel P0" of each of the smeared through hole areas contracted in the contracting circuits 44 to 47.

Thereafter, a logical multiply of the first, second, third and fourth smeared through hole areas contracted in the contracting circuits 44 to 47 is calculated in the AND gate 48, so that a common smeared through hole area is detected. Thereafter to compensate the common smeared through hole area for the contraction in the contracting circuits 44 to 47, the common smeared through hole area is dilated according to an equation (6) in the dilating circuit 49, and an image of the filled through hole area Ahf corresponding to the filled through hole Hf is produced.

$$D0=(d0''+d1''+d2''+d3''+d4''+d5''+d6''d7''+d8'') \qquad (6)$$

Here symbols d1",d2",d3",d4",d5",d6",d7" and d8" denote binary values of pixels P1",P2",P3",P4",P5",P6",P7" and P8" of each of the smeared through hole areas contacted in the contracting circuits 44 to 47, and a symbol D0 denotes a binary value of a pixel P0 placed in the coordinates (x,y) of the filled through hole area Ahf.

Next, the operation performed in the through hole dilating circuit 31 is described in detail with reference to FIGS. 5A, 5B.

The arrangement of pixels placed in a circular scanning window is shown in FIG. 5A. Numerals given to the pixels respectively denote an omnidirectional distance (or an approximate Euclid's distance) from a remarked pixel expressed by a numeral "0" to dilate or erode (or contract) the though hole area Ah equidistantly to any direction. The arrangement of pixels placed in a square scanning window is shown in FIG. 5B. Numerals given to the pixels respectively denote a lateral or longitudinal distance (or a chessboard distance) from a remarked pixel expressed by a numeral "0" to dilate or erode (or contract) the though hole area Ah equidistantly to lateral and longitudinal directions. Also, the arrangement of pixels placed in a rhombic scanning window is well-known to arrange the pixels having numerals which denote a city-block distance.

Image processing techniques utilizing the circular scanning window, the square scanning window and the rhombic scanning window are well-known and described in a literature (A. Rosenfeld & A. C. Kak (translated to Japanese by M. Nagao) "Digital Image Processing" Kindaikagaku Co, LTD. (1992)). Therefore, the detail description of the image processing techniques is omitted.

The object in the through hole dilating circuit 31 is to detect the shortage of the seat remaining width Wr, so that it is required to isotropically dilate or erode (or contract) the though hole area Ah in any direction. Therefore, the circular scanning window in which a remarked pixel and pixels surrounding the remarked pixel are arranged as shown in FIG. 5A is utilized in this embodiment. Also, in cases where an input image such as an image of the though hole area Ah is dilated by a total width of k pixels, pixels of the input image are raster-scanned for each of the pixels with the scanning window, and a remarked pixel and neighboring pixels having numerals equal to or lower than a numeral "5" are selected each time the remarked pixel is determined in a raster scanning. Thereafter, binary values of the remarked pixel and the neighboring pixels are input to a OR gate to perform a logical sum, and a group of output binary values of the pixels are obtained. Therefore, a dilated image composed of the pixels having the output binary values can be obtained. In contrast, in cases where an input image such as an image of the though hole area Ah is eroded by a total width of k pixels, the remarked pixel and the neighboring pixels are selected in the same manner each time the remarked pixel is determined in a raster scanning. Thereafter, binary values of the remarked pixel and the neighboring pixels are input to an AND gate to perform a logical multiply, and a group of output binary values of the pixels are obtained. Therefore, an eroded image composed of the pixels having the output binary values can be obtained.

Accordingly, because the through hole area Ah is isotropically dilated in any direction in the through hole dilating circuit 31, the discordant region Rd can be reliably detected in cases where the seat remaining width Wr is lower than the reference width, and the coordinates of the discordant region Rd can be determined to recognize a shortage area of the pad seat Ps in which the seat remaining width Wr is narrower than an allowable width. Therefore, the inspection of the wiring pattern Pw can be easily performed.

In this embodiment, the through hole filling section 15 is operated because the through hole Ht is actually digged in the printed wiring board 13. However, in cases where the through hole Ht has not yet been digged in the printed wiring board 13, a filling operation for the through hole Ht is not required. Therefore, the bi-level image Ib produced in the bi-level section 14 bypasses the through hole filling section 15 by changing a switch 16.

Next, a micro-inspection and a macro-inspection of the printed wiring board 13 based on the operation of the through hole filling section 15 are described.

The wiring pattern inspection apparatus 11 additionally comprises a design rule checking section 21 for detecting one or more feature types and those particular positions in the wiring pattern of the processed bi-level image Ibp as pieces of feature information Ic2 by measuring a width of the wiring pattern and a line distance between wiring patterns, one or more defective feature types which break one or more design rules of the wiring pattern or denote one or more open-ends or branches of the wiring pattern being included in the feature types, a specific shape detecting section 22 for detecting one or more specific shapes such as a corner and the like and those particular positions in the wiring pat tern of the processed bi-level image Ibp as pieces of feature codes Ic3, one or more defective shapes of the wiring pattern being included in the specific shapes, a referential feature information storing section 23 for storing one or more referential feature types and those referential positions in a non-defective printed wiring board of which a non-defective wiring pattern is formed according to the design rules as pieces of referential feature information Ir1, a referential feature code storing section 24 for storing one or more referential shapes and those referential positions in a non-defective printed wiring board of which a non-defective wiring pattern is formed according to a desired design as one or more referential feature codes Ir2, a first comparing and judging section 25 for comparing the feature information Ic2 detected in the design rule checking section 21 with the referential feature information Ir1 stored in the referential feature information, storing section 23 and judging the feature information Ic1 transferred from the through hole filling section 15 and one or more pieces of feature information Ic2 detected in the design rule checking section 21 which differ from the referential feature information Ir1 as one or more pieces of defect information respectively indicating a type of a defect and a position of the defect, and a second comparing and judging section 26 for comparing the feature codes Ic3 detected in the specific shape detecting section 22 with the referential feature codes Ir2 stored in the referential feature code storing section 24 and judging one or more specific shapes indicated by one or more feature codes Ic3 which differ from the referential feature codes Ir2 as one or more defects.

A micro-inspection of the wiring pattern Pw is performed in the design rule checking section 21 to strictly inspect a narrow signal line with a high accuracy. Also, a macro-inspection of the wiring pattern Pw is performed in the specific shape detecting section 22 to roughly inspect a large scaled wiring pattern such as a surface mount device (SMD) pad or a a shield pattern.

In the above additional configuration of the wiring pattern inspection apparatus 11, the design rule checking section 21 and the specific shape detecting section 22 are described in detail with reference to FIGS. 6A, 6B.

As is described in the Japanese Published Unexamined Patent Application No. 252545 of 1991 and in the Japanese Patent Application No. 334009 of 1990 which are submitted by the same inventors as those in this application, following operations are performed in a design rule checking. That is, a distance image in which a distance from a border of a wiring pattern is displayed is produced from the wiring pattern at the same time that a skeleton of the wiring pattern is extracted from the wiring pattern, pattern widths along the skeleton of the wiring pattern are measured, and shapes of the skeleton such as a shape of a branching point of the skeleton and a shape of an end point of the skeleton are recognized. Therefore, a defective wiring pattern in which the shortage of a pattern width, an electric short or the open-end exists is detected.

Figure 6A:
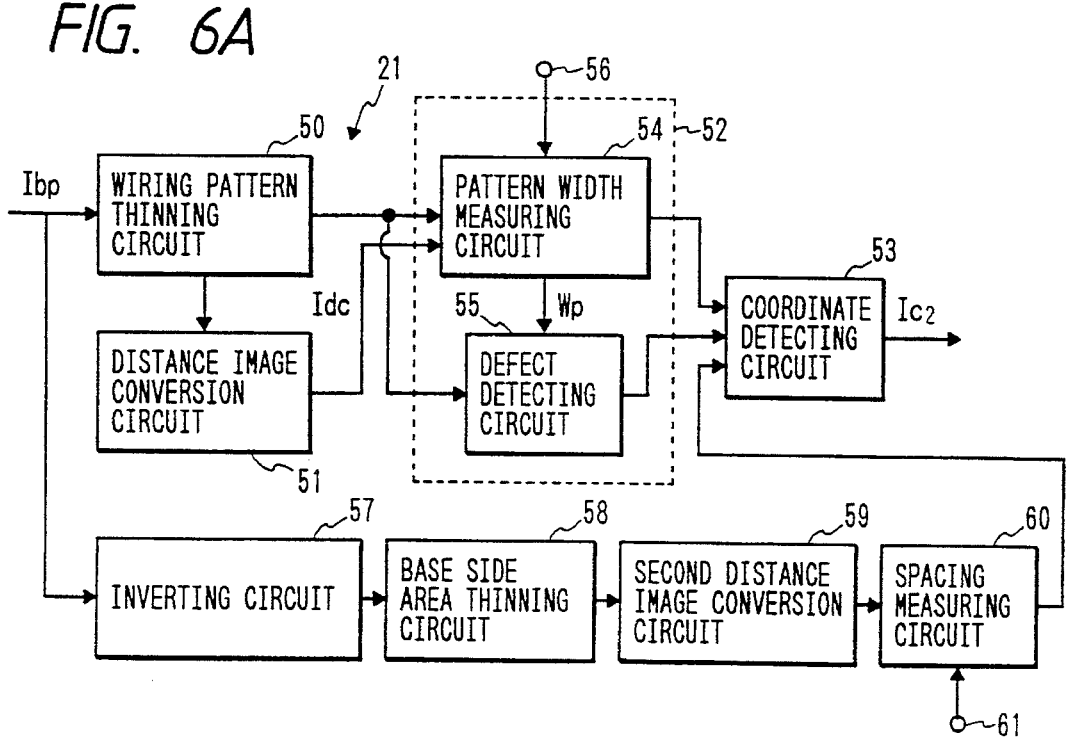
FIG. 6A is a constitutional block diagram of a design rule detecting section shown in FIG. 1.

FIG. 6A is a constitutional block diagram of the design rule checking section 21. FIG. 6B shows a distance image produced in the design rule checking section 21 from the processed bi-level image Ibp which is output from the through hole filling section 15.

As shown in FIG. 6A, the design rule checking section 21 comprises a wiring pattern thinning circuit 50 for thinning the wiring pattern Pw of the processed bi-level image Ibp, in which the through hole Ht is filled in the through hole filling section 15 while deleting the pixels of the wiring pattern Pw pixel by pixel from a border side of the wiring pattern Pw on condition that a thinned wiring pattern is not disconnected to form a skeleton Lc of the wiring pattern Pw, a distance image conversion circuit 51 for producing a distance image Idc shown in FIG. 6B from the processed bi-level image Ibp each time the wiring pattern Pw is thinned pixel by pixel in the wiring pattern thinning circuit 50 by giving a distance value to each of the pixels of the wiring pattern Pw from the border of the wiring pattern Pw, a feature extracting block 52 for extracting one or more violating widths, one or more branching points and ending points of the wiring pattern Pw of the wiring pattern Pw from the distance image Idc produced in the distance image conversion circuit 51 as feature types of the wiring pattern Pw by utilizing the skeleton Lc of the wiring pattern Pw produced in the wiring pattern thinning circuit 50, and a coordinate detecting circuit 53 for detecting positional coordinates of the feature types denoting the branching points, the ending points and the violating widths extracted in the feature extracting block 52.

The feature extracting block 52 comprises a pattern width measuring circuit 54 for measuring pattern widths of the wiring pattern Pw to detect the violating widths shorter than a referential pattern width Wf by referring the distance values given to the pixels of the distance image Idc and the skeleton Lc of the wiring pattern Pw, a defect detecting circuit 55 for detecting one or more defects in shapes of the wiring pattern Pw by recognizing shapes of the skeleton Lc such as a branching point and an ending point, and a terminal 56 for setting the referential pattern width Wf equal to a minimum pattern width Wmin of the wiring pattern Pw.

In the above configuration of the design rule checking section 21, the wiring pattern Pw is thinned by repeatedly deleting a contour pixel of the wiring pattern Pw placed at a border side of the wiring pattern Pw in the wiring pattern thinning circuit 50 on condition that connectivity of the wiring pattern Pw is maintained to form a skeleton Lc of the wiring pattern Pw. This thinning operation is a well-known image processing method. For example, the thinning operation performed in the circuit 50 has been proposed in a literature (H. Tamura "Further Considerations on Line Thinning Schemes", Technical Report, Institute of Electronic Information and Communication Engineers of Japan, PRL75-66 (1975)). In the literature, a thinning operation for deleting a layer of contour pixels is divided into four sub-iterations, and a layer of contour pixels is deleted from one of upper, lower, right and left sides in each of the sub-iterations. Finally, a skeleton having a pixel width is formed of a series of pixels connected to each other.

In the distance image conversion circuit 51, a distance value from the border of the wiring pattern Pw is given to each of the pixels of the wiring pattern Pw to produce a distance image Idc shown in FIG. 6B from the processed bi-level image Ibp. In detail, a distance value "1" is initially given to each of the pixels of the wiring pattern Pw in the processed bi-level image Ibp, and another distance value "0" is initially given to each of the pixels of the base material Mb in the processed bi-level image Ibp. Thereafter, the distance values given to the pixels of the wiring pattern Pw which are not deleted in the thinning operation for deleting a layer of contour pixels performed in the wiring pattern thinning circuit 50 are incremented each time the thinning operation is performed in the wiring pattern thinning circuit 50. Therefore, the distance values respectively denoting a distance from the border of the wiring pattern Pw are finally given to all pixels of the wiring pattern Pw including pixels of the skeleton Lc. As shown in FIG. 6B, each of the distance values is expressed by a number of two figures, and each of pixels relating to the skeleton Lc is enclosed with a square. In this case, as is described in the Japanese Patent Application No. 334009 of 1990, in cases where a layer of contour pixels is deleted while selectively controlling a first edge pattern composed of four connected pixels and a second edge pattern composed of eight connected pixels each time the thinning operation is performed, the distance image Idc in which the distance values are given to the pixels according to the omnidirectional distance (or the approximate Euclid's distance) shown in FIG. 5A can be obtained.

Thereafter, in the feature extracting block 52, an image of the skeleton Lc transferred from the thinning circuit 50 and the distance image Idc transferred from the convert circuit 51 are scanned with a 3×3 scanning window to detect one or more branching points and ending points existing in the wiring pattern Pw and one or more violating widths of the wiring pattern Pw as feature types. Thereafter, the feature types indicating the branching points, the ending points and the violating widths and positions of the branching points, the ending points and the violating widths are transferred to the coordinate detecting circuit 53 to detect the positional coordinates of the feature types.

In detail, the distance image IdC is scanned with a 3×3 scanning window Ws1 in the pattern width measuring circuit 54. That is, a central pixel P0 and eight neighboring pixels P1 to P8 are scanned with the 3×3 scanning window Ws1. When the central pixel P0 agrees with one of pixels of the skeleton Lc, a pattern width Wp of the wiring pattern Pw is measured with a distance value DV0 of the central pixel P0 and distance values DV1 to DV8 of the neighboring pixels P1 to P8 according to an equation (7).

$$Wp = DV0 + \left[ 1/8 \times \sum_{i=1}^{8} (DVi) \right] \quad (7)$$

Here a symbol [X] denotes to round X to the nearest whole number, a symbol + denotes an addition, and a symbol × denotes a multiplication. Thereafter, the pattern width Wp is transferred to the coordinate detecting circuit 53 and the defect detecting circuit 55 each time the pattern width Wp is measured in the circuit 54. Also, the pattern width Wp is compared with the minimum pattern width Wmin set at the terminal 56. In cases where the pattern width Wp is lower than the minimum pattern width Wmin, the detection of a violating width is informed the coordinate detecting circuit 53. For example, in cases where the 3×3 scanning window Ws1 is placed as shown in FIG. 6B, the pattern width Wp=2 (pixels) is obtained. In cases where the minimum pattern width Wmin=4 (pixels) is set, the pattern width Wp=2 is informed the coordinate detecting circuit 53 as a violating width.

Also, one or more branching points and ending points of the wiring pattern Pw are detected in the defect detecting circuit 55 by scanning an image of the skeleton Lc with a 3×3 scanning window Ws2. That is, a central pixel P0 and eight neighboring pixels P1 to P8 are scanned with the 3×3 scanning window Ws2. The detection of the branching points and the ending points is performed by utilizing a look up table having nine bit addresses. In the look up table, the judgement of an ending point is allocated in cases where an equation (8) is satisfied, and the judgement of a branching point is allocated in cases where an equation (9) is satisfied.

$$d0 = 1, \sum_{i=1}^{8} (di) \leq 3, \text{ and } \sum_{i=1}^{8} \{di^*(d_{i+1})\} = 1 \quad (8)$$

$$d0 = 1, \sum_{i=1}^{8} (di) \leq 4, \text{ and } \sum_{i=1}^{8} \{di^*(d_{i+1})\} \geq 3 \quad (9)$$

Here symbols d0 to d8 denote binary values of the pixels P0 to P8 in the same manner as in the equations (1) to (4). In cases where an ending point or a branching point is detected in the circuit 55 on condition that the pattern width Wp transferred from the circuit 54 is equal to or lower than a minimum pad seat size Tpad, a feature type indicating the ending point or the branching point and a position of the feature type are informed the coordinate detecting circuit 53. For example, as shown in FIG. 6B, in cases where the central pixel P0 in the 3×3 scanning window Ws2 agrees with a pixel Px of the skeleton Lc on condition that the minimum pad seat size Tpad=15 (pixels) is set, the equation (9) is satisfied, and Wp≦Tpad is satisfied. Therefore, a feature type indicating a branching point and a position of the branching point are informed the coordinate detecting circuit 53. Also, in cases where the central pixel P0 in the 3×3 scanning window Ws2 agrees with a pixel Py of the skeleton Lc on condition that the minimum pad seat size Tpad=15 (pixels) is set, the equation (8) is satisfied, and Wp≦Tpad is satisfied. Therefore, a feature type indicating an ending point and a position of the ending point are informed the coordinate detecting circuit 53.

Thereafter, in the coordinate detecting circuit 53, positional coordinates of the feature types indicating the branching points and the ending points detected in the circuit 55 and the pattern width Wp measured in the circuit 54 are detected, and pieces of feature information Ic2 respectively denoting a feature type and positional coordinates of the feature type are transferred to the first comparing and judging section 25. In this case, the feature information Ic2 are transferred to the first comparing and judging section 25 in scanning order of the printed wiring board 13.

Next, the inspection of a spacing between wiring patterns adjacent to each other is described.

As shown in FIG. 6A, the design rule checking section 21 additionally comprises an inverting circuit 57 for innverting binary values "0", "1" of the pixels of the processed bi-level image Ibp into inverted binary values "1", "0" to produce a inverted bi-level image Ibc, a base side area thinning circuit 58 for thinning a base side area Ab placed between wiring patterns adjacent to each other in the inverted bi-level image Ibc while deleting the pixels of the base side area Ab pixel by pixel from a border side of the base side area Ab on condition that a thinned base side area Ab is not disconnected to form a skeleton of the base side area, a second distance image conversion circuit 59 for producing a second distance image from the inverted bi-level image Ibc at the same time that the base side area Ab is thinned in the base side area thinning circuit 58 by giving a distance value from the border of the base side area Ab to each of the pixels, a spacing measuring circuit 60 for measuring a spacing between the wiring patterns to detect a spacing shorter than a referential spacing as a short spacing by referring the distance values given to the pixels of the second distance image and the skeleton of the base side area Ab, and a terminal 61 for setting the referential spacing denoting a minimum spacing allowed for the spacing.

In the above additional configuration, the processed bi-level image Ibp is inverted into an inverted bi-level image Ibc in the inverting circuit 57. In the inverted image Ibc, the pixels of the conducting area Ac are set to binary values "0", and the pixels of the base side area Ab are set to binary values "1". Thereafter, the base side area Ab of the inverted bi-level image Ibc are thinned in the base side area thinning circuit 58 in the same manner as in the wiring pattern thinning circuit 50, and a second distance image is produced from the inverted bi-level image Ibc in the second distance image conversion circuit 59 in the same manner as in the distance image conversion circuit 51. Thereafter, spacings between the wiring patterns are measured in the spacing measuring circuit 60, and a spacing shorter than a referential spacing set at the terminal 61 is detected as a short spacing in the same manner as in the pattern width measuring circuit 54. Thereafter, a position of the short spacing and a feature type indicating the short spacing are informed the coordinate detecting circuit 53, and positional coordinates of the short spacing are detected in the circuit 53. Thereafter, positional coordinates of the feature type indicating the short spacing are detected in the coordinate detecting circuit 53, and a piece of feature information Ic2 denoting the feature type and the positional coordinates is transferred to the first comparing and judging section 25. Therefore, pieces of feature information Ic2 are transferred to the first comparing and judging section 25 in scanning order of the printed wiring board 13.

Accordingly, because the wiring pattern Pw is thinned pixel by pixel in the wiring pattern thinning circuit 50 and the distance image Idc with the distance values from the border of the wiring pattern Pw is produced in the distance image conversion circuit 51, even though the wiring pattern Pw is narrow to function as a narrow signal line, pattern widths of the wiring pattern Pw, branching points of the wiring pattern Pw, ending points of the wiring pattern Pw and spacings between signal lines of the wiring pattern Pw can be detected without dividing the wiring pattern Pw into a plurality of pattern regions to strictly perform a micro-inspection of the wiring pattern Pw in the design rule checking section 21 with a high accuracy.

Also, in cases where the number or repetitions for deleting the pixels of the wiring pattern Pw pixel by pixel in the wiring pattern thinning circuit 50 is set to a prescribed number, a narrow signal line (or a pin, hole and a remaining copper) of the wiring pattern Pw can be selectively thinned to a skeleton (or a core point) having one pixel width (or a size of one pixel), and a wide wiring pattern is not thinned to a skeleton. Therefore, the narrow signal line and the like can be selectively inspected to strictly perform a micro-inspection of the wiring pattern Pw in the design rule checking section 21 with a high accuracy.

Next, the operation performed in the specific shape detecting section 22 is described with reference to FIGS. 7, 8.

FIG. 7 is a constitutional circuit and block diagram of the specific shape detecting section 22.

As shown in FIG. 7, the specific shape detecting section 22 comprises a 9×9 scanning window circuit 70 for scanning eighty one (9×9) pixels of the processed bi-level image Ibp transferred from the through hole filling section 15, a 3×3 scanning window circuit 71 arranged in the 9×9 scanning window circuit 70 for scanning nine (3×3) inner pixels Pi of the processed bi-level image Ibp, an edge detecting circuit 72 for detecting an edge of the wiring pattern Pw according to binary values of the inner pixels Pi scanned with the 3×3 scanning window circuit 71, a shape detecting look up table (LUT) 73 for detecting a particular pattern shape of the wiring pattern Pw according to an arrangement of binary values of sixteen outer pixels Po which are uniformly studded in the most outside layer of the circuit 70 on every other pixel and are hatched, a gate circuit 74 for gating a shape signal output from the shape detecting LUT 73 with all edge signal output from the edge detecting circuit 72 functioning as a gate signal, a coordinate detecting circuit 75 for detecting positional coordinates of the particular pattern shape and a type of the particular pattern shape, and eight line memories 76 for simultaneously transferring binary values of the eighty one pixels of the processed bi-level image Ibp to the 9×9 scanning window circuit 70.

In the above configuration of the specific shape detecting section 22, all pixels of the processed bi-level image Ibp are scanned with a 9×9 scanning window of the 9×9 scanning window circuit 70 to detect binary values of the outer pixels Po uniformly studded in the most outside layer of the circuit 70 on every other pixel, and a particular pattern shape of the wiring pattern Pw is detected according to the binary values of the outer pixels Po while referring the shape detecting LUT 73. In this case, corners of pattern shapes in the wiring pattern Pw are examined to detect the particular pattern shape. Therefore, the operation for examining corners of pattern shapes in the wiring pattern Pw is described in detail.

The inner pixels Pi ({Pi1,Pi2,Pi3,Pi4,Pi5,Pi6,Pi7,Pi8}) are scanned with a 3×3 scanning window of the 3×3 scanning window circuit 71, and binary values d1, d3, d5 and d7 of four neighboring pixels Pi1, Pi3, Pi5 and Pi7 are transferred to the edge detecting circuit 72. In the circuit 72, it is judged whether or not a remarked pixel Pi0 is placed at a contour region of a pattern shape in the wiring pattern Pw according to an equation (10).

$$Se=(\overline{d1}*\overline{d3}*\overline{d5}*\overline{d7})*(d1+d3+d5+d7) \quad (10)$$

Here a symbol Se denotes a binary value of an edge signal Sed output from the edge detecting circuit 72, a symbol * denotes a logical multiply, a symbol + denotes a logical sum, and a symbol $\overline{di}$ denotes a logical NOT of a binary value di.

In cases where the binary value Se is equal to "1", it is judged that a remarked pixel Pi0 is placed at a contour region of a pattern shape in the wiring pattern Pw. In other words, an edge of a pattern shape existing in the wiring pattern Pw is detected in the edge detecting circuit 72. Thereafter, the edge signal Sed having the binary value Se="1" is transferred to the gate circuit 74 to pass a shape signal Ssh output from the shape detecting LUT 73 through the gate circuit 74 to the coordinate detecting circuit 75. In contrast, in cases where the binary value Se is equal to "0", it is judged that a remarked pixel Pi0 is not placed at a contour region of a pattern shape in the wiring pattern Pw. In other words, an edge of a pattern shape existing in the wiring pattern Pw is not detected in the edge detecting circuit 72. Thereafter, the edge signal Sed having the binary value Se="0" is transferred to the gate circuit 74 to prevent the shape signal Ssh output from the shape detecting LUT 73 from being transferred to the coordinate detecting circuit 75.

Also, the outer pixels Po ({Po1, - - - ,Po16}) are scanned with the 9×9 scanning window W99 of the 9×9 scanning window circuit 70 at the same time that the inner pixels Pi are scanned with the 3×3 scanning window W33, and binary values Do ({Do1, - - - ,Do16}) of the outer pixels Po are transferred to the shape detecting LUT 73. In the shape detecting LUT 73, the sixteen binary values Do of the outer pixels Po are arranged in series to form a piece of square (5×5) pattern data having 16-bit length, and the square pattern data is compared with forty types of referential square (5×5) pattern data registered in the shape detecting LUT 73 in advance. Because identifying codes having 6-bit length are given to the referential square pattern data, an identifying code given to a piece of referential square pattern data agreeing with the square pattern data is output to the gate circuit 74.

FIGS. 8A to 8J show ten examples of the referential square (5×5) pattern data registered in the shape detecting LUT 73.

Figure 8A:
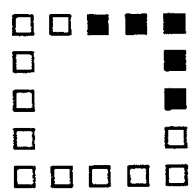
FIGS. 8A to 8J show ten examples of pieces of referential square (5×5) pattern data registered in a shape detecting LUT shown in FIG. 7.
Figure 8B:
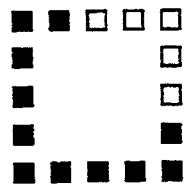
Figure 8C:
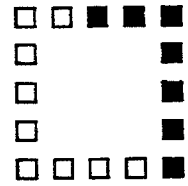
Figure 8D:
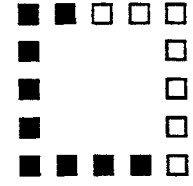
Figure 8E:
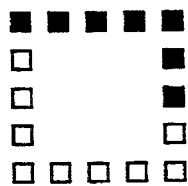
Figure 8F:
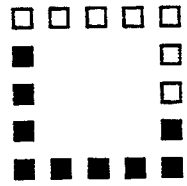
Figure 8G:
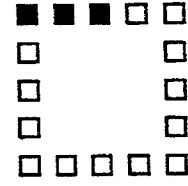
Figure 8H:
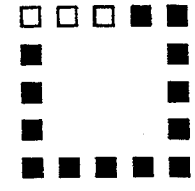
Figure 8I:
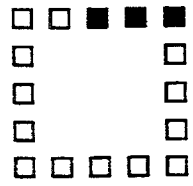
Figure 8J:
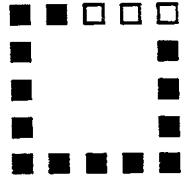

In FIG. 8A, a 90 degrees corner oriented toward the upper right is shown. Also, the referential square pattern data (not shown) corresponding to the other three 90 degrees corners oriented toward the upper left, the lower right and the lower left are registered in the shape detecting LUT 73. In FIG. 8B, a 270 degrees corner oriented toward the lower left is shown. Also, the referential square pattern data (not shown) corresponding to the other three 270 degrees corners oriented toward the upper right, the upper left and the lower right are registered in the shape detecting LUT 73. In FIG. 8C, a first type 135 degrees corner of which a right side $S_R$ is just oriented toward the upper side is shown. Also, the referential square pattern data (not shown) corresponding to the first type other three 135 degrees corners of which right sides are just oriented toward the right side, the lower side and the left side are registered in the shape detecting LUT 73. In FIG. 8D, a first type 225 degrees corner of which a left side $S_L$ is just oriented toward the upper side is shown. Also, the referential square pattern data (not shown) corresponding to the first type other three 225 degrees corners of which left sides are just oriented toward the right side, the lower side and the left side are registered in the shape detecting LUT 73. In FIG. 8E, a second type 135 degrees corner of which a left side $S_L$ is just oriented toward the right side is shown. Also, the referential square pattern data (not shown) corresponding to the second type other three 135 degrees corners of which left sides are just oriented toward the lower side, the left side and the upper side are registered in the shape detecting LUT 73. In FIG. 8F, a second type 225 degrees corner of which a right side $S_R$ is just oriented toward the right side is shown. Also, the referential square pattern data (not shown) corresponding to the second type other three 225 degrees corners of which right sides are just oriented toward the lower side, the left side and the upper side are registered in the shape detecting LUT 73. In FIG. 8G, a first type 45 degrees corner of which a left side $S_L$ is just oriented toward the upper side is shown. Also, the referential square pattern data (not shown) corresponding to the first type other three 45 degrees corners of which left sides are just oriented toward the right side, the lower side and the left side are registered in the shape detecting LUT 73. In FIG. 8H, a first type 315 degrees corner of which a right side $S_R$ is just oriented toward the upper side is shown. Also, the referential square pattern data (not shown) corresponding to the first type other three 315 degrees corners of which right sides are just oriented toward the right side, the lower side and the left side are registered in the shape detecting LUT 73. In FIG. 8I, a second type 45 degrees corner of which a right side $S_R$ is just oriented toward the upper side is shown. Also, the referential square pattern data (not shown) corresponding to the second type other three 45 degrees corners of which right sides are just oriented toward the right side, the lower side and the left side are registered in the shape detecting LUT 73. In FIG. 8J, a second type 315 degrees corner of which a left side $S_L$ is just oriented toward the upper side is shown. Also, the referential square pattern data (not shown) corresponding to the second type other three 315 degrees corners of which left sides are just oriented toward the right side, the lower side and the left side are registered in the shape detecting LUT 73.

In cases where a piece of referential square pattern data agreeing with the square pattern data is not found out in the shape detecting LUT 73, a dummy code "000000" is output to the gate circuit 74.

Thereafter, because a code output from the LUT 73 passes through the gate circuit 74 in cases where the remarked pixel Pi0 is placed at a contour region of a pattern shape in the wiring pattern Pw, the dummy code does not pass through the gate circuit 74, but an identifying code indicating a 45 degrees corner, a 90 degrees corner, a 135 degrees corner, a 225 degrees corner, a 270 degrees corner or a 315 degrees corner passes through the gate circuit 74 and is input to the coordinate detecting circuit 75.

In the circuit 75, positional coordinates of a corner indicated by the identifying code are detected, and a feature code Ic3 indicating a type of the corner and the positional coordinates of the corner is transferred to the second comparing and judging section 26. Therefore, a plurality of character codes Ic3 are transferred to the second comparing and judging section 26 in the same manner in scanning order of the printed wiring board 13.

Accordingly, a corner of a wiring pattern can be detected in the specific shape detecting section 22 to compare a feature of the corner with a referential feature of a corresponding corner of a non-defect wiring pattern in the section 26.

Also, because a corner of the wiring pattern Pw is detected with the 9×9 scanning window circuit 70 having a large mask size, a large scaled pattern such as a shield pattern or a surface mount device (SMD) pad can be selectively detected without dividing the wiring pattern Pw into a plurality of pattern regions to perform a macro-inspection of the wiring pattern Pw in the specific shape detecting section 22, and any of a narrow signal line, pin hole or a remaining copper of the wiring pattern Pw pertaining to a micro-inspection is not detected.

Also, a wide width type large scaled short point undesirably occurring in the wiring pattern Pw can be detected as a corner of the wiring pattern Pw in the specific shape detecting section 22. In addition, in cases where the specific shape detecting section 22 is provided to mainly detect the wide width type large scaled short point, it is applicable that a size of the processed bi-level image Ibp be reduced to make the shape detecting LUT 73 small.

Next, the first comparing and judging section 25 is described.

In the section 25, the feature information Ic1 transferred from the through hole detecting section 15 and the feature information Ic2 transferred from the design rule checking section 21 are compared with pieces of referential feature information Ir1 stored in the feature information storing section 23. The referential feature information Ir1 are determined by learning a non-defective printed wiring board. Thereafter, one or more pieces of feature information Ic2 differing from the referential feature information Ir1 are judged as one or more pieces of defect information respectively indicating a type of a defect and a position of the defect.

Figure 9A:
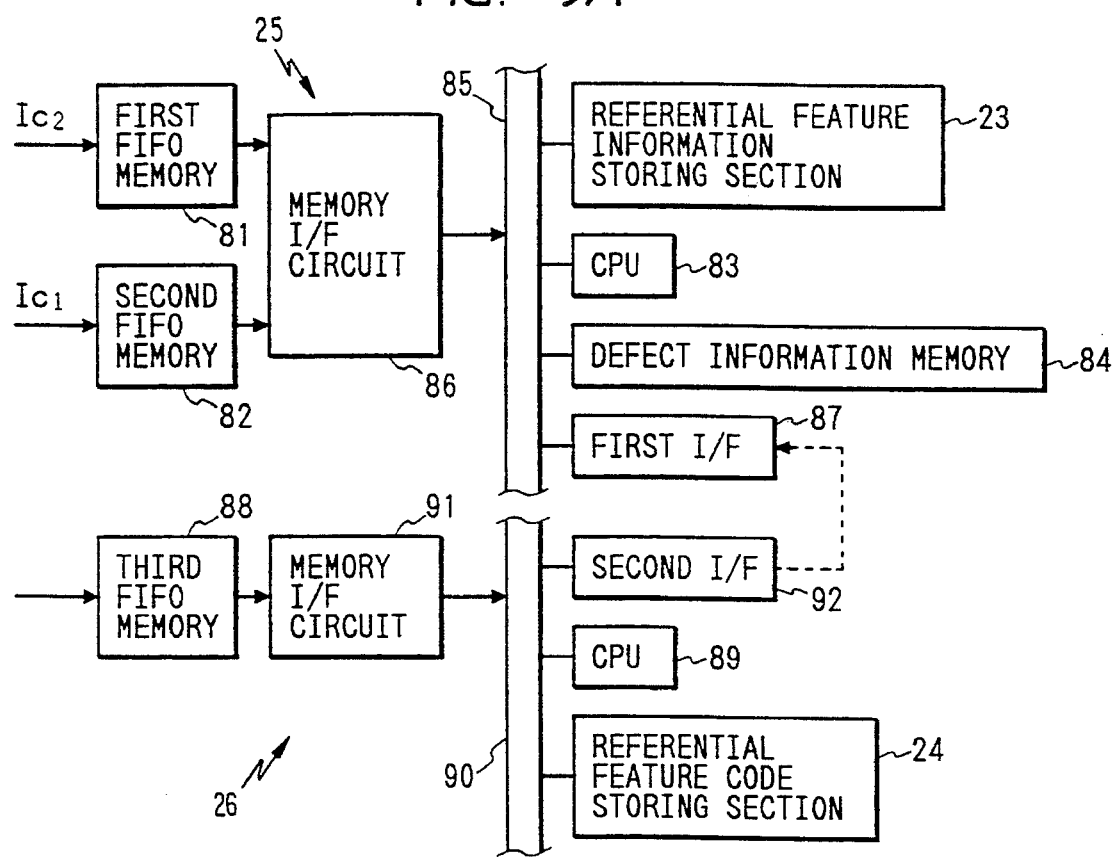
FIG. 9A is a block diagram of first and second comparing and judging sections shown in FIG. 1.

FIG. 9A is a block diagram of the first and second comparing and judging sections 25, 26.

As shown in FIG. 9A, the first comparing and judging section 25 comprises a first first-in first-out (FIFO) memory 81 for buffering the feature information Ic2 transferred from the design rule checking section 21, a second first-in first-out (FIFO) memory 82 for buffering the feature information Ic1 transferred from the through hole detecting section 15, a central processing unit (CPU) 83 for comparing the feature information Ic2 with the referential feature information Ir1 and judging the feature information Ic buffered in the FIFO memory 82 and one or more pieces of feature information Ic2 differing from the referential feature information Ir1 as one or more pieces of defect information respectively indicating a type of a defect and a position of the defect, a defect information memory 84 for storing the defect information judged in the CPU 83, a data bus 85 for transferring the information Ic1, Ic2 and Ir1, a memory interface (I/F) circuit 86 for connecting the FIFO memories 81, 82 with the data bus 85, and a first interface (I/F) 87 for connecting the first comparing and judging section 25 with the second comparing and judging section 26.

In the above configuration, the operation performed in the first comparing and judging section 25 is described.

The feature information Ic2 are buffered in the FIFO memory 81 in scanning order of the printed wiring board 13, and the feature information Ic1 are buffered in the FIFO memory 82. Thereafter, the feature information Ic1, Ic2 are fetched in the CPU 83. Also, the referential feature information Ir1 stored in scanning order of a non-defect printed wiring board in the feature information storing section 23 are fetched in the CPU 83. Thereafter, the feature information Ic2 are compared with the referential feature information Ir1 in the CPU 83. In cases where a piece of feature information Ic2 differs from the referential feature information Ir1, the feature information Ic2 is judged as a piece of defect information in the CP 83, and the defect information is stored in the defect information memory 84 under the control of the CPU 83. Therefore, one or more pieces of feature information Ic2 indicating types of defects and positions of the defects can be stored as pieces of defect information in the defect information memory 84.

In contrast, because each of the characteristic information Ic1 denotes pieces of defect information, the feature information Ic1 are stored in the defect information memory 84 as the defect information under the control of the CPU 83.

An example of the operation performed in the first comparing and judging section 25 is described with reference to FIG. 9B.

Figure 9B:
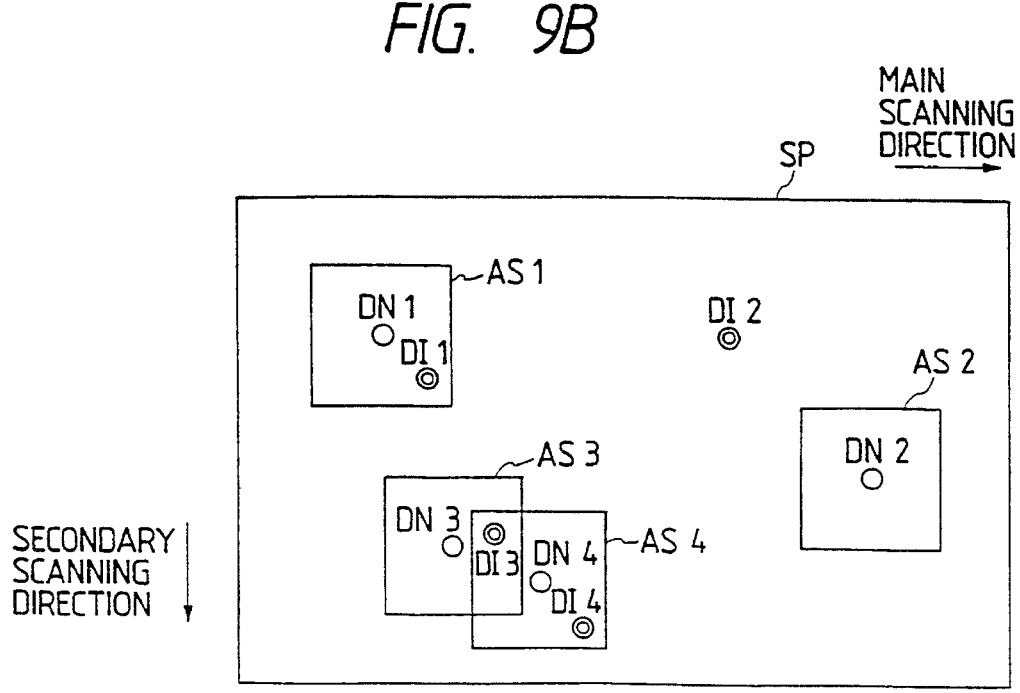
FIG. 9B shows an example of the operation performed in the first comparing and judging section.

FIG. 9B shows an example of positions indicated by the feature information Ic2 and the referential feature information Ir1 in a two-dimensional space. Positions illustrated by circles in a two-dimensional space SP denote the referential feature information Ir1 called pieces of non-defect data DNi (i=1 to 4), and positions illustrated by double circles in the two-dimensional Space SP denote the feature information Ic2 called pieces of inspected data DIi.

In the example shown in FIG. 9B, a positional difference between a piece of inspected data DIi and a piece of non-defect data DNi is allowed on condition that the positional difference is equal to or lower than a total width Wp of p (in number) pixels. In detail, square areas ASi respectively having four sides of 2*Wp length are defined to set the non-defect data DNi in the centers of the square areas ASi in the CPU 83, and it is judged in the CPU 83 that the inspected data DIi are respectively placed in one of the square areas ASi. Because the inspected data DI1, DI3 and DI4 are respectively placed in one of the square areas ASi, AS3 and AS4, the inspected data DI1 is judged to accord with the non-defect data DN1, the inspected data DI3 is judged to accord with the non-defect data DN3, and the inspected data DI4 is judged to accord with the non-defect data DN4. Therefore, it is judged that the inspected data DI1, DI3 and DI4 are not respectively a piece of defect information, and the feature information Ic2 pertaining to the inspected data DI1, DI3 and DI4 are not stored in the defect information memory 84. In contrast, because the inspected data DI2 is not placed in any square area, the inspected data DI2 is judged to differ from any of the non-defect data DNi. Therefore, the inspected data DI2 is judged to be a piece of defect information and is stored in the defect information memory 84. In addition, in cases where a piece of inspected data DIa is placed in a plurality of square areas in which feature types of pieces of non-defect data are the same as that of the inspected data DIa, a non-defect data DNs nearest to the inspected data in the two-dimensional space SP is selected, and it is judged that the inspected data DIa accords with the non-defect data DNs. Therefore, though the inspected data DI3 is placed in the square areas AS3, AS4, the inspected data DI3 is judged to accord with the non-defect data DN3 because the inspected data DI3 is nearer to the non-defect data DN3 than the non-defect data DN4.

Thereafter, the feature information Ic1, Ic2 stored in the defect information memory 84 are reported to an operator as the defect information.

Accordingly, the feature information Ic1 detected in the through hole filling section 15 can be reliably reported. Also, the defect information can be reliably selected from the feature information Ic2 detected in the design rule detecting section 21 as a result of the micro-inspection. Therefore, results of the micro-inspection can be reliably reported.

Next, the second comparing and judging section 26 is described.

In the section 26, the feature code Ic3 transferred from the specific shape detecting section 22 are compared with pieces of referential feature code Ir2 stored in the feature code storing section 24. The referential feature code Ir2 are determined by learning a non-defective printed wiring board. Thereafter, one or more pieces of feature code Ic3 differing from the referential feature code Ir2 are judged as one or more pieces of defects and are output.

As shown in FIG. 9A, the second comparing and judging section 26 comprises a third first-in first-out (FIFO) memory 88 for buffering the feature code Ic3 transferred from the specific shape detecting section 22, a central processing unit (CPU) 89 for comparing the feature code Ic3 with the referential feature code Ir2 stored in the feature code storing section 24 and judging one or more feature code Ic3 differing from the referential feature code Ir2 as one or more pieces of defect information denoting defects at corners of the wiring pattern Pw, a data bus 90 for transferring the information code Ic3 and Ir2, a memory interface (I/F) circuit 91 for connecting the FIFO memory 88 with the data bus 90, and a first interface (I/F) 92 for connecting the second comparing and judging section 26 with the first comparing and judging section 25 to transfer the feature code Ic3 judged as the defect information to the defect information memory 84.

In the above configuration, the feature code Ic3 are buffered in the third FIFO memory 88 a ad are fetched in the CPU 89. Also, the referential feature code Ir2 are fetched in the CPU 89. Thereafter, the feature code Ic3 and the referential feature code Ir2 are compared in the same manner as in the first comparing and judging section 25, and one or more feature code Ic3 differing from the referential feature code Ir2 are judged as one or more pierces of defect information. Thereafter, the defective information are stored in the defect information memory 84 and are reported to the operator.

In this embodiment, a CPU system of the first comparing and judging section 25 differs from that of the second comparing and judging section 26. However, it is applicable that the first and second comparing and judging sections 25, 26 comprise the same CPU system having a multi-task function. In this case, a first task for the first comparing and judging section 25 and a second task for the second comparing and judging section 26 are changed over to perform the first and second tasks in series.

Accordingly, the defect information can be reliably selected from the feature codes Ic3 detected in the specific shape detecting section 22 as a result of the macro-inspection of the wiring pattern Pw, and the defect information pertaining to the macro-inspection can be reliably reported.

Also, because the sections 21, 23 and 25 pertaining to the micro-inspection are arranged in the wiring pattern inspection apparatus 11 in parallel to the sections 22, 24 and 26 pertaining to the macro-inspection, the micro-inspection and the macro-inspection of the wiring pattern Pw can be performed in parallel. In other words, various types of defects existing in the printed wiring board 12 can be strictly detected with a high accuracy without overlooking any defect regardless of whether the defects are large sized defects detected by the macro-inspection or small sized defects detected by the micro-inspection.

Next, a second embodiment of a wiring pattern detecting apparatus according to the present invention is described with reference to FIGS. 10 to 14.

Figure 10:
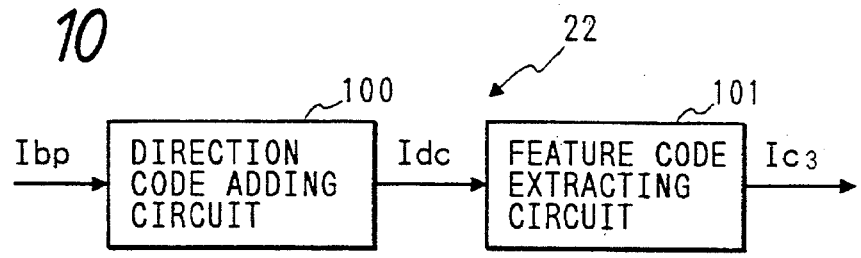
FIG. 10 is a constitutional block diagram of the specific shape detecting section in a wiring pattern detecting apparatus according to a second embodiment of the present invention.

FIG. 10 is a constitutional block diagram of the specific shape detecting section 22 in a wiring pattern detecting apparatus according to a second embodiment of the present invention.

As shown in FIG. 10, the specific shape detecting section 22 comprises a direction code adding circuit 100 for adding one of eight types direction codes respectively indicating an edge direction of the wiring pattern Pw to each of contour pixels of the wiring pattern Pw in the processed bi-level image Ibp produced in the through hole filling section 15, and a feature code extracting circuit 101 for extracting one or more corner codes, which each are produced from a pair of different types direction codes added to a pair of contour pixels adjacent to each other, to indicate one or more corners of the wiring pattern Pw existing in one or more feature points placed in one ore more contour areas of the wiring pattern Pw and outputting the corner codes and positional coordinates of the feature points as feature codes Ic3 in synchronization with synchronizing signals Ss. Each of the corner codes are produced from two direction codes of the contour pixels adjacent to each other, and the direction codes differ from each other to define each of the corner codes as a code indicating a change of the direction codes.

In the above configuration of the specific shape detecting section 22, to put it briefly, a direction code is added to each of the contour pixels of the wiring pattern Pw, and changes of the direction codes detected. Therefore, corners of the wiring pattern Pw placed in the pixels pertaining to the changes of the direction codes are detected as specific shapes of the wiring pattern Pw. As a method for adding the direction codes, a chain code of Freeman (H. Freeman: "On the Encoding of Arbitrary geometric Configurations" IRE Trans. Electron. Comput. EC-10, pp.260–268 (1961)) is well-known.

Figure 11A:
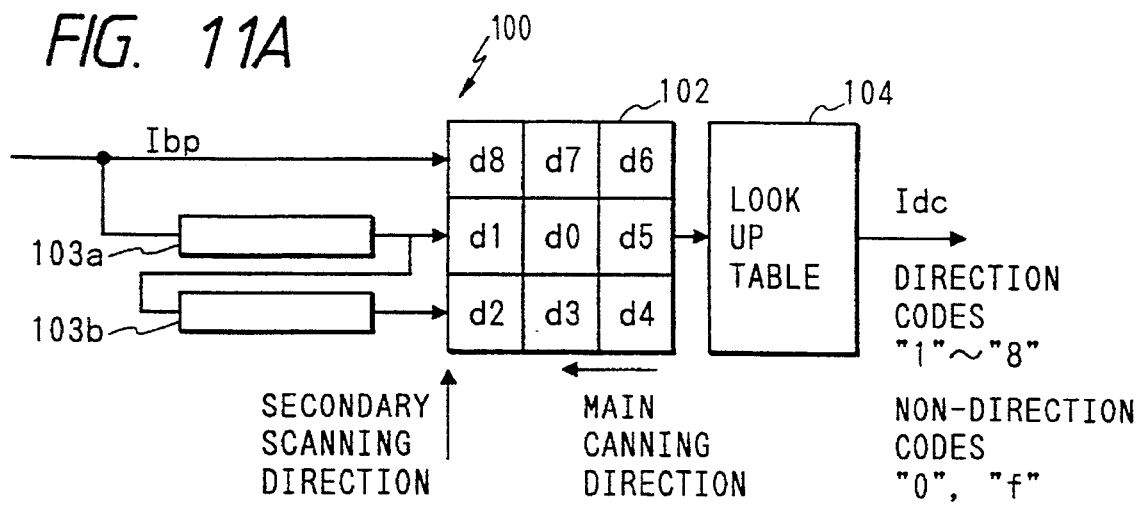
FIG. 11A is a constitutional circuit and block diagram of a direction code adding circuit shown in FIG. 10.
Figure 11B:
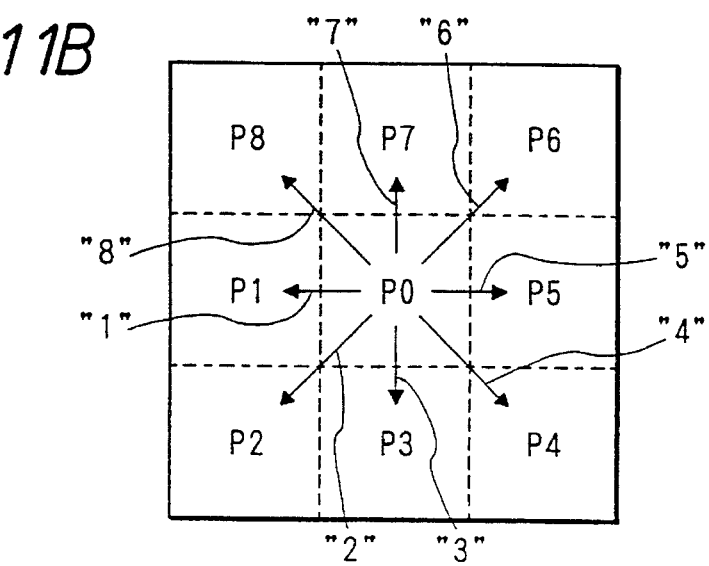
FIG. 11B shows eight types direction codes respectively indicating an edge direction of the wiring pattern in each of contour pixels of the wiring pattern.

FIG. 11A is a constitutional circuit and block diagram of the direction code adding circuit 100. FIG. 11B shows eight types direction codes respectively indicating an edge direction of the wiring pattern Pw in each of contour pixels of the wiring pattern Pw.

As shown in FIG. 11A, the direction code adding circuit 100 comprises a 3×3 scanning window circuit 102 for scanning nine (3×3) pixels P0 to P8 of the processed bi-level image Ibp with a 3×3 scanning window, a first line memory 103a for temporarily storing binary values of the pixels P0,P1 and P5, a second line memory 103b for temporarily storing binary values of the pixels P2,P3 and P4, and a look up table (LUT) 104 for outputting a direction code according to a bit pattern which is formed of nine binary values of the pixels P0 to P8 scanned with the 3×3 scanning window to produce a direction code image from the processed bi-level image Ibp. As shown in FIG. 11B, eight types vectors extending from a starting point placed at the remarked pixel P0 to the neighboring pixels P1 to P8 are defined. In this case, a direction of the vector extending to the pixel P1 is indicated by a direction code "1", a direction of the vector extending to the pixel P2 is indicated by a direction code "2", a direction of the vector extending to the pixel P3 is indicated by a direction code "3", a direction of the vector extending to the pixel P4 is indicated by a direction code "4", a direction of the vector extending to the pixel P5 is indicated by a direction code "5", a direction of the vector extending to the pixel P6 is indicated by a direction code "6", a direction of the vector extending to the pixel P7 is indicated by a direction code "7", and a direction of the vector extending to the pixel P8 is indicated by a direction code "8". The direction codes are respectively expressed by a piece of 4-bit length data.

In the above configuration of the direction code adding circuit 100, a contour area of the wiring pattern Pw in the processed bi-level image Ibp is scanned with the 3×3 scanning window in the 3×3 scanning window circuit 102 in a clockwise direction while placing a remarked pixel P0 at one of the contour pixels, and a direction code is output from the LUT 104 and is added to the remarked pixel P0 each time the remarked pixel P0 and the neighboring pixels P1 to P8 placed in the contour area are scanned. In detail, in cases where an equation (11) is satisfied, it is regarded that one of the contour pixels of the wiring pattern Pw is scanned as the remarked pixel P0.

$$d0*(\overline{d1*d3*d5*d7}) = 1, \sum_{i=1}^{8} di > 1, \quad (11)$$

$$Nc(8) = 1, \text{ and } Nc(4) = 1$$

Here symbols d0,d1,d3, d5 and d7 denote binary values of the pixel P0,P1,P3,P5 and P7, a symbol * denotes a logical multiply, and a symbol $\overline{di}$ denotes a logical NOT of a binary value di. A symbol Nc(8) is called an eight-connective number and is well-known as a parameter indicating a connection of a pattern. Also, a symbol Nc(4) is called a four-connective number and is well-known as a parameter indicating a connection of a pattern.

$$Nc(8) = \sum_{i \in S1} \{\overline{di} - (\overline{di*\overline{d_{i+1}}*\overline{d_{i+2}}})\},$$

$$Nc(4) = \sum_{i \in S1} \{di - (di*d_{i+1}*d_{i+2})\}$$

$$S1 = \{1,3,5,7\}, d_{7+2} = d1$$

Therefore, a direction code "N" added to the remarked pixel P0 is found out in the LUT 104 t0 satisfy an equation (12) on condition that the equation (11) is satisfied.

$$d_N*\overline{d_{N+1}}=1 \ (N=1,2,---,\text{or } 8), \text{ and } d9=d1 \quad (12)$$

Also, there is a specific wiring pattern having one pixel width for which the equation (11) is meaningless. Therefore, in cases where the specific wiring pattern satisfies an equation (13), a non-direction code "A" ("A" is not a number) is added to pixels of the specific wiring pattern.

$$d0*(\overline{d1*d3*d5*d7}) = 1 \text{ and } \sum_{i=1}^{8} di = 1, \text{ or} \quad (13)$$

$$Nc(8) \neq 1 \text{ or } Nc \times (4) \neq 1$$

Also, a non-direction code "f" ("f" if is not a number) is automatically added to pixels which are not the contour pixels but are placed inside the wiring pattern Pw, and a non-direction code "0" is automatically added to the base side pixels of the base side area Ab.

Figure 12:
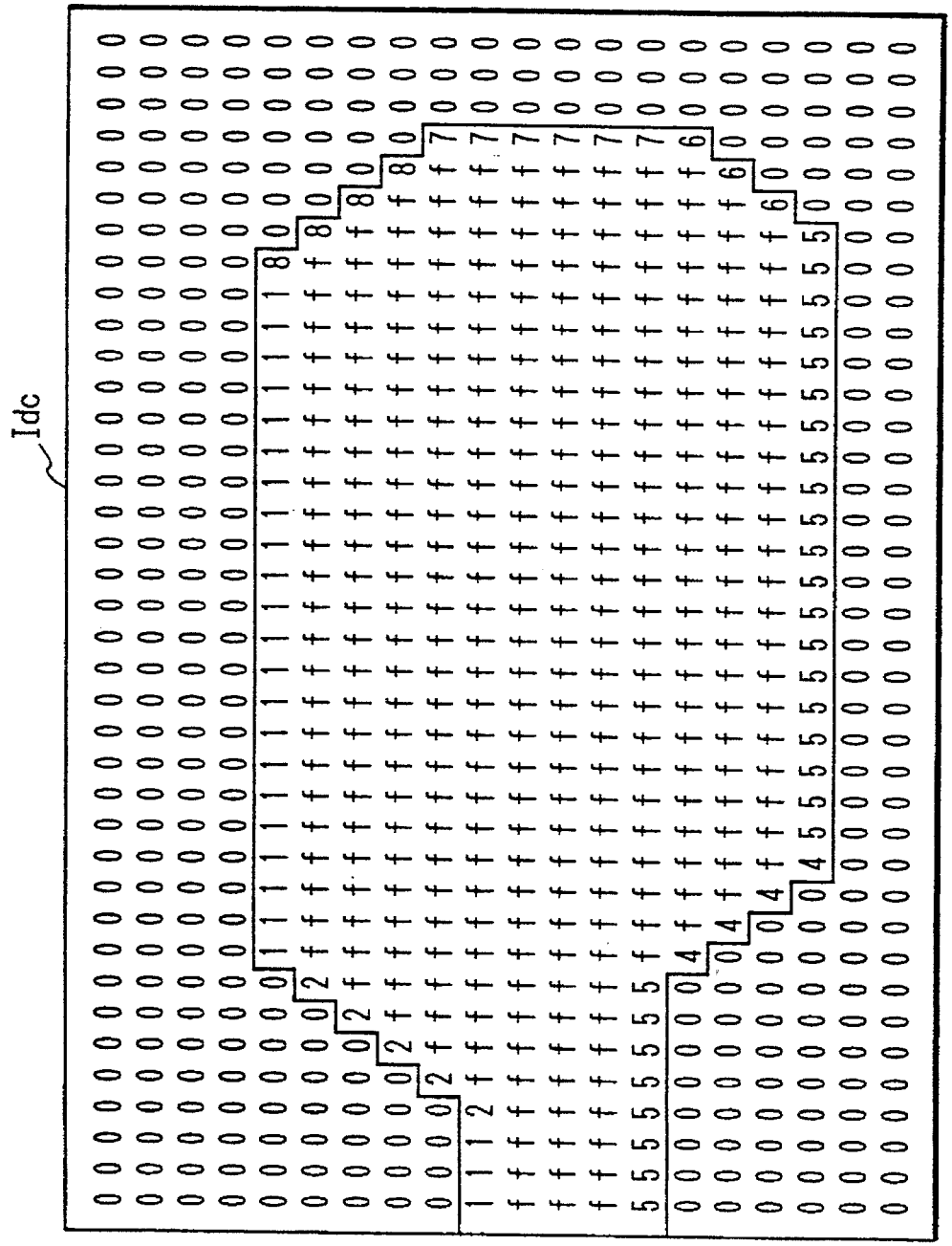
FIG. 12 shows an example of a direction code image Idc produced in a direction code adding circuit shown in FIG. 10.

As a result, as shown in FIG. 12, a direction code image Idc in which the direction codes "1" to "8" and the non-direction code "f" are given to the conducting side pixels placed in the wiring pattern Pw is obtained in the direction code adding circuit 100.

Figure 13:
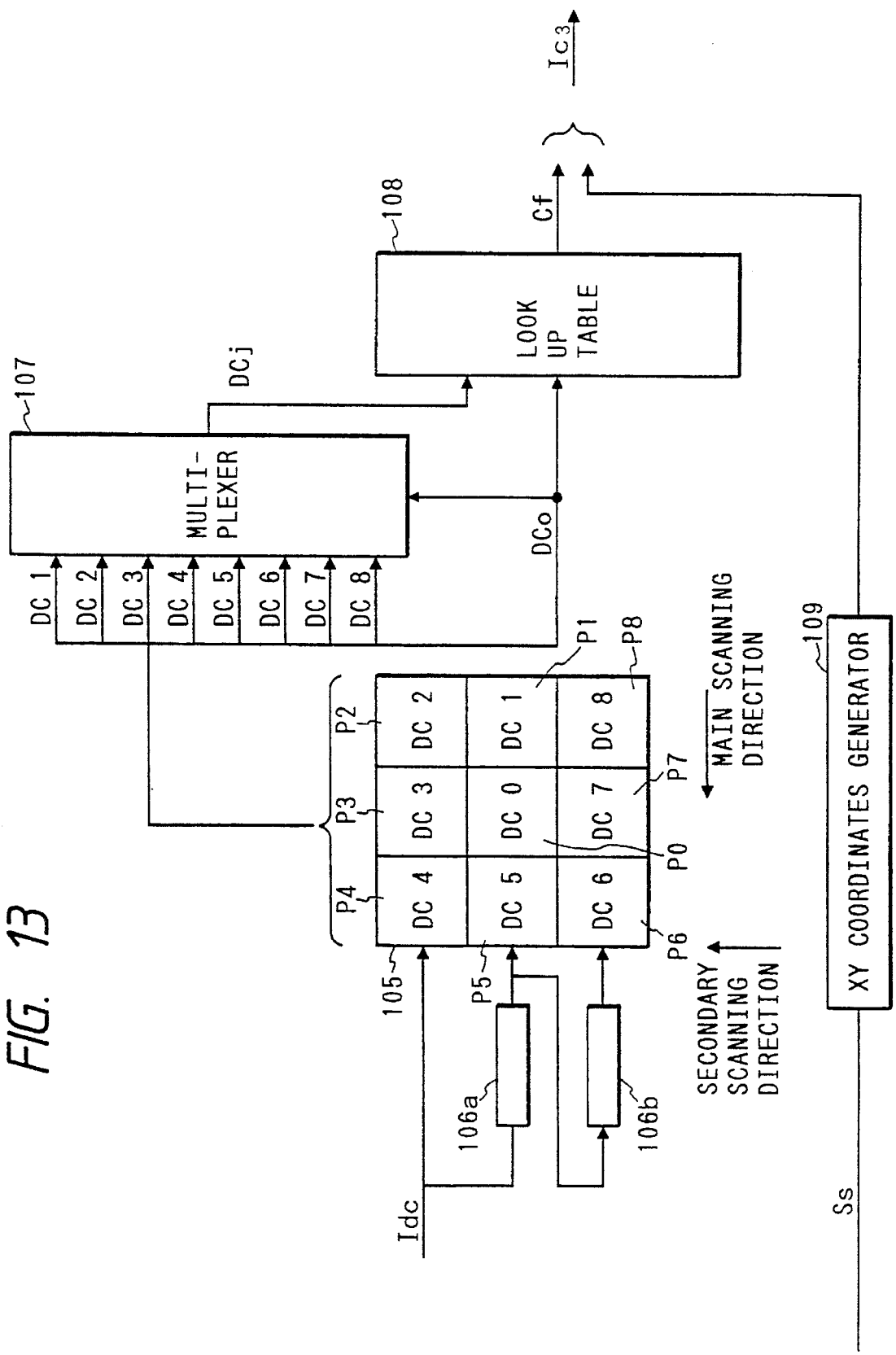
FIG. 13 is a constitutional circuit and block diagram of a feature code producing circuit shown in FIG. 10.

FIG. 13 is a constitutional circuit and block diagram of the feature code extracting circuit 101.

As shown in FIG. 13, the feature code extracting circuit 101 comprises a 3×3 scanning window circuit 105 for scanning nine (3×3) pixels P0 to P8 of the direction code image Idc with a 3×3 scanning window, a first line memory 106a for temporarily storing direction codes DC0,DC1 and DC5 of the pixels P0,P1 and P5, a second line memory 106b for temporarily storing direction codes DC2,DC3 and DC4 of the pixels P2,P3 and P4, a multiplexer 107 for selecting a direction code of a neighboring pixel P1,P2, - - - ,or P8 transferred from the 3×3 scanning window circuit 105 according to a direction code DC0 of a remarked pixel P0 transferred from the 3×3 scanning window circuit 105, a look up table (LUT) 108 for outputting a corner code indicating the existence of a corner of the wiring pattern Pw at a feature point placed in a contour pixel of the wiring pattern Pw with reference to the direction code DC0 of the remarked pixel P0 and a selected direction code of a neighboring pixel selected in the multiplexer 107, and an XY coordinates generator 109 for generating positional (or XY) coordinates in synchronization with a synchronizing signal Ss to form a feature code Ic3 composed of the corner code output from the LUT 108 and the positional coordinates.

In the above configuration of the feature code extracting circuit 101, the pixels of the direction code image Idc produced in the direction code adding circuit 100 are scanned pixel by pixel with the 3×3 scanning window in the 3×3 scanning window circuit 105. In this case, a remarked pixel P0 placed in the center of the 3×3 scanning window accords with one of contour pixels of the wiring pattern Pw. Thereafter, direction codes of the neighboring pixels P1,P2, - - - , and P8 are transferred to the multiplexer 107. Also, a direction code DC0="j" (j=1,2, - - - , or 8) of the remarked pixel P0 which corresponds to a vector directed to the neighboring pixel Pj is transferred to the multiplexer 107 and the LUT 108. In the multiplexer 107, a direction code DCj of a neighboring pixel Pj indicated by the direction code "j" of the remarked pixel P0 is selected and output to the LUT 108. In this case, the direction code DCj is expressed by "1", "2", "3","4", "5", "6", "7" or "8". In the LUT 108, a corner code Cf(j,DCj) indicating the change from the direction code "j" of the remarked pixel P0 to the direction code DCj of the neighboring pixel Pj is selected and output. That is, various corner codes Cf(DC0,DCi) calculated according to an equation (14) in advance are registered in the LUT 108.

$$Cf(Dc0, DCi) = DC0 \times 16 + DCi \qquad (14)$$
$$= \text{``}DC0,DCi\text{''}$$

Here a neighboring pixel Pi having the direction code DCi is indicated by a vector corresponding to the direction code DC0 of the remarked pixel P0. Also, a multiplier "16" denotes to shift the direction code "DC0" to the left side by 4 bits. That is, each of the corner codes Cf(DC0,DCi) has an 8-bit length. The direction code "DC0" is placed at upper 4 bits of the corner code Cf(DC0,DCi), and the direction code "DCi" is placed at lower 4 bits of the corner code Cf(DC0, DCi).

In this case, the corner codes Cf(DC0,DCi) in which the direction codes DC0 and DCi differ from each other are registered in the LUT 108. Therefore, in cases where the direction codes DC0 and DCi input to the LUT 108 are the same, any corner code is not output from the LUT 108.

In FIGS. 14A to 14H, examples of corners indicated by the corner codes Cf(DC0,DCi) are shown. In case of Cf(DC0,DCi)="1,2" shown in FIG. 14A, a 135 degrees corner of which a right side $S_R$ is just oriented toward the right side is indicated. In case of Cf(DC0,DCi)="2,1" shown in FIG. 14B, a 225 degrees corner of which a left side $S_L$ is just oriented toward the right side is indicated. In case of Cfi(DC0,DCi)="1,8" shown in FIG. 14C, a 225 degrees corner of which a right side $S_R$ is just oriented toward the right side is indicated. In case of Cf(DC0,DCi)="8,7" shown in FIG. 14D, a 225 degrees corner of which a left side $S_L$ is just oriented toward the lower side is indicated. In case of Cf(DC0,Ddi)="7,6" shown in FIG. 14E, a 225 degrees corner of which a right side $S_R$ is just oriented toward the lower side is indicated. In case of Cf(DC0,DCi)="6,5" shown in FIG. 14F, a 225 degrees corner of which a left side $S_L$ is just oriented toward the left side is indicated. In case of Cf(DC0,DCi)="5,4" shown in FIG. 14G, a 225 degrees corner of which a right side $S_R$ is just oriented toward the left side is indicated. In case of Cf(DC0,DCi)="4,5" shown in FIG. 14H, a 135 degrees corner of which a left side $S_L$ is just oriented toward the left side is indicated.

In cases where the direction code DCj of the neighboring pixel Pj selected in the multiplexer 107 is "A", a corner code "A" is output from the LUT 108.

Thereafter, a piece of feature code Ic3 which is composed of the corner code Cf(j,DCj) or "A" of a feature point and positional (or XY) coordinates of the feature point generated in the XY coordinates generator 109 is output to the second comparing and judging section 26. Thereafter, pieces of defect information are reported in the same manner as in the first embodiment.

Accordingly, a plurality of feature codes Ic3 indicating characteristics of corners of the wiring pattern Pw can be produced in the direction code adding circuit 100 and the feature code extracting circuit 101 of the specific shape detecting section 22 by scanning each of the contour pixels of the wiring pattern Pw as the remarked pixel Po.

Also, because a direction code is added to the contour pixels of the wiring pattern Pw pixel by pixel in the direction code adding circuit 100, not only a wide wiring pattern but also a remaining copper or a pin hole can be detected with a high accuracy. Therefore, the detection of the remaining copper, the pin hole and the like can be enhanced as compared with that in the first embodiment.

In the second embodiment, the contour area of the wiring pattern Pw in the processed bi-level image Ibp is scanned in the clockwise direction while placing the remarked pixel P0 at one of the contour pixels. However, it is applicable that the contour area of the wiring pattern Pw is scanned in the counterclockwise direction.

Also, a 135 degrees corner or a 225 degrees corner is indicated by the corner code Cf="1,2" or "1,8". However, it is difficult to stably detect a 90 degrees corner indicated by a corner code Cf="1,3" or a 315 degrees corner indicated by a corner code Cf="1,6". In this case, it is preferred that the processed bi-level image Ibp be filtered with a bi-level filter to round off an acute angle. Also, it is preferred that a corner code Cf indicating an acute angle be changed to a series of corner codes Cf respectively indicating a 135 degrees corner or a 225 degrees corner, prior to the operation in the second comparing and judging section 26. For example, the corner code Cf="1,3" is changed to corner codes "1,2" and "2,3", and the corner code Cf="1,6" is changed to corner codes "1,8", "8," and "7,6". In this case, positional coordinates for the corner codes "1,2" and "2,3" are the same those for the corner code "1,3", and positional coordinates for the corner codes "1,8", "8,7" and "7,6" are the same those for the corner code "1,6".

Next, a third embodiment of a wiring pattern detecting apparatus according to the present invention is described with reference to FIGS. 15 to 19.

In the third embodiment, comparing and judging operations performed in the second comparing and judging section 26 are described. In this case, a plurality of feature codes Ic3 which each are composed of the corner bode Cf(j,DCj) of a feature point and positional coordinate of the feature point are produced in the specific shape detecting section 22 according to the second embodiment and are transferred to the second comparing and judging section 26. The configuration of the second comparing and judging section 26 according to the third embodiment is the same as that shown in FIG. 9A. Therefore, comparing and judging operations differing from those in the first embodiment are described in the third embodiment.

Figure 15A:
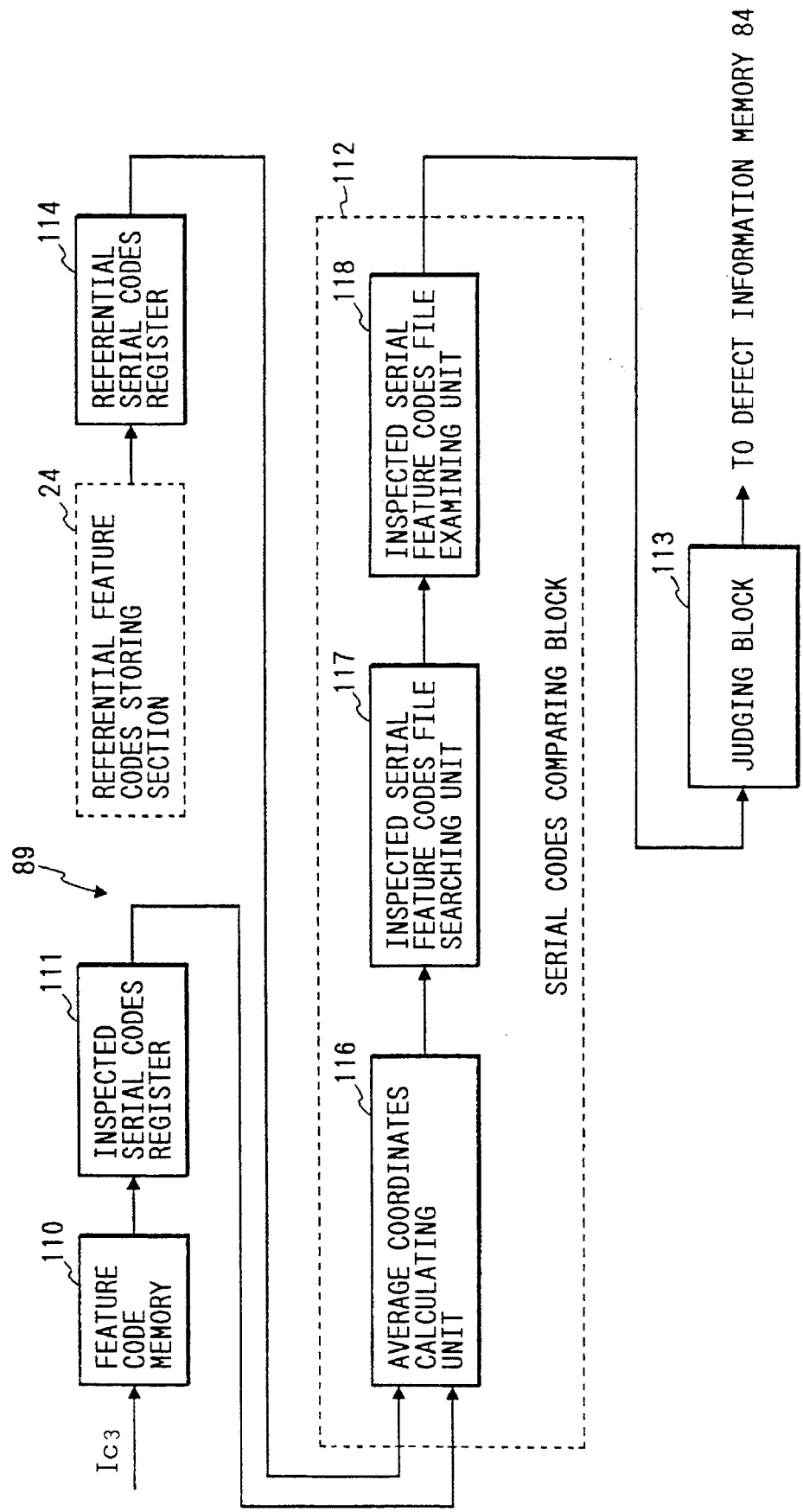
FIG. 15A is a constitutional block diagram of the CPU shown in FIG. 9A according to a third embodiment of the present invention.

FIG. 15A is a constitutional block diagram of the CPU 89 shown in FIG. 9A according to the third embodiment of the present invention.

As shown in FIG. 15A, the CPU 89 of the second comparing and judging means 26 comprises a feature code memory 110 for storing a plurality of feature code Ic3 produced in the specific shape detecting section 22, an inspected serial codes register 111 for registering a series of feature codes produced by serially connecting a plurality of feature codes Ic3 in which each of pairs of feature codes Ic3 adjacent to each other is placed within a prescribed allowable distance in an XY plane, a referenctial serial codes register 114 for registering a series of referential feature codes produced by serially connecting a plurality of referential feature code Ir2 of the non-defective printed wiring board stored in the feature code storing section 24, a serial codes comparing block 112 for comparing the series of feature codes registered in the register 111 with the series of referential feature codes registered in the register 114, and a judging block 113 for judging whether or not the wiring pattern Pw is defective or non-defective according to a compared result obtained in the serial codes comparing block 112.

The serial codes comparing block 112 comprises an average coordinates calculating unit 116 for calculating average coordinates of the series of referential feature codes to set a referential allowable limit having its center placed at the average coordinates, an inspected serial feature codes file searching unit 117 for searching an inspected serial feature codes file of the inspected serial codes register 111 for a series of feature codes of which average coordinates are placed in the referential allowable limit, and an inspected serial feature codes file examining unit 118 for examining whether or not a series of corner codes of the series of feature code found out in the searching unit 117 agrees with a series of referential corner codes of the series of referential feature codes to judge the wiring pattern Pw defective in the judging block 113 in cases where the series of corner codes does not agree with the series of referential corned codes.

In the above configuration of the CPU 89, a concept of the serialization of a plurality of feature codes Ic3 performed in the inspected serial codes register 111 is described with reference to FIGS. 15B to 15D.

Figure 15B:
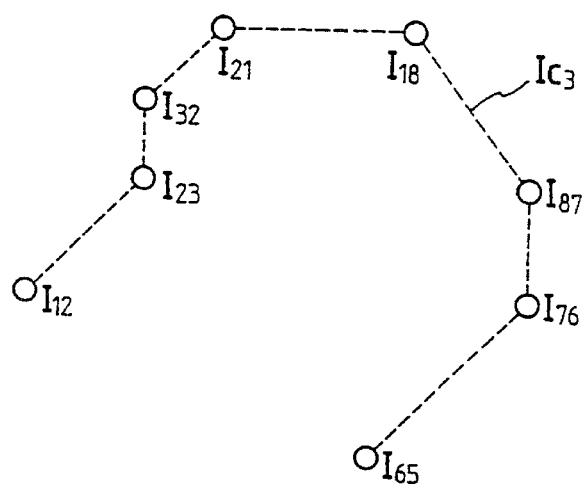
FIG. 15B shows an example of a series of feature codes.
Figure 15C:
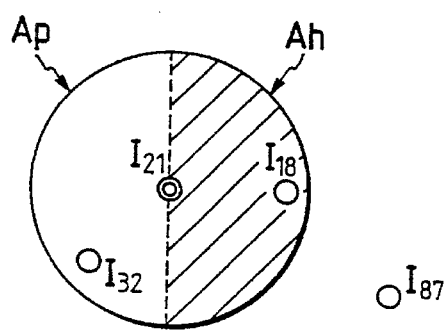
FIG. 15C shows the procedure for serially connecting a plurality of feature codes.

FIG. 15B shows an example of a series of feature codes Ic3. FIG. 15C shows the procedure for serially connecting a plurality of feature codes Ic3. FIG. 15D shows a series of feature codes Ic3 registered in a serial codes register.

As shown in FIG. 15B, eight feature codes Ic3 in which a corner code "1,2" of a starting point Ps, corner codes "2,3" and "3,2", a remarked corner code "2,1", corner codes "1,8", "8,7" and "7,6" and a corner code "6,5" of an ending point Pe are connected in that order. In the third embodiment, a feature code having a corner code "X,Y" is called a feature code $I_{XY}$. Also, as shown in FIG. 15C, a prescribed allowable limit Ap having a remarked feature code I21 at the center is initially set, and the allowable limit Ap is searched for a feature code to be connected to the remarked feature code I21.

For example, in cases where a feature code placed in the right direction to the remarked feature code I21 is planned to be connected, a feature code placed in an upper right direction or in a lower right direction is allowed to be connected with the remarked feature code I21. Therefore, the allowable limit Ap is searched for a feature code I12 or I18 corresponding to the remarked feature Code I21, and the feature code I18 is connected with the remarked feature code I21. Thereafter, the feature code I18 is treated as a remarked feature code, and a prescribed allowable limit Ap newly defined is searched for a feature code I87 corresponding to the remarked feature code I18. This searching operation is continued until any feature code connected to be a remarked feature code is not found in a prescribed allowable limit Ap. When the searching operation is finished, positional coordinates of a remarked feature code finally defined is regarded as the ending point Pe. Also the allowable limit Ap is searched for a feature code placed in the left direction to the remarked feature code I21 in the Same manner. That is, the allowable limit Ap is searched for a feature code I12 or I32 corresponding to the remarked feature code I21, and the feature code I32 is connected with the remarked feature code I21. Thereafter, the searching operation is continued until any feature code connected to be a remarked feature code newly defined is not found in a prescribed allowable limit Ap newly defined. When the searching operation is finished, positional coordinates of a remarked feature code finally defined is regarded as the starting point Ps. In the above searching operations, a searching area in a allowable limit Ap can be limitedly determined according to a corner code Cf(DC0,DCi) of a remarked feature code. For example, the allowable limit Ap is searched for a feature code which is planned to be connected to a remarked feature code I21 and is placed in the right direction to the remarked feature code I21, a searching area can be limited to a right half area Ah of the allowable limit Ap.

Figure 15D:
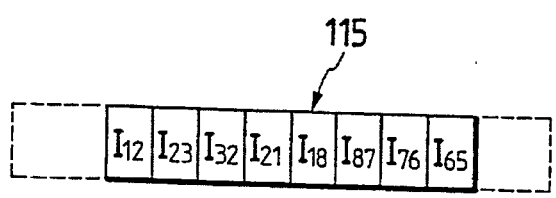
FIG. 15D shows a series of feature codes registered in a serial codes register.

Also, as shown in FIG. 15D, a serial codes register 115 is prepared in the inspected serial codes register 111, and the remarked feature code I21 initially set is registered in a central position of the serial codes register 115. Thereafter, a plurality of feature codes are registered one after another while connecting each of the feature codes with a feature code already registered in the serial codes register 115. Therefore, a series of feature codes Ic3 can be easily produced.

Next, a procedure for serially connecting a plurality of feature codes Ic3 in the inspected serial codes file 111 is described in detail with reference to FIG. 16.

Figure 16:
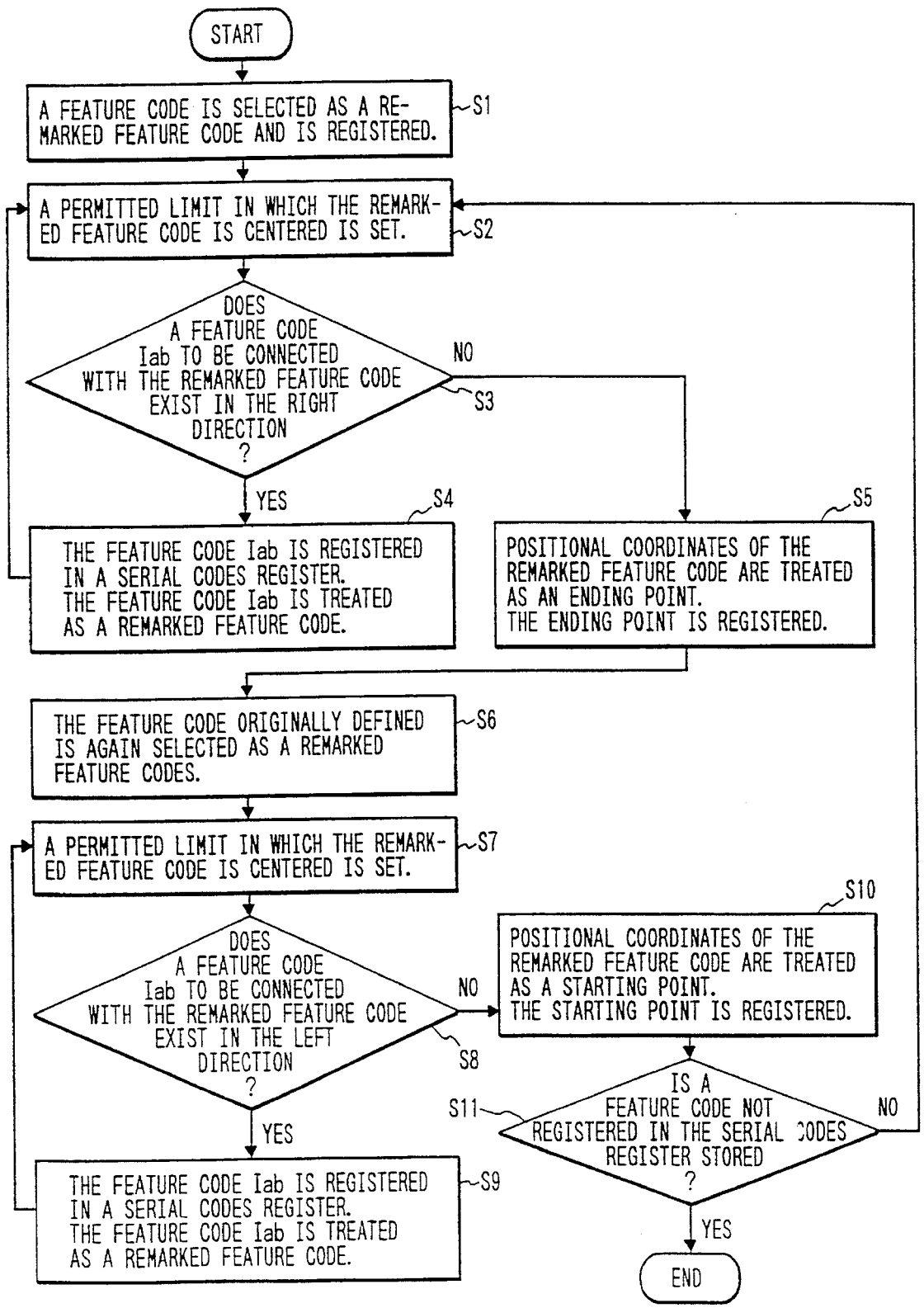
FIG. 16 is a flow chart showing a procedure of the serialization of a plurality of feature codes performed in an inspected serial codes register shown in FIG. 15A.

FIG. 16 is a flow chart showing a procedure of the serialization of a plurality of feature codes Ic3 performed in the inspected serial codes register 111;

As shown in FIG. 16, in a step S1, a feature code $I_{AB}$ first stored in the feature code memory 110 is selected and is set as a remarked feature code originally defined, and the remarked feature code $I_{AB}$ is registered in a central position of the serial codes register 115.

In a step S2, an allowable limit AP in which the remarked feature code $I_{AB}$ is centered is set in, an XY plane.

In a step S3, it is judged whether or not a candidate for a feature code Iab to be connected with the remarked feature code $I_{AB}$ in the right direction to the remarked feature code $I_{AB}$ exists in the allowable limit Ap. In cases where an upper direction code a of a corner code Cf(a,b) in the feature code Iab is the same as a lower direction code B of a corner code Cf(A,B) in the remarked feature code $I_{AB}$, the feature code $I_{AB}$ is selected as a candidate. Also, in cases where a plurality of candidates exist in the allowable limit Ap, a candidate nearest to the remarked feature code $I_{AB}$ is selected. For example, in case of the feature code I21, the feature codes I18 and I12 are selected as candidates. In cases where a candidate exists in the allowable limit Ap, the procedure proceeds to a step S4. In cases where any candidate does not exist in the allowable limit Ap, the procedure proceeds to a step S5.

In the step S4, the candidate is registered in a position of the serial codes register 115 adjacent to the right side of the remarked feature code $I_{AB}$. Thereafter, the candidate is treated as a remarked feature code $I_{AB}$ newly defined, and the steps S2, S3 and S4 are repeated until the procedure proceeds to the step S5.

In the step S5, positional coordinates of the remarked feature code $I_{AB}$ are treated as an ending point Pe, and the ending point Pe is registered in the serial codes register 115.

In a step S6, the feature code $I_{AB}$ originally defined is again selected as a remarked feature code.

In a step S7, an allowable limit Ap in which the remarked feature code $I_{AB}$ is centered is set in the XY plane.

In a step S8, it is judged whether or not a candidate for a feature code Iab to be connected with the remarked feature code $I_{AB}$ in the left direction to the remarked feature code $I_{AB}$ exists in the allowable limit Ap. In cases where a lower direction code b of a corner code Cf(a,b) in the feature code Iab is the same as an upper direction code A of a corner code Cf(A,B) in the remarked feature code $I_{AB}$, the feature code is selected as a candidate. Also, in cases where a plurality of candidates exist in the allowable limit Ap, a candidate nearest to the remarked feature code $I_{AB}$ is selected. In cases where a candidate exists in the allowable limit Ap, the procedure proceeds to a step S9. In cases where any candidate does not exist in the allowable limit Ap, the procedure proceeds to a step S10.

In the step S9, the candidate is registered in a position of the serial codes register 115 adjacent to the left side of the remarked feature code $I_{AB}$. Thereafter, the candidate is treated as the remarked feature code $I_{AB}$, and the steps S7, S8 and S9 are repeated until the procedure proceeds to the step S10.

In the step S10, positional coordinates of the remarked feature code $I_{AB}$ are treated as a starting point Ps, and the starting point Ps is registered in the serial codes register 115. Thereafter, average coordinates of the positional coordinates of the feature codes connected in series in the serial codes register 115 are calculated and registered in the serial codes register 115.

In a step S11, it is judged whether or not one or more feature codes not registered in the serial codes register 115 are stored in the feature code memory 110. In cases where all of the feature codes stored in the feature code memory 110 are not registered in the serial codes register 115, the procedure returns to the step S1. In contrast, in cases where all of the feature codes stored in the feature code memory 110 are registered in the serial codes register 115, the procedure is ended.

Next, a procedure for comparing a series of feature codes Ic3 with a series of referential feature codes Ir2 in the serial codes comparing block 112 is described in detail with reference to FIG. 17.

FIG. 17 is a flow chart showing a procedure of the comparison of a series of feature codes Ic3 and a series of referential feature codes Ir2 performed in the serial codes comparing block 112.

As shown in FIG. 17, in a step S21, a series of referential feature codes is read from a referential serial feature codes file of the referential serial codes register 114. In the referential serial feature codes file, many series of referential feature codes are registered in advance.

In a step S22, average coordinates of positional coordinates of referential feature codes Ir2 existing in the series of referential feature codes read from the file are calculated in the average coordinates calculating unit 116. Thereafter, a referential allowable limit Apr in which the average coordinates are centered is set.

In a step S23, in the inspected serial feature codes file searching unit 117, an inspected serial feature codes file of the inspected serial codes register 111 is searched for a series of feature codes of which average coordinates are placed inside the referential allowable limit Apr. In other words, the inspected serial feature codes file is searched for a series of feature codes corresponding to the series of referential feature codes. In cases where any series of feature codes is not found out, an inspection code "0" indicating the existence of a defect in the referential allowable limit Apr is registered in the referential serial feature codes file. Thereafter, the procedure returns to the step S21 to read another series of referential feature codes. Also, in cases where a series of feature codes is found out inside the referential allowable limit Apr, an inspection code "1" indicating the existence of the series of feature codes is registered in the referential serial feature codes file and the inspected serial feature codes file, and the procedure proceeds to a step S24.

In the step S24, the series of referential feature codes is compared with the series of feature codes, and whether or not a series of corner codes of the series of referential feature codes agrees with a series of corner codes of the series of feature codes is examined in the inspected serial feature codes file examining unit 118. In cases where a series of corner codes of the series of referential feature codes agrees with a series of corner codes of the series of feature codes, a verification code "1" indicating no existence of a defect in the referential allowable limit Apr is registered in the referential serial feature codes file and the inspected serial feature codes file, and the procedure proceeds to a step S25. In other cases, a verification code "0" is registered in the referential serial feature codes file and the inspected serial feature codes file, and the procedure returns to the step S21 to read another series of referential feature codes.

In the step S25, it is judged whether or not a series of referential feature codes not read from the referential serial feature codes file exists. In cases where a series of referential feature codes not read from the referential serial feature codes file exists, the procedure returns to the step S21, and the series of referential feature codes not read is processed in the steps S21 to S24. In other cases, the procedure proceeds to a step S26.

In the step S26, the inspected serial feature codes file is searched for one or more series of feature codes not compared with any series of referential feature codes. In cases where one or more series of feature codes not compared are found out, the feature codes are stored in the defect information storing section 84 as pieces of defect information, and the defect information are reported to the operator.

An example of several series of referential feature codes registered in the referential serial feature codes file is shown in FIG. 18, and an example of several series of feature codes registered in the inspected serial feature codes file is shown in FIG. 19.

In FIGS. 18, 19, the series of referential feature codes are registered in scanning order of a non-defect printed wiring board, and the series of feature codes are registered in scanning order of the printed wiring board 13. Also, average addresses in FIG. 18 respectively denote the average coordinates (X,Y) of the series of referential feature codes, and average addresses in FIG. 19 respectively denote the average coordinates (X,Y) of the series of feature codes. For example, a series of feature codes (No.6) corresponds to a series of referential feature codes (No.4). However the feature codes of the series (No.6) does not agree with the referential feature codes of the series (No.4). Also, any series of feature codes corresponding to a series of referential feature codes (No.6) is not found out. Also, the feature codes of a series of feature codes (No.4) are stored in the defect information storing section 84 as pieces of defect information in the step S26.

Accordingly, because it is judged whether or not each of the feature codes of a series of feature codes corresponds to one of the referential feature codes of a series of referential feature codes, even though a minute shape change actually exists in a non-defect printed wiring board, it is judged at a high reliability whether or not the minute shape change exists in the wiring pattern Pw of the printed wiring board 13.

In the third embodiment, the size of the referential allowable limit Apr is fixed. However, it is applicable that the procedure performed in the serial codes comparing block 112 be repeated after the enlargement of the referential allowable limit Apr to process one or more series of feature codes not compared with any series of referential feature codes.

Next, a fourth embodiment of a wiring pattern detecting apparatus according to the present invention is described with reference to FIGS. 20 to 28.

In the fourth embodiment, comparing and judging operations performed in the second comparing and judging section 26 are described. In this case, a plurality of feature codes Ic3 which each are composed of the corner code Cf(j,DCj) of a feature point and positional coordinates of the feature point are produced in the specific shape detecting section 22 according to the second embodiment and are transferred to the second comparing and judging section 26. The configuration of the second comparing and judging section 26 according to the fourth embodiment is the same as that shown in FIG. 9A. Therefore, comparing and judging operations differing from those in the first embodiment are described in the fourth embodiment. Also, a feature code Ic3 having a corner code "X,Y" is called a feature code $I_{XY}$, and a referential feature code Ir2 having a corner code "X,Y" is called a feature code $Ir_{XY}$ in the fourth embodiment.

Figure 20:
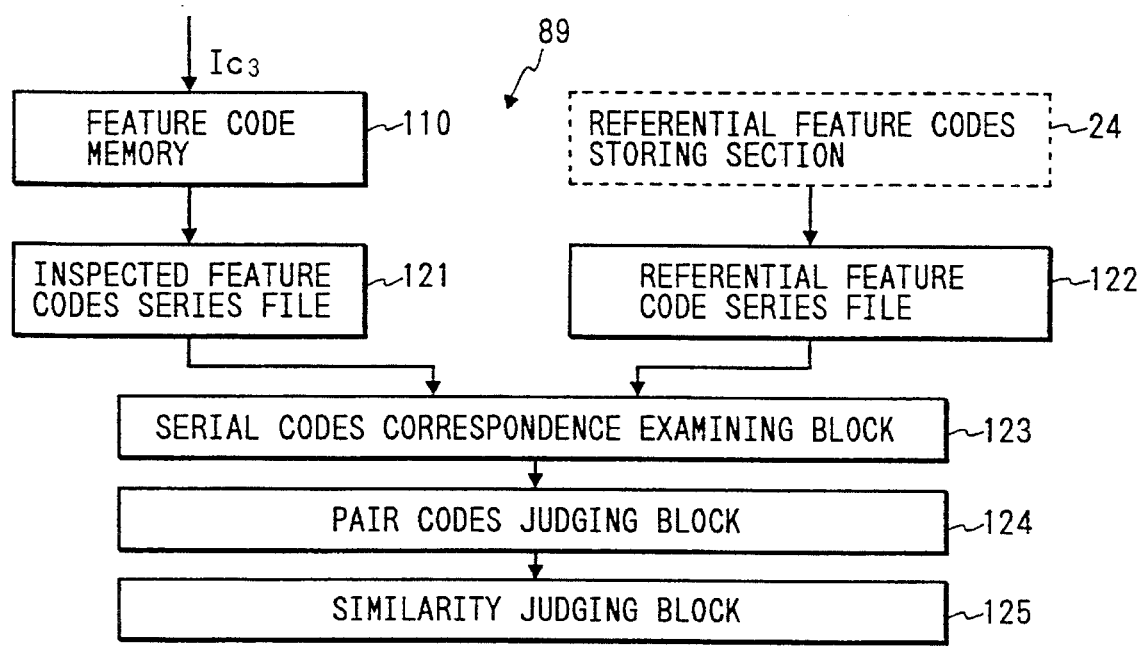
FIG. 20 is a constitutional block diagram of the CPU according to a fourth embodiment of the present invention.

FIG. 20 is a constitutional block diagram of the CPU 89 according to the fourth embodiment.

As shown in FIG. 20, the CPU 89 comprises the feature code memory 110, an inspected feature codes series file 121 for registering an inspected feature codes series produced by serially connecting a plurality of feature codes Ic3 in which each of pairs of feature codes Ic3 adjacent to each other is placed within a prescribed allowable distance in an XY plane, a referenctial feature codes series file 122 for registering a referential feature codes series produced by serially connecting a plurality of referential feature code Ir2 of the non-defective printed wiring board stored in the feature code storing section 24, a serial codes correspondence examining block 123 for examining the correspondence of the feature codes Ic3 in the inspected feature codes series registered in the file 121 to the referential feature codes Ir2 in the referential feature codes series registered in the file 122 to find out paired feature codes Ic3s not corresponding to any referential feature codes Ir2 from the inspected feature codes series or to find out paired referential feature codes Ir2s not corresponding to any feature codes Ic3 from the referential feature codes series, a specific pair codes judging block 124 for judging whether or not the paired feature codes Ic3s or the paired referential feature codes Ir2s found out in the examining block 123 are equivalent to specific pair codes, and a similarity judging block 125 for judging that the inspected feature codes series registered in the file 121 is similar to the referential feature codes series registered in the file 122 to regard the wiring pattern Pw indicated by the inspected feature codes series non-defective in cases where it is judged in the specific pair codes judging block 124 that the paired feature codes Ic3s or the paired referential feature codes Ir2s are equivalent to specific pair codes.

In the above configuration, the inspected feature codes series and the referential feature codes series are registered in the files 121, 122 in the same manner as in the third embodiment. Therefore, the correspondence of the feature codes Ic3 in the inspected feature codes series to the referential feature codes Ir2 in the referential feature codes series is initially described with reference to FIG. 21.

Figure 21:
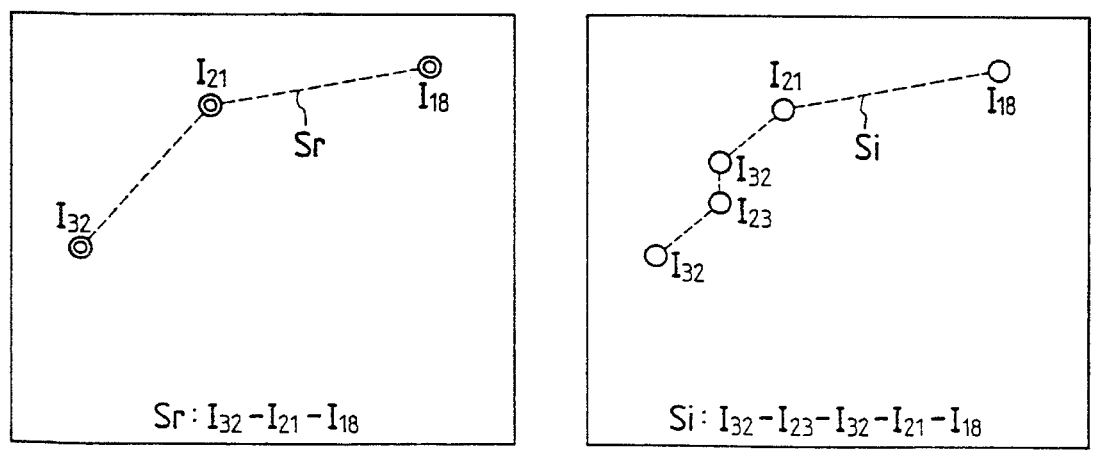
FIG. 21 shows a referential feature codes series Sr and an inspected feature codes series Si having a surplus codes series Ssc.

As shown in FIG. 21, a referential feature codes series Sr is formed by connecting referential feature codes Ir32, Ir21 and Ir18 in serial order, and an inspected feature codes series Si is formed by connecting feature codes I32, I23, I32, I21 and I18 in serial order. In the serial codes correspondence examining block 123, the inspected feature codes series Si is searched for a feature code corresponding to each of the referential feature codes Ir32, Ir21 and Ir18 of the series Sr on condition that a corresponding feature code has the same corner code as that of a referential feature code and is placed nearest to the referential feature code. For example, the feature code I32 of the series Si corresponds to the referential feature code Ir32 of the series Sr because the feature code I32 of the series Si is nearest to the referential feature code Ir32 in the XY plane. Also, the feature code I21 of the series Si corresponds to the referential feature code Ir21 of the series Sr, and the feature code I18 of the series Si corresponds to the referential feature code Ir18 of the Series Sr. However, the feature codes I23, I32 of the series Si do not correspond to any referential feature code of the series Sr, so that the feature codes I23, I32 are called paired feature codes of a surplus code series Ssc. The surplus code series Ssc indicates the difference between the inspected feature codes series Si and the referential feature codes series Sr. Assuming that an inspected feature codes series is searched for a feature code corresponding to each of referential feature codes in an actual operation, it takes a lot of time. Therefore, the correspondence of the feature codes Ic3 in the series Si to the referential feature codes Ir2 in the series Sr is examined at a high speed by applying a dynamic programming matching (DP matching) method in the fourth embodiment. The DP matching method is well-known in a speech recognition and a pattern matching and is proposed in a literature (Y. Kousaka, K. Ozeki; "An Algorism of Pattern Recognition and Learning", published by Bunichisougo-syuppan, pp.91–108 (1990)).

A corresponding processing performed in the serial codes correspondence examining block 123 according to the DP matching method is described.

A first feature codes series A=a1a2- - - aI and a second feature codes series B=b1b2 - - - bJ are prepared. A symbol I denotes a length of the series A, and a symbol J denotes a length of the series B. Each of the feature codes ak (k=1,2, -,i,- - , I) and bk (k=1,2,-,j,- - ,J) is composed of a corner code Ca or Cb, a coordinate Xa or Xb of the X-axis and a coordinate Ya and Yb of the Y-axis and is expressed by ak={Ca,Xa,Ya} or bk={Cb,Xb,Yb}. Thereafter, a similarity S(ak,bk) between feature codes ak and bk is calculated according to an estimating equation (15).

$$S(ak,bk) = \begin{cases} (Xa-Xb)^2 + (Ya-Yb)^2: & \text{when } Ca = Cb \text{ is satisfied.} \\ 400: & Ca \neq Cb, \text{ a feature code } bj \\ & \text{corresponding to} \\ & \text{the feature code } ak \text{ exists,} \\ & \text{and a feature code } ai \\ & \text{corresponding to the feature} \\ & \text{code } bk \text{ exits.} \\ 100: & Ca \neq Cb, \text{ and any feature code } bj \\ & \text{corresponding to the feature code } ak \text{ does} \\ & \text{not exist or any feature code } ai \\ & \text{corresponding to the feature code } bk \text{ does} \\ & \text{not exist.} \end{cases}$$

In the DP matching method, the higher a priority order of the combination between the feature codes ak and bk is, the lower a value of the similarity S(ak,bk) is. Therefore, because the priority order of the combination between the feature codes ak and bk is higher in cases where a distance between the feature codes ak and bk be becomes smaller on condition that the corner codes Ca, Cb are the same, the value of the similarity S(ak,bk) is equal to the distance between the feature codes ak and bk in case of Ca=Cb, the value of the similarity S(ak,bk) is set to 400 in case of Ca≠Cb, and the value of the similarity S(ak,bk) is set to 100 in cases where the corner code Ca or Cb is unknown.

Therefore, in cases where feature codes of the series Si corresponding to the referential feature codes Ir32, Ir21 and Ir18 of the series Sr are examined on condition that the sum of values of the similarities S(Ic3, Ir32), S(Ic3,Ir21) and S(Ic3,Ir18) is minimized, paired feature codes I23 and I32 not corresponding to any referential feature code Ir2 of the series Sr can be found out.

Also, the feature codes of the series Si corresponding to the referential feature codes of the series Sr can be efficiently examined by utilizing equations (16), (17).

$$G(0,0)=0 \quad (16a)$$

$$G(i,0)=S(a1,*)+S(a2,*)+ - - +S(ai,*) \quad (1 \leq i \leq I) \quad (16b)$$

$$G(0,j)=S(*,b1)+S(*,b2)+ - - +S(*,bj) \quad (1 \leq j \leq J) \quad (16c)$$

$$G(i,j)=\min\{G(i-1,j)+S(ai,*), G(i-1,j-1)+S(ai,bj), G(i,j-1)+S(*,bj)\} \quad (17)$$

Here a symbol * denotes that a feature code is unknown, and a symbol min{ } denotes an operator for obtaining a minimum value.

The value G(i,j) indicates the sum of values of the similarities S which is obtained when feature codes of a series Ai=a1a2 - - - ai correspond to feature codes of a series Bj=b1b2 - - - bj on condition that a corresponding feature code of the series Ai has the same corner code as that of a feature code of the series Bj and is placed nearest to the feature code of the series Bj. Therefore, the value G(I,J) indicates the sum of values of the similarities S which is obtained when feature codes of the series A correspond to feature codes of the series on condition that a corresponding feature code of the series A has the same corner code as that of a feature code of the series B and is placed nearest to the feature code of the series B.

The equation (17) is a recurrence formula, and the equations (16a) to (16c) denote initial formulas of the recurrence formula. Therefore, a combination of a feature code of the series Bj and a feature code of the series Ai is selected to minimize the value G(i,j) by utilizing the values G(i−1,j), G(i−1,j−1) and G(i,j−1) previously calculated. Therefore, because a current value G(i,j) is obtained by utilizing the values previously calculated, a calculation volume for obtaining the value G(I,J) can be minimized. Also, in cases where one or more feature codes Ic3 not corresponding to any referential feature code Ir2 are stored each time the value G(i,j) is calculated paired feature codes Ic3s of a surplus code series Ssc can be easily found out.

FIG. 22 shows an example of an inspected code series A and a referential code series B. FIG. 23 shows an example of the correspondence of feature codes in the inspected codes series A to the referential feature codes in the referential codes series B, the correspondence being determined according to the DP matching method in the serial codes correspondence examining block 123.

As shown in FIG. 22, the inspected code series A is composed of feature codes I18, I81, I18 and I87 arranged in serial order, and the referential codes series B is composed of referential feature codes Ir18 and Ir87 arranged in serial order. As shown in FIG. 23, values of G(1,1), G(1,2), G(2,1), G(2,2), G(3,1), G(3,2), G(4,1) and G(4,2) are calculated according to the equation (17) in that order, and the correspondence of feature codes to referential feature codes is examined each time G(i,j) is calculated. Also, one or more paired codes found out are listed each time G(i,j) is calculated.

Accordingly, because paired codes I81 and I18 of a surplus codes series are found out when the value G(4,2) is finally calculated, a surplus codes series Ssc=I81-I18 is determined in the serial codes correspondence examining block 123.

Next, a concept of the judgement whether or not the surplus codes series is equivalent to a pair codes series is described with reference to FIGS. 24, 25.

FIG. 24A shows a referential feature codes series Sr and an inspected feature codes series Si having a surplus codes series Ssc. FIG. 24B shows a referential feature codes series Sr having a surplus codes series Ssc and an inspected feature codes series Si.

When one or more quantization errors occur in the bi-level image Ib, an inspected feature codes series Si determined in the inspected featurecodes series file 121 according to a plurality of feature codes Ic3 produced by detecting specific shapes of the printed wiring board 13 having no defect in the detecting section 22 does not necessarily agree with a referential feature codes series Sr determined in the referential feature codes series file 122 according to a plurality of referential feature codes produced from specific shapes of a non-defective printed wiring board, even though the printed wiring board 13 has no defect. Therefore, as shown in FIG. 24A, false corners resulting from a quantization error are undesirably formed in an area of the wiring pattern Pw, and a surplus codes series Ssc is excessively formed in the inspected feature codes series Si. In this case, because the quantization error occurs in a narrow area, the surplus codes series SSc pertaining to the quantization error is also formed in the same narrow area. Therefore, in cases where the surplus codes series Ssc is placed within a narrow allowable limit Aq, it is judged that the surplus codes series Ssc is equivalent to a pair codes series, and it is judged that the inspected feature codes series Si agree with the referential feature codes series Sr regardless of the existence of the surplus codes series Ssc.

Also as shown in FIG. 24B, in cases where a small edge is actually formed in an area of a non-defective printed wiring board a surplus codes series Ssc is formed in the referential feature codes series Sr. However, there is a case that the small edge is erroneously overlooked in the bi-level image Ib because of a quantization error. Therefore, in cases where the surplus codes series Ssc placed within a narrow allowable limit Aq is found out in the referential feature codes series Sr, it is judged that the surplus codes series Ssc is equivalent to a pair codes series, and it is judged that the inspected feature codes series Si agree with the referential feature codes series Sr.

A definition of a pair code series is described with reference to FIGS. 25A, 25B.

Figures 25A, 25B:
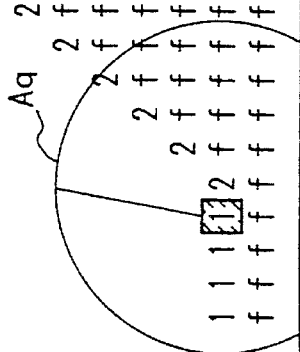
FIG. 25A shows the arrangement of direction codes DCi in which paired codes I12 and I21 of a surplus codes series resulting from a quantization error are produced in an LUT shown in FIG. 13.
FIG. 25B shows the arrangement of direction codes DCi in which paired codes I12 and I21 of a surplus codes series are produced in the LUT because two corners actually exist.

FIG. 25A shows the arrangement of direction codes DCi in which paired codes I12 and I21 of a surplus codes series resulting from a quantization error are produced in the LUT 108. FIG. 25B shows the arrangement of direction codes DCi in which paired codes I12 and I21 of a surplus codes series are produced in the LUT 108 because two corners actually exist.

In cases where a quantization error occurs in a narrow area of the bi-level image, paired codes Iab and Iba of a surplus codes series Ssc are placed within a narrow allowable limit Aq. In this case, an upper direction code "a" of a corner code Cf(a,b) in the paired code Iab agrees with a lower direction code "a" of a corner code Cf(b,a) in the paired code Iba, and a lower direction code "b" of the corner code Cf(a,b) in the paired code Iab agrees with an upper direction code "b" of the corner code Cf(b,a) in the paired code Iba. Therefore, a surplus codes series Ssc having the paired codes Iab, Iba within a narrow allowable limit Aq is defined as a pair codes series. For example, as shown in FIG. 25A, a surplus codes series Ssc having the paired codes I12, I21 within a narrow allowable limit Aq is equivalent to a pair codes series.

In contrast, even though a surplus codes series Ssc is composed of paired codes Iab and Iba, in cases where the paired codes Iab and Iba are not placed in the same narrow allowable limit Aq, two corners of the wiring pattern Pw indicated by the paired codes Iab and Iba actually exist. Therefore, in this case, a surplus codes series Ssc having the paired codes Iab, Iba is not equivalent to a pair codes series. For example, as shown in FIG. 25B, a surplus codes series Ssc having the paired codes I12, I21 is not equivalent to a pair codes series because the paired codes I12, I21 are not placed in the same narrow allowable limit Aq.

Accordingly, in cases where it is judged whether or not a surplus codes series Ssc is placed inca narrow allowable limit Aq, a pair codes series resulting from a quantization error can be distinguished from a surplus codes series Ssc which indicates two corners actually existing in the wiring pattern Pw. Therefore, in cases where it is judged whether or not an inspected codes series Si agrees with a referential codes series Sr on condition that the pair codes series is deleted or disregarded, unstableness of the wiring pattern Pw resulting from quantization errors can be allowed, and the printed wiring board 13 can be inspected with a high accuracy.

Next, operations performed in the serial codes correspondence examining block 123, the specific pair codes judging block 124 and the similarity judging block 125 are described with reference to FIG. 26.

Figure 26:
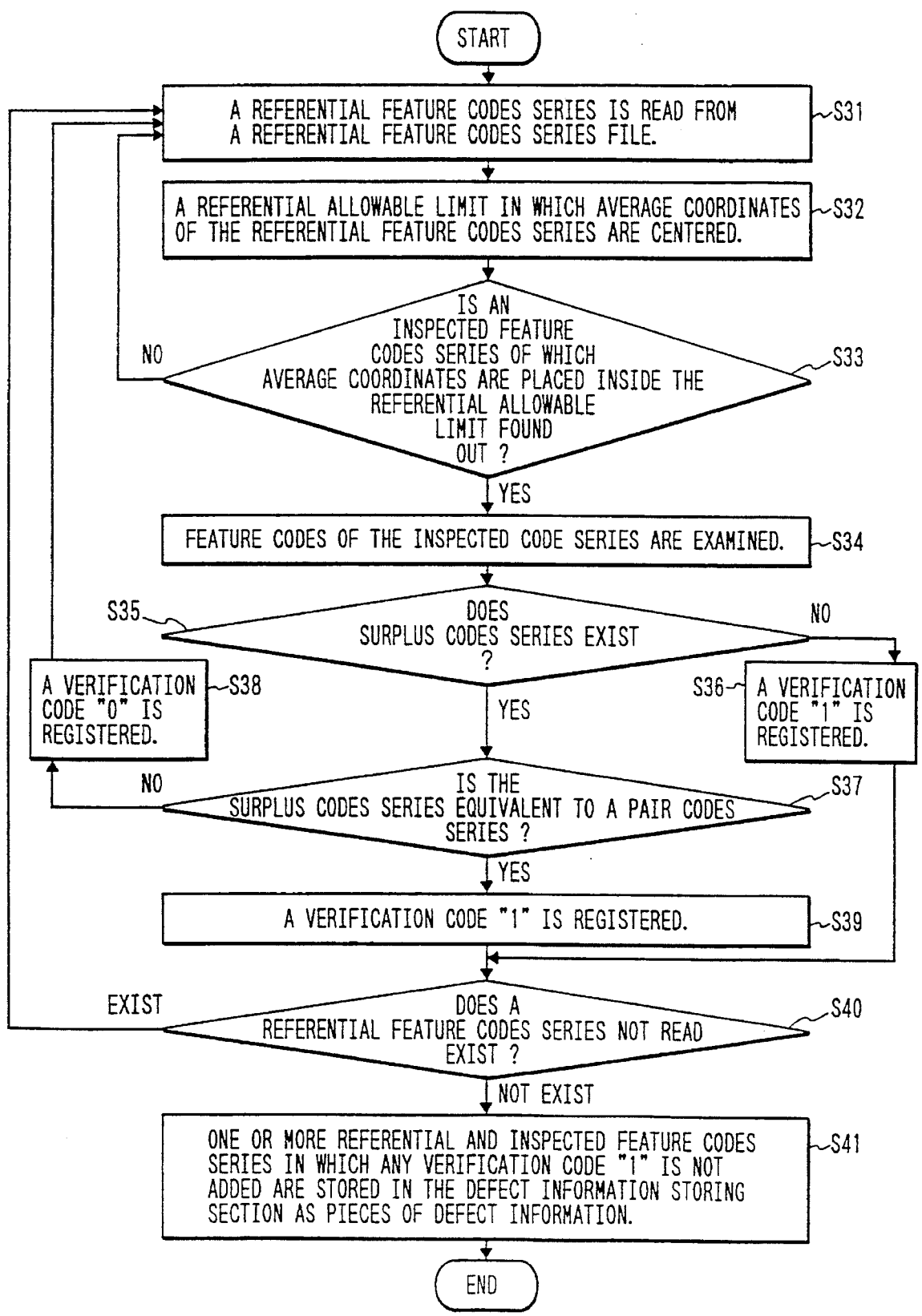
FIG. 26 is a flow chart showing a procedure of the collation of an inspected codes series with a referential codes series according to the fourth embodiment.

FIG. 26 is a flow chart showing a procedure of the collation of an inspected codes series with a referential codes series according to the fourth embodiment.

As shown in FIG. 26, in a step S31, a referential feature codes series is read out from the referential feature codes series file 122 to the serial codes correspondence examining block 123. In the file 122, many referential feature codes series are registered in advance.

In a step S32, average coordinates of referential feature codes Ir2 composing the referential feature codes series read out from the file 122 are calculated in the block 123. Thereafter, a referential allowable limit Apr in which the average coordinates are centered is set.

In a step S33, the inspected feature codes series file 121 is searched for an inspected feature codes series of which average coordinates are placed inside the referential allowable limit Apr. In other words, the inspected feature codes series file 121 is searched for an inspected feature codes series corresponding to the referential feature codes series. In cases where any feature codes series is not found out, an inspection code "0" indicating the existence of a defect in the referential allowable limit Apr is registered in the referential feature codes series file 122. Thereafter, the procedure returns to the step S31 to read another referential feature codes series. Also, in cases where a feature codes series is found out inside the referential allowable limit Apr, an inspection code "1" indicating the existence of the series of feature codes is registered in the referential feature codes series file 122 and the inspected feature codes series file 121, and the procedure proceeds to a step S34.

In the step S34, feature codes Ic3 of the inspected feature codes series corresponding to referential feature codes of the referential feature codes series are examined in the examining block 123.

In a step S35, it is judged whether or not paired codes of a surplus codes series Ssc which do not correspond to any referential feature codes exist in the inspected feature codes series. Also, it is judged whether or not paired codes of a surplus codes series Ssc which do not correspond to any feature codes Ic3 exist in the referential feature codes series. In cases where any paired codes are not found out, the procedure proceeds to a step S36. In cases where paired codes are found out in the surplus codes series Ssc, the procedure proceeds to a step S37.

In the step S36, a verification code "1" indicating that no defect exists in the referential allowable limit Apr of the wiring pattern Pw is registered in the referential feature codes series file 122 and the inspected feature codes series file 121, and the procedure proceeds to a step S40. That is, the verification code "1" is added to the referential feature codes series and the inspected feature codes series.

In the step S37, it is judged in the specific pair codes judging block 124 whether or not the surplus codes series Ssc is equivalent to a pair codes series. In cases where the surplus codes series Ssc is not equivalent to a pair codes series, the procedure proceeds to a step S38. In cases where the surplus codes series Ssc is equivalent to a pair codes series, it is judged in the similarity judging block 125 that the inspected feature codes series is similar to the referential feature codes series, and the wiring pattern Pw indicated by the inspected feature codes series is regarded as non-defective. Therefore, the procedure proceeds to a step S39.

In the step S38, a verification code "0" indicating that a defect exists in the referential allowable limit Apr of the wiring pattern Pw is registered in the referential feature codes series file 122 and the inspected feature codes series file 121. Thereafter, the procedure returns to the step S31 to read another referential feature codes series.

In the step S39, the verification code "1" is registered in the referential feature codes series file 122 and the inspected feature codes series file 121, and the procedure proceeds to the step S40. That is, the verification code "1" is added to the referential feature codes series and the inspected feature codes series.

In the step S40, it is judged whether or not a referential feature codes series not read out from the referential feature codes series file 22 exists. In cases where a referential feature codes series not read from the file 122 exists, the procedure returns to the step S31, and the referential feature codes series is processed in the steps S31 to S39. In other cases, the procedure proceeds to a step S41.

In the step S41, the inspected feature codes series file is searched for one or more inspected feature codes series in which the verification code "0" is added or any verification code "1" is not added. In cases where one or more inspected feature codes series not having any verification code "1" are found out, the inspected feature codes series are stored in the defect information storing section 84 as pieces of defect information. Also, the referential feature codes series file is searched for one or more referential feature codes series in which the verification code "0" is added or any verification code "1" is not added. In cases where one or more referential feature codes series not having any verification code "1" are found out, the referential feature codes series are stored in the defect information storing section 84 as pieces of defect information. Thereafter, the defect information are reported to the operator.

An example of several referential feature codes series registered in the referential feature codes series file is shown in FIG. 27, and an example of several feature codes series registered in the inspected feature codes series file is shown in FIG. 28.

In FIGS. 27, 28, the referential feature codes series are registered in scanning order of a non-defect printed wiring board, and the feature codes series are registered in scanning order of the printed wiring board 13. Also, average addresses in FIG. 27 respectively denote the average coordinates (X,Y) of the referential feature codes series, and average addresses in FIG. 28 respectively denote the average coordinates (X,Y) of the inspected feature codes series. For example, an inspected feature codes series (No.6) corresponds to a referential feature codes series (No.4). However, a surplus codes series is found out in the referential feature codes series (No.4). Because the surplus codes series is not equivalent to a pair codes series, the verification code "0" is added to the referential feature codes series (No.4) and the inspected feature codes series (No.6). Also, because feature codes I78 and I81 of an inspected feature codes series (No.4) do not agree with referential feature codes I78, I81, I12 and I21 of a referential feature codes series (No.6). Therefore, the inspected feature codes series (No.4) does not correspond to the referential feature codes series (No.6). However, because a surplus codes series composed of feature codes I12, I21 is found out in the inspected feature codes series (No.4) and is equivalent to a pair codes series, the verification code "1" is added to the referential feature codes series (No.6) and the inspected feature codes series (No.4).

Accordingly, even though a pair codes series is formed in an inspected feature codes series because of a quantization error, the judgement that no defect exist in the wiring pattern Pw can be correctly performed. In detail, a false inspection resulting from the quantization error can be prevented at a high reliability, and the printed wiring board 13 can be stably inspected. Also, even though a pair codes series is formed in a referential feature codes series because a meaningless concavo-convex portion actually exists in a non-defective wiring pattern, the inspection of the wiring pattern Pw can be correctly performed by disregarding the meaningless concavo-convex portion.

Next, a fifth embodiment of a wiring pattern detecting apparatus according to the present invention is described with reference to FIGS. 29 to 33.

In the fifth embodiment, comparing and judging operations performed in the second comparing and judging section 26 are described. In this case, a plurality of feature codes Ic3 which each are composed of the corner code Cf(j,DCj) of a feature point and positional coordinates of the feature point are produced in the specific shape detecting section 22 according to the second embodiment and are transferred to the second comparing and judging section 26. The configuration of the second comparing and judging section 26 according to the fifth embodiment is the same as that shown in FIG. 9A. Therefore, comparing and judging operations differing from those in the first embodiment are described in the fifth embodiment. Also, a feature code Ic3 having a corner code "X,Y" is called a feature code $I_{xy}$, and a referential feature code Ir2 having a corner code "X,Y" is called a feature code $Ir_{xy}$ in the fifth embodiment.

Figure 29:
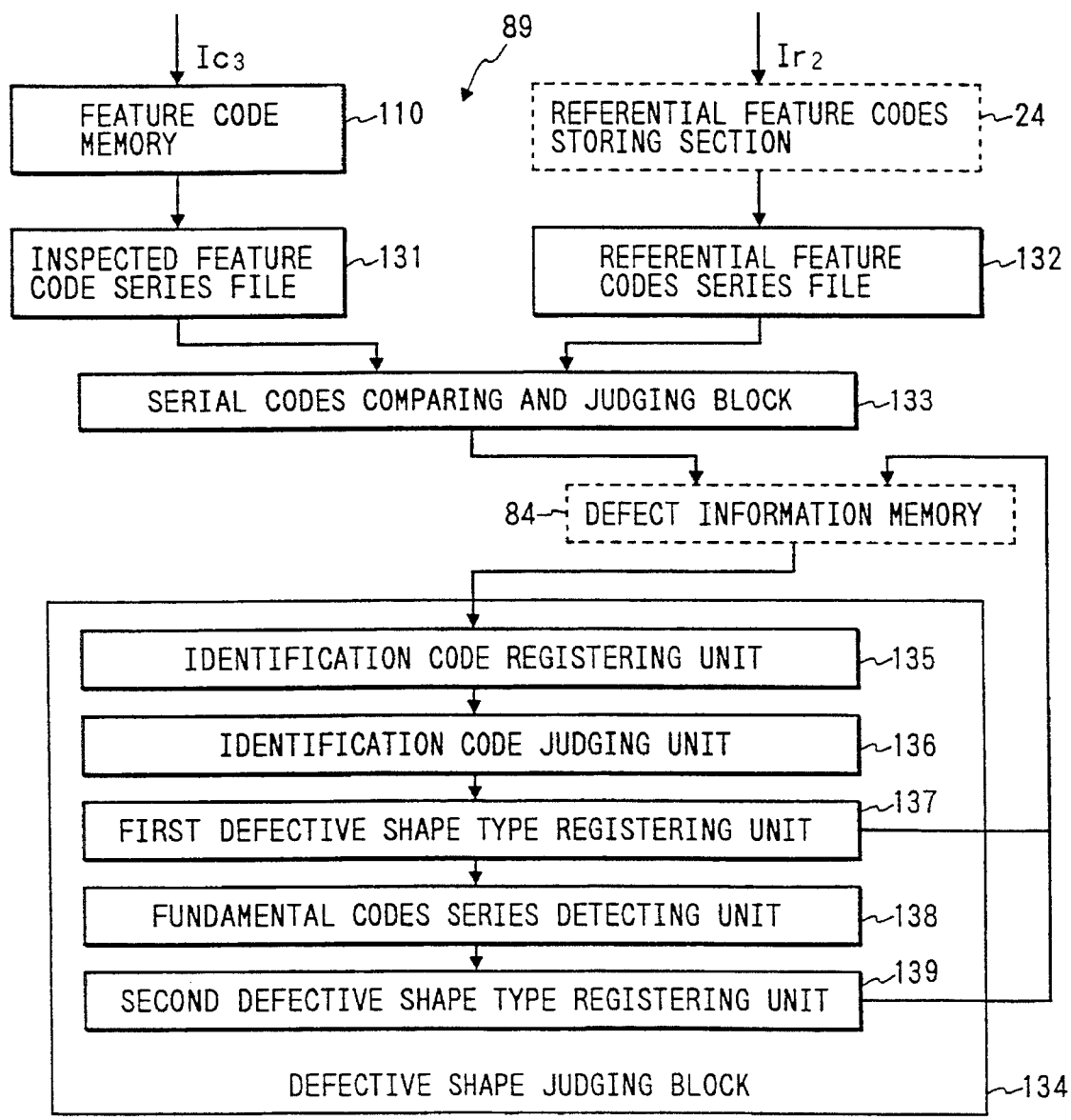
FIG. 29 is a constitutional block diagram of the CPU shown in FIG. 9 according to a fifth embodiment of the present invention.

FIG. 29 is a constitutional block diagram of the CPU 89 according to the fifth embodiment.

As shown in FIG. 29, the CPU 89 comprises the feature code memory 110, an inspected feature codes series file 131 for registering an inspected feature codes series produced by serially connecting a plurality of feature codes Ic3 in which each of pairs of feature codes Ic3 adjacent to each other is placed within a prescribed allowable limit Ap in an XY plane, a referential feature codes series file 132 for registering a referential feature codes series produced by serially connecting a plurality of referential feature code Ir2 of the non-defective printed wiring board stored in the feature code storing section 24, a serial codes comparing and judging block 133 for comparing the inspected feature codes series registered in the file 131 with the referential feature codes series registered in the file 132, judging whether or not the inspected feature codes series agrees with the referential feature codes series, and storing the inspected feature codes series which does not agree with the referential feature codes series in the defect information memory 84 as a piece of defect information, and a defective shape judging block 134 for inspecting whether or not one of a plurality of fundamental codes series indicating a plurality of defective shape types of the wiring pattern Pw is included in the inspected feature codes series stored in the defect information memory 84 in cases where it is judged in the judging block 133 that the inspected feature codes series does not agree with the referential feature codes series and judging a type of a defective shape existing in the wiring pattern indicated by the inspected feature codes series.

In the above configuration, operations performed in the files 131, 132 and the block 133 are the same as those performed in the blocks 111, 112 and the register 114 according to the third embodiment. Therefore, the operations are omitted, and a defective shape judging operation performed in the defective shape judging block 134 is initially described.

Figure 30B:
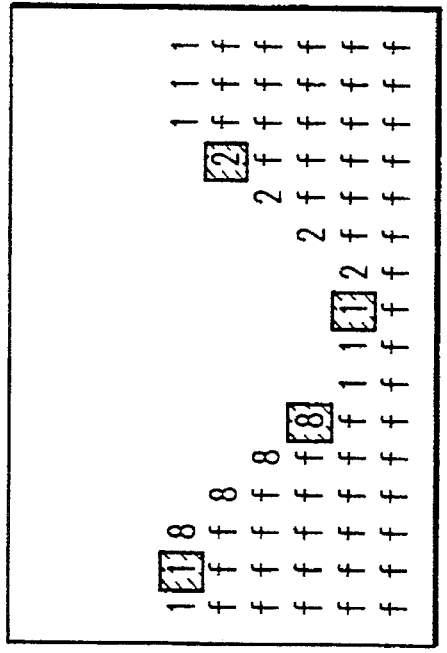
FIG. 30B shows the arrangement of direction codes indicating a disconnection portion of a wiring pattern as a defective shape type.
Figure 30A:
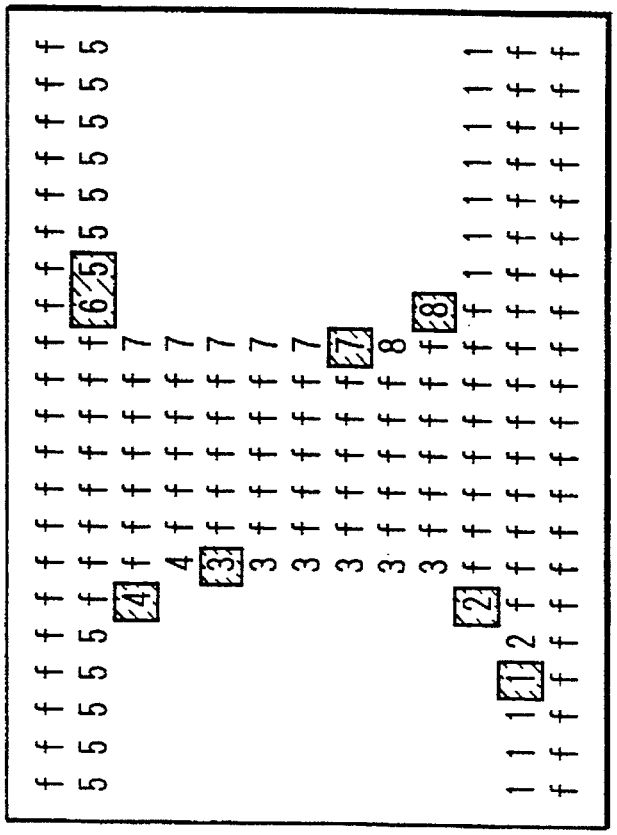
FIG. 30A shows the arrangement of direction codes indicating a short portion of a wiring pattern as a defective shape type.

FIG. 30A shows the arrangement of direction codes indicating a short portion of a wiring pattern as a defective shape type. FIG. 30B shows the arrangement of direction codes indicating a disconnection portion of a wiring pattern as a defective shape type. FIG. 30C shows the arrangement of direction codes indicating a disconnecting portion of a wiring pattern as a defective shape type. FIG. 30D shows the arrangement of direction codes indicating a protrusion portion of a wiring pattern as a defective shape type. FIG. 30E shows the arrangement of direction codes indicating a remaining copper portion of a wiring pattern as a defective shape type. FIG. 30F shows the arrangement of direction codes indicating a pinhole portion of a wiring pattern as a defective shape type.

The defect occurring in the printed wiring board 13 is classified into six defective shape types composed of a short, a disconnection, an open-end, a protrusion, a residue and a pinhole. In this case, as shown in FIG. 30A, a fundamental codes series "I12-I23-I34-I45" and another fundamental codes series "I56-I67-I78-I81" are necessarily included in a feature codes series which indicates a wiring pattern including a short as a defective shape. In addition, in cases where the short in eight wiring patterns rotated every 45 degrees is considered, there are eight types fundamental codes series as shown in FIG. 31A. Also, as shown in FIG. 30B, a fundamental codes series "I18-I81-I12-I21" is necessarily included in a feature codes series which indicates a wiring pattern including a disconnection as a defective shape. In addition, in cases where the disconnection in eight wiring patterns rotated every 45 degrees is considered, there are eight types fundamental codes series as shown in FIG. 31C. Also, as shown in FIG. 30C, a fundamental codes series "I18-I87-I76-I65" and another fundamental codes series "I54-I43-I32-I21" are necessarily included in a feature codes series which indicates a wiring pattern including an open-end as a defective shape. In addition, in cases where the open-end in eight wiring patterns rotated every 45 degrees is considered, there are eight types fundamental codes series as shown in FIG. 31B. Also, as shown in FIG. 30D, a fundamental codes series "I12-I21-I18-I81" is necessarily included in a feature codes series which indicates a wiring pattern including a protrusion as a defective shape. In addition, in cases where the protrusion in eight wiring patterns rotated every 45 degrees is considered, there are eight types fundamental codes series as shown in FIG. 31D. Also, as shown in FIG. 30E, a fundamental codes series "I18-I87-I76-I65-I54-I43-I32-I21" is necessarily included in a feature codes series which indicates a wiring pattern including a residue as a defective shape. Because a shape of the residue is rotation symmetry, as shown in FIG. 31E, the fundamental codes series in the residue is only "I18-I87-I76-I65-I54-I43-I32-I21". Also, as shown in FIG. 30F, a fundamental codes series "I45-I56-I67-I78-I81-I12-I23-I34" is necessarily included in a feature codes series which indicates a wiring pattern including a pinhole as a defective shape. Because a shape of the pinhole is rotation symmetry, as shown in FIG. 31F, the fundamental codes series in the pinhole is only "I45-I56-I67-I78-I81-I12-I23-I34".

In an actual wiring pattern having one or more defects, a feature coded series indicating the actual wiring pattern is more complicated. However, one of the fundamental codes series shown in FIG. 31A to 31F is necessarily included in the feature coded series.

Therefore, to judge a defective shape of the wiring pattern Pw indicated by an inspected feature codes series, it is inspected in the defective shape judging block 134 whether or not one of the fundamental codes series shown in FIGS. 31A to 31F is included in the inspected feature codes series. Also, in cases where the wiring pattern Pw has a short portion or a disconnection portion, as shown in FIG. 30A or FIG. 30B, a pair of fundamental codes series is necessarily included in the inspected feature coded series. Therefore, a defect type such as a short or a disconnection can be easily detected.

In detail, as shown in FIG. 29 the defective shape judging block 134 comprises an identification code registering unit 135 for registering an identification code indicating a type of a defective shape of the wiring pattern Pw to the defect information memory 84 in connection with the inspected feature codes series, an identification code judging unit 136 for judging whether or not the identification code indicating a short or an open-end is registered in the identification code registering unit 135, a first defective shape type registering unit 137 for registering a defective shape type such as a disconnection, a protrusion, a residue or a pinhole to the defect information memory 84 in connection with the inspected feature codes series in cases where it is judged in the indication code judging unit 136 that any identification code indicating a short or an open-end is not registered, a fundamental codes series detecting unit 138 for detecting a second fundamental codes series pairing with the fundamental codes series of the inspected feature codes series in a corresponding inspected feature codes series stored in the defect information memory 84 in cases where it is judged in the identification code judging unit 136 that an identification code indicating a short or an open-end is registered, and a second defective shape type registering unit 139 for registering a defective shape type such as a short or an open-end to the defect information memory 84 in connection with the inspected feature codes series and the corresponding inspected feature codes series.

In the above configuration, a procedure for judging a defective shape type of the inspected feature codes series in the defective shape judging block 134 is described in detail with reference to FIG. 32.

Figure 32:
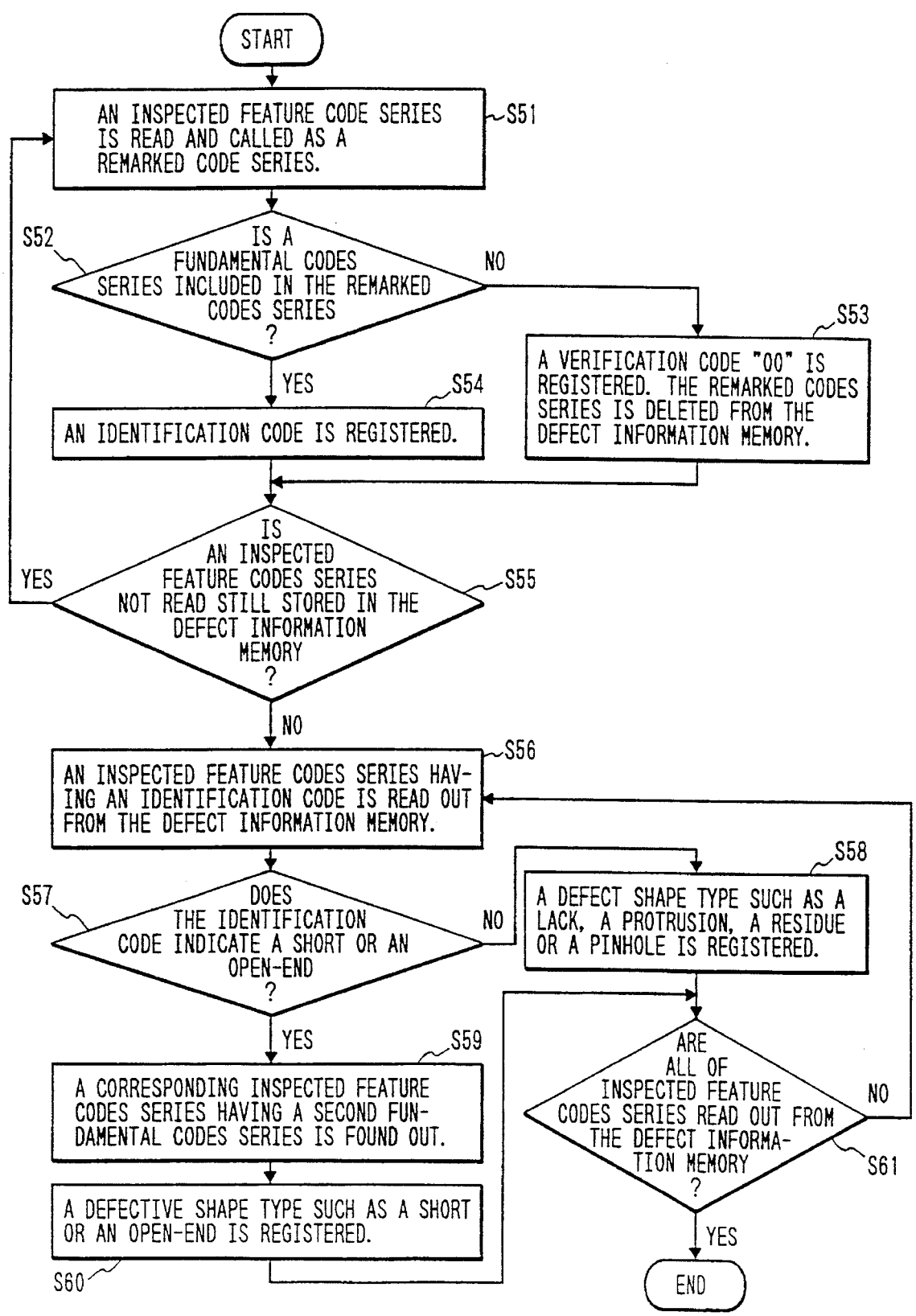
FIG. 32 is a flow chart showing a procedure for judging a defective shape type of an inspected feature codes series according to the fifth embodiment.

FIG. 32 is a flow chart showing a procedure for judging a defective shape type of the inspected feature codes series according to the fifth embodiment.

As shown in FIG. 32, in a step S51, one or more inspected feature codes series are stored in the defect information memory 84 as pieces of defect information in cases where the inspected feature codes series do not respectively agree with any referential feature codes series in the block 133. Thereafter, an inspected feature codes series is read out from the defect information memory 84 to the Judging block 134. The inspected feature codes series is called a remarked codes series.

In a step S52, it is judged whether one or more fundamental codes series are included in the remarked codes series. In cases where it is judged that any fundamental codes series is not included in the remarked codes series, the procedure proceeds to a step S53. Also, in cases where it is judged that one or more fundamental codes series are included in the remarked codes series, the procedure proceeds to a step S54.

In the step S53, a verification code "00" indicating that no defect exists in the wiring pattern Pw indicated by the remarked codes series is registered in the defect information memory 84 in connection with the remarked codes series. Thereafter, the remarked codes series is deleted from the defect information memory 84. That is, it is judged that the remarked codes series is not equivalent to a piece of defect information. Thereafter, the procedure proceeds to a step S55.

In the step S54, in the registering unit 135, an identification code indicating that a defect exists in the wiring pattern Pw indicated by the remarked codes series is registered to the defect information memory 84 in connection with the remarked codes series. For example, in cases where a fundamental codes series corresponding to a short is included, an identification code "Ai" (i=1,2, - -, or 8) shown in FIG. 31A is registered. In cases where a fundamental codes series corresponding to an open-end is included, an identification code "Bi" shown in FIG. 31B is registered. In cases where a fundamental codes series corresponding to a disconnection is included, an identification code "Ci" shown in FIG. 31C is registered. In cases where a fundamental codes series corresponding to a protrusion is included, an identification code "Di" shown in FIG. 31D is registered. In cases where a fundamental codes series corresponding to a residue is included, an identification code "E1" shown in FIG. 31E is registered. In cases where a fundamental codes series corresponding to a pinhole is included, an identification code "F1" shown in FIG. 31F is registered. Thereafter, the procedure proceeds to the step S55.

In the step S55, it is judged whether or not another inspected feature codes series not read out to the judging block 134 is still stored in the defect information memory 84. In cases where another inspected feature codes series not read out to the judging block 134 remains in the defect information memory 84, the procedure returns to the step 51 to repeat the steps 51 to 55 until all of the inspected feature codes series are read out to the judging block 134.

In the step S56, an inspected feature codes series to which an identification code is registered is read out from the defect information memory 84 to the judging block 134. The inspected feature codes series is called a remarked codes series.

In a step S57, it is judged in the judging unit 136 whether or not the identification code registered in connection with the remarked codes series indicates a short or an open-end. In cases where any identification code "Ai" or "Bi" indicating a short or an open-end is not registered in connection with the remarked codes series, the procedure proceeds to a step S58. Also, in cases where the identification code "Ai" or "Bi" indicating a short or an open-end is registered in connection with the remarked codes series, the procedure proceeds to a step S59.

In the step S58, in the registering unit 137, a defect shape type such as a disconnection, a protrusion, a residue or a pinhole is registered to the defect information memory 84 in connection with the remarked code series according to the identification code registered in connection with the remarked codes series. Thereafter, the procedure proceeds to a step S61.

In the step S59, a corresponding inspected feature codes series having a second fundamental codes series which pairs with the fundamental codes series included in the remarked codes series is found out from the defect information memory 84 in the detecting unit 138. The corresponding inspected feature codes series is registered in the defect information memory 84 in connection with the remarked codes series.

In a step S60, a defect shape type such as a short or an open-end is registered to the remarked code series of the defect information memory 84 in the registering unit 139 according to the combination of the fundamental codes series and the second fundamental codes series.

In the step S61, it is judged whether or not all of inspected feature codes series to which the identification codes are registered are read out from the defect information memory 84 to the judging block 134. In cases where one or more inspected feature codes series to which the identification codes are registered are not read out to the judging block 134, the procedure returns to the step S56 to repeat the steps S56 to S61 until all of the inspected feature codes series to which the identification codes are registered are read out to the judging black 134. In contrast, in cases where all of the inspected feature codes series are read out, the procedure is ended.

An example of referential feature codes series registered in the defect information memory 84 is shown in FIG. 33.

In FIG. 33, the referential feature codes series are registered in scanning order of the printed wiring board 13. Also, average addresses respectively denote the average coordinates (X,Y) of the inspected feature codes series. For example, because the identification codes "A1", "A5" are registered for the inspected feature codes series (No. 2419 and No. 2420) which are placed in the neighborhood, the defect shape types of the inspected feature codes series (No. 2419 and No. 2420) are judged as a short. Also, because the identification code "C7" is registered for the inspected feature codes series (No. 2793), the defect shape type of the inspected feature codes series (No. 2793) is judged as a disconnection. Also, because no fundamental code series exists in the inspected feature codes series (No. 4664 and No. 5156), the inspected feature codes series (No. 4664 and No. 5156) are deleted from the defect information memory 84.

Accordingly, a schedule control for the inspection of the printed wiring board 13 can be easily performed because the defective shape types of the inspected feature codes series are visually registered in the defect information memory 84. Also, an operator can be easily performed the inspection of the printed wiring board 13.

Figure 34:
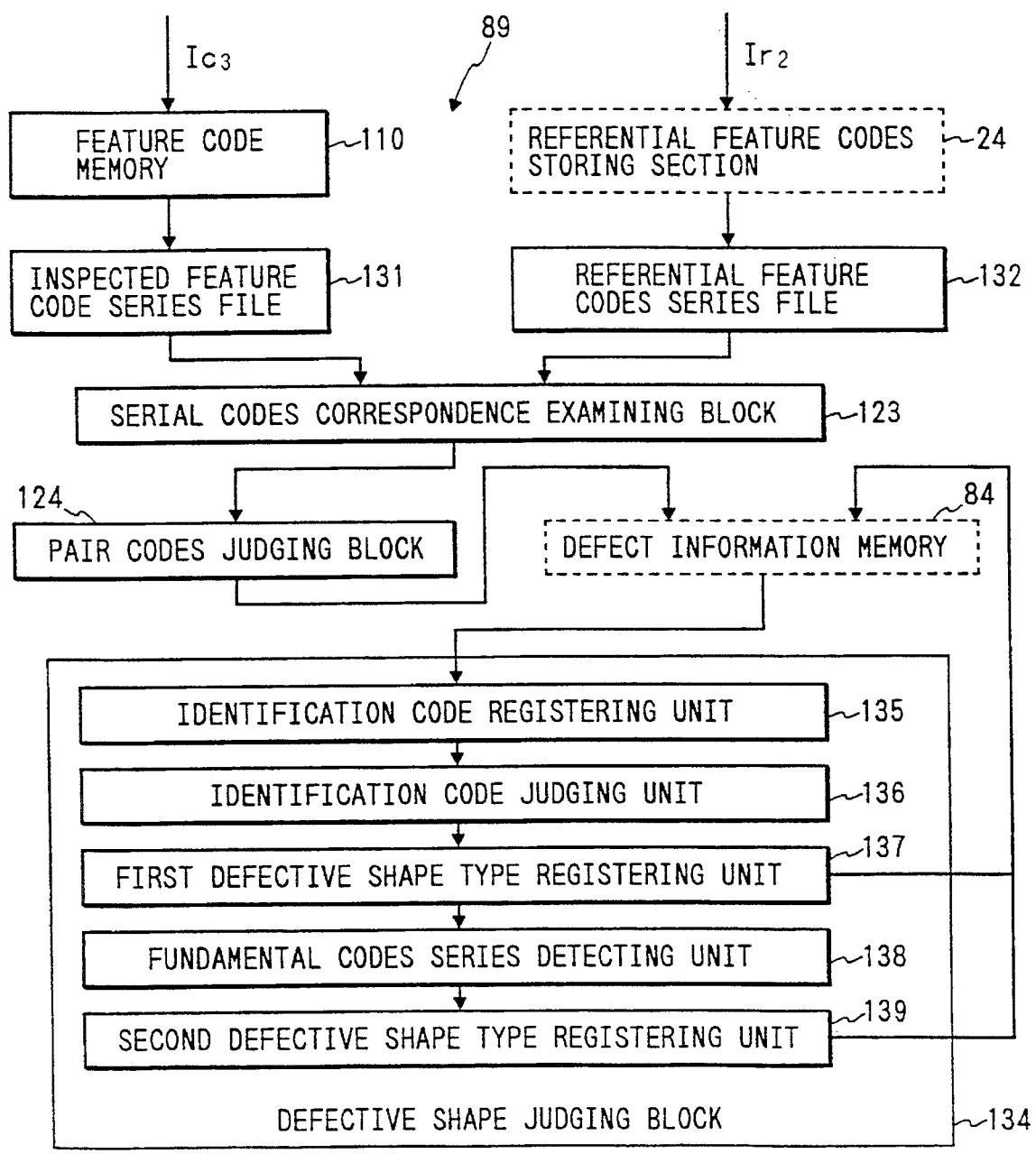
FIG. 34 is a constitutional block diagram of the CPU shown in FIG. 9 according to a modification of the fifth embodiment.

In the fifth embodiment, the serial codes comparing and judging block 133 is arranged in the CPU 89. However, as shown in FIG. 34, it is applicable that the serial codes correspondence examining block 123 and the specific pair codes judging block 124 be arranged in place of the serial codes comparing and judging block 133.

Next, a sixth embodiment of a wiring pattern detecting apparatus according to the present invention is described with reference to FIGS. 35 to 37.

In the sixth embodiment, comparing and judging operations performed in the second comparing and judging section 26 are described. In this case, a plurality of feature codes Ic3 which each are composed of the corner code Cf(j,DCj) of a feature point and positional coordinates of the feature point are produced in the specific shape detecting section 22 according to the second embodiment and are transferred to the second comparing and judging section 26. The configuration of the second comparing and judging section 26 according to the sixth embodiment is the same as that shown in FIG. 9A Therefore, comparing and judging operations differing from those in the first embodiment are described in the sixth embodiment. Also, a feature code Ic3 having a corner code "X,Y" is called a feature code $I_{XY}$, and a referential feature code Ir2 having a corner code "X,Y" is called a feature code $Ir_{XY}$ in the sixth embodiment.

Figure 35:
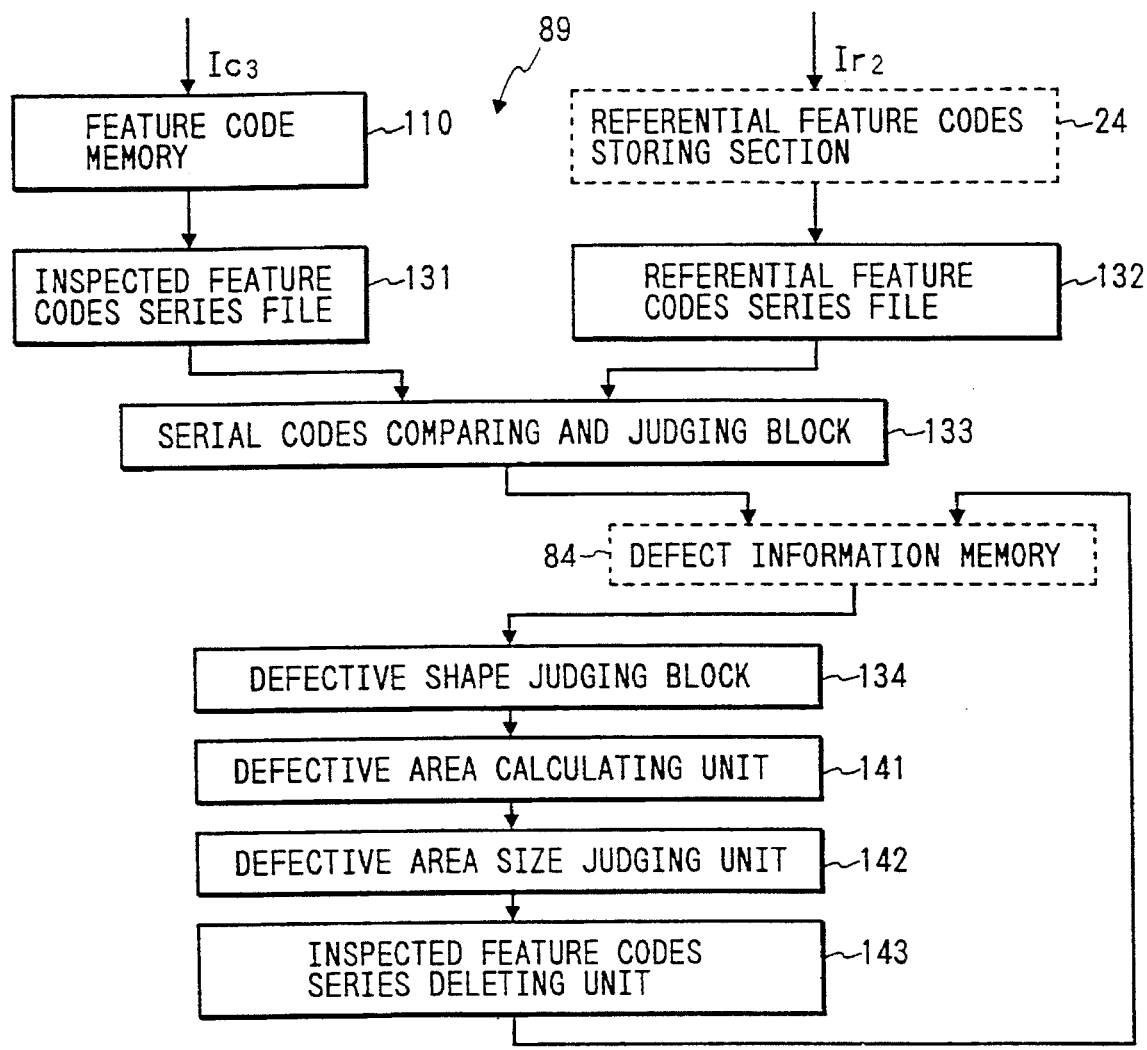
FIG. 35 is a constitutional block diagram of the CPU shown in FIG. 9 according to a sixth embodiment of the present invention.

FIG. 35 is a constitutional block diagram of the CPU 89 according to the sixth embodiment.

As shown in FIG. 35, the CPU 89 comprises the feature code memory 110, the inspected feature codes series file 131, the referential feature codes series file 132, the serial codes comparing and judging block 133, the defective shape judging block 134, a defective area calculating unit 141 for calculating a defective area of a disconnection or a protrusion which is registered in the first defective shape type registering unit 137 of the judging block 134 in connection with an inspected feature codes series, a defective area size judging unit 142 for judging whether or not a value of the defective area is higher than an allowable value, and an inspected feature codes series deleting unit 143 for deleting the inspected feature codes series pertaining to the disconnection or the protrusion from the defect information memory 84 in cases where it is judged in the defective area size judging unit 142 that the value of the defective area is not higher than the allowable value.

In the above configuration, even though a defective shape type of an inspected feature codes series not agreeing with a referential feature codes series is judged as a disconnection or a protrusion in the defective shape judging block 134, there is a case that the wiring pattern Pw indicated by the inspected feature codes series has no defect represented by the disconnection or the protrusion because the defective shape existing in the wiring pattern Pw is too small. In other words, a defect such as a disconnection or a protrusion shown in FIGS. 30B, 30D depends on a value of its defective area, and it is not required to report the defect to an operator in cases where a value of the defective area is lower than a prescribed value set by the operator in advance. Therefore, it is required to calculate the defective area of a disconnection or a protrusion. In the defective area calculating unit 141 an area of a rectangular region in which feature codes Ic3 pertaining to a disconnection or a protrusion are included is calculated as a defective area of a defective shape, and the disconnection or the protrusion is reported to an operator in cases where a value of the defective area is higher than an allowable value Va set by the operator in advance.

Figure 36:
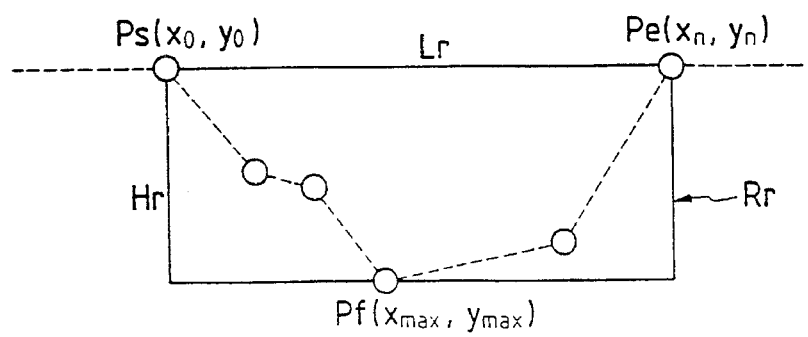
FIG. 36 shows an area of a rectangular region defined by three feature codes Ic3 pertaining to a lack.

FIG. 36 shows an area of a rectangular region defined by feature codes Ic3 pertaining to a disconnection.

As shown in FIG. 36, in cases where a feature code Ic3 representing a starting point Ps, a feature code Ic3 representing an ending point Pe and a feature code Ic3 representing a farthest point Pf placed in a deepest position of a disconnection are arranged, a length Lr of a rectangular region Rr defined by the points Ps, Pe and Pf is defined as a length of a straight line connecting the starting point Ps and the ending point Pe, and a height Hf of the rectangular region Rr is defined as a distance from the farthest point Pf to the straight line. The length Lr of the rectangular region Rr is calculated according to an equation (18).

$$Lr = \{(Xn-X_o)^2 + (Yn-Y_o)^2\}^{1/2} \quad (18)$$

Here coordinates of the starting point Ps are expressed by $(X_o, Y_o)$ and coordinates of the ending point Pe are expressed by $(Xn, Yn)$.

The height Hf of the rectangular region Rr is calculated according to an equation (19).

$$Hr = |Xmax(Yn-Y_o) - Ymax(Xn-X_o) + (Y_oXn - X_oYn)|/Lr \quad (19)$$

Here coordinates of the farthest point Pf are expressed by (Xmax, Ymax).

Therefore, a defective area Sd of the rectangular region Rr is calculated according to an equation (20).

$$Sd = |Xmax(Yn-Y_o) - Ymax(Xn-X_o) + (Y_oXn - X_oYn)| \quad (20)$$

In the same manner, an area of a rectangular region defined by feature codes Ic3 pertaining to a protrusion is calculated.

Figure 37:
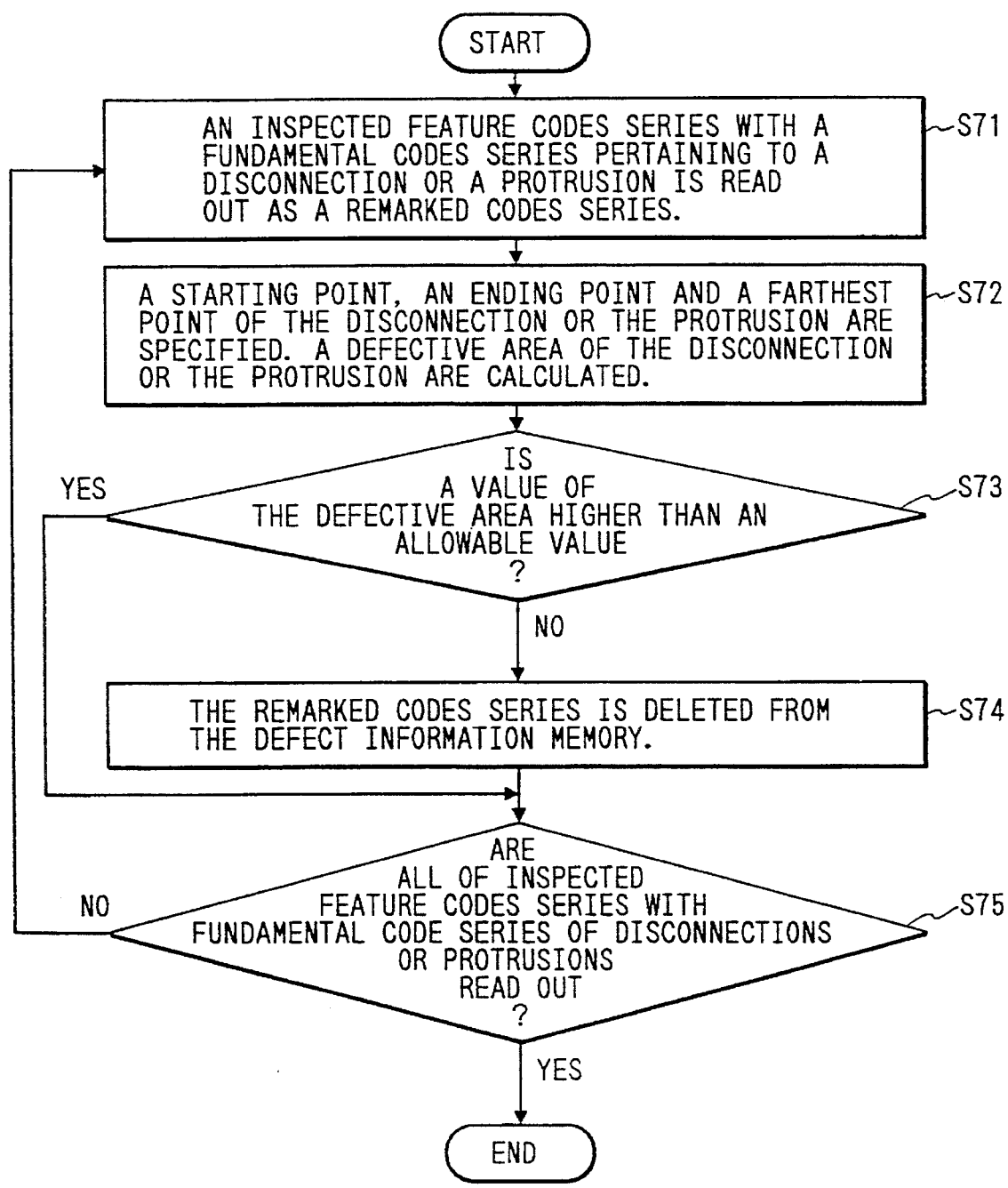
FIG. 37 is a flow chart showing a procedure for calculating a defect area Sd of the rectangular region shown in FIG. 36 and judging whether or not a defective shape indicated by an inspected feature codes series is registered in the defect information memory.

FIG. 37 is a flow chart showing a Procedure for calculating the defective area Sd of the rectangular region Rr and judging whether or not a defective shape indicated by an inspected feature codes series is registered in the defect information memory 84

As shown in FIG. 37, in a step S71 an inspected feature codes series in which a fundamental codes series pertaining to a defective shape type judged as a disconnection or a protrusion in the defective shape judging block 134 is included is read out from the defect information memory 84 to the defective area calculating unit 141. The inspected feature codes series is called a remarked codes series.

In a step S72, positional coordinates $(X_o, Y_o)$ of a feature code Ic3 representing a starting point Ps of the disconnection or the protrusion in the remarked codes series, positional coordinates (Xn,Yn) of a feature code Ic3 representing an ending point Pe of the disconnection or the protrusion in the remarked codes series and positional coordinates (Xmax, Ymax) of a feature code Ic3 representing a farthest point Pf of the disconnection or the protrusion in the remarked codes series are specified, and a defective area Sd of the disconnection or the protrusion is calculated according to the equations (18) to (20) in the calculating unit 141.

In a step S73, it is judged in the judging unit 142 whether or not a value of the defective area Sd is higher than an allowable value Va. In cases where the value of the defective area Sd is higher than the allowable value Va, the remarked codes series keeps being registered in the defect information memory 84. Therefore, the procedure proceeds to a step S75. In cases where the value of the defective area Sd is not higher than the allowable value Va, the procedure proceeds to a step S74.

In the step S74, the remarked codes series registered in the defect information memory 84 is deleted in the deleting unit 143 because it is not required to report the remarked codes series to an operator as a piece of defect information.

In the step S75, it is judged whether or not all of inspected feature codes series of which defective shape types are respectively judged as a disconnection or a protrusion in the defective shape judging block 134 are read out. In cases where all of the inspected feature codes series are not read out, the procedure returns to the step S71 to read out another inspected feature codes series of which a defective shape type is judged as a disconnection or a protrusion in the defective shape judging block 134. In contrast, in cases where all of the inspected feature codes series are read out, the procedure is ended.

Accordingly, because a piece of defect information pertaining to a disconnection or a protrusion is deleted in cases where a size of the disconnection or the protrusion is smaller than a prescribed value, disconnections and protrusions really required to be reported to an operator can be reported as pieces of defect information, and a fault judgement in which a small sized deformation similar to a disconnection or a protrusion is detected as a defective shape can be prevented.

In the sixth embodiment, a defective shape such as a disconnection or a protrusion is processed. However, because a pinhole or a residue is not required to be reported in cases where a size of the pinhole or the residue is small, it is applicable that a defective shape such as a pinhole or a residue be processed in the defective area calculating and judging block 141.

Next, a seventh embodiment of a wiring pattern detecting apparatus according to the present invention is described with reference to FIGS. 38 to 39.

In the seventh embodiment, comparing and judging operations performed in the second comparing and judging section 26 are described. In this case, a plurality of feature codes Ic3 which each are composed of the corner code Cf(j,DCj) of a feature point and positional coordinates of the feature point are produced in the specific shape detecting section 22 according to the second embodiment and are transferred to the second comparing and judging section 26.

The configuration of the second comparing and judging section 26 according to the seventh embodiment is the same as that shown in FIG. 9A. Therefore, comparing and judging operations differing from those in the first embodiment are described in the seventh embodiment. Also, a feature code Ic3 having a corner code "X,Y" is called a feature code $I_{XY}$, and a referential feature code Ir2 having a corner code "X,Y" is called a feature code $Ir_{XY}$ in the seventh embodiment.

FIG. 38 is a constitutional block diagram of the CPU 89 according to the seventh embodiment.

As shown in FIG. 38, the CPU 89 comprises the feature code memory 110, the inspected feature codes series file 121, the referential feature codes series file 122, the specific pair code judging block 124, a specific pair codes deleting block 151 for deleting the specific pair codes judged in the judging block 124 from the inspected feature codes series or the referential feature codes series, the serial codes comparing block 112, and the judging block 113.

In the above configuration, an operation performed in the specific pair codes deleting block 151 is described with reference to FIG. 39.

FIG. 39 shows an example of an inspected feature codes series in which paired codes I18 and I81 and paired codes I12 and I21 are included.

As shown in FIG. 39, paired codes I18 and I81 and paired codes I12 and I21 included in an inspected feature codes series Si are prepared in the inspected feature codes series file 121. Thereafter, it is judged in the specific pair codes judging block 124 that the paired codes I18 and I81 are not specific pair codes because the feature code I81 is placed outside a narrow allowable limit Aq1. In contrast, it is judged in the specific pair codes judging block 124 that the paired codes I12 and I21 are a pair codes series because the paired codes I21, I12 are placed within a narrow allowable limit Aq2. Thereafter, the paired codes I18 and I81 are not deleted in the specific pair codes deleting block 151, and the paired codes I12 and I21 are deleted in the specific pair codes deleting block 151 from the inspected feature codes series Si because the paired codes I12 and I21 are judged as a pair codes series. Thereafter, the inspected feature codes series Si not having the paired codes I12 and I21 is transferred to the serial codes comparing block 112 to compare the inspected feature codes series Si processed in the block 151 with a plurality of referential feature codes series registered in the referential feature codes series file 122. Thereafter, the inspected feature codes series Si is transferred to the defect information memory 84 because the paired codes I18 and I81 are still included in the inspected feature codes series Si.

Accordingly, even though a pair codes series occurring because a minute shape change of an edge not existing in a non-defective wiring pattern is actually generated in the wiring pattern Pw is included in an inspected feature codes series, the minute shape change is not reported to an operator because the minute shape change is not defective in the wiring pattern Fw. Therefore, false reports such as a minute shape change of the wiring pattern Pw can be reduced.

In the seventh embodiment, a pair codes series is deleted from an inspected feature codes series in the specific pair codes deleting block 151 after the inspected feature codes series including the pair codes series is formed in the inspected feature codes series file 121. However, it is applicable that an inspected feature codes series be formed without connecting any pair codes series in the inspected feature codes series file 121.

Next, an eighth embodiment of a wiring pattern detecting apparatus according to the present invention is described with reference to FIGS. 40 to 47.

Figure 40:
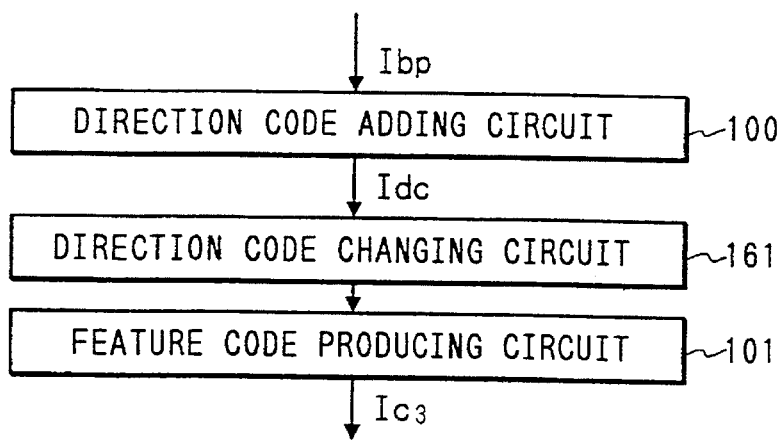
FIG. 40 is a constitutional block diagram of a specific shape detecting section shown in FIG. 1 according to an eighth embodiment of the present invention.

FIG. 40 is a constitutional block diagram of the specific shape detecting section 22 according to the eighth embodiment.

As shown in FIG. 40, the specific shape detecting section 22 comprises the direction code adding circuit 100 for adding one of eight types direction codes respectively indicating an edge direction of the wiring pattern Pw to each of contour pixels of the wiring pattern Pw in the processed bi-level image Ibp produced in the through hole filling section 15 to form a direction code image Idc, a direction code changing unit 161 for changing a direction code DC0 of a remarked pixel P0 to another direction code DCn added to two of neighboring pixels P1 to P8 adjacent to the remarked pixel P0 in the direction code adding circuit 100 to prevent the formation of an unstable feature code resulting from a quantization error which influences the remarked pixel P0 in cases where the directional codes DCn of two neighboring pixels are the same as each other and differ from the direction code DC0 of the remarked pixel P0, and the feature code producing circuit 101 for producing one or more corner codes from the direction codes which are added in the direction code adding circuit 100 or are changed in the direction code changing unit 161.

Pixels of the direction code image Idc formed in the adding circuit 100 are scanned with a 3×3 scanning window one after another in the direction code changing unit 161. A pixel placed in the center of the 3×3 scanning window is called a remarked pixel P0 having a direction code DC0, and eight neighboring pixels P1 to P8 surrounding the remarked pixel P0 are placed in the 3×3 scanning window. The neighboring pixels P1 to P8 have direction codes DC1 to DC8.

Figure 41:
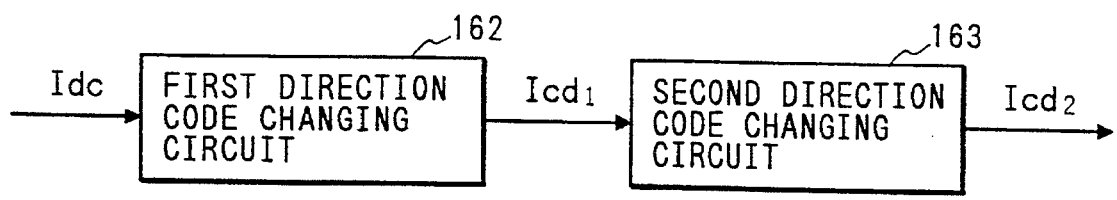
FIG. 41 is a constitutional block diagram of a direction code changing unit shown in FIG. 40 according to the eighth embodiment.

FIG. 41 is a constitutional block diagram of the direction code changing unit 161 according to the eighth embodiment.

As shown in FIG. 41, the direction code changing unit 161 comprises a first direction code changing circuit 162 for changing the direction code DC0 of the remarked pixel P0 in cases where the direction code DC0 is an odd number, and a second direction code changing circuit 163 for changing the direction code DC0 of the remarked pixel P0 in cases where the direction code DC0 is an even number.

Figure 42:
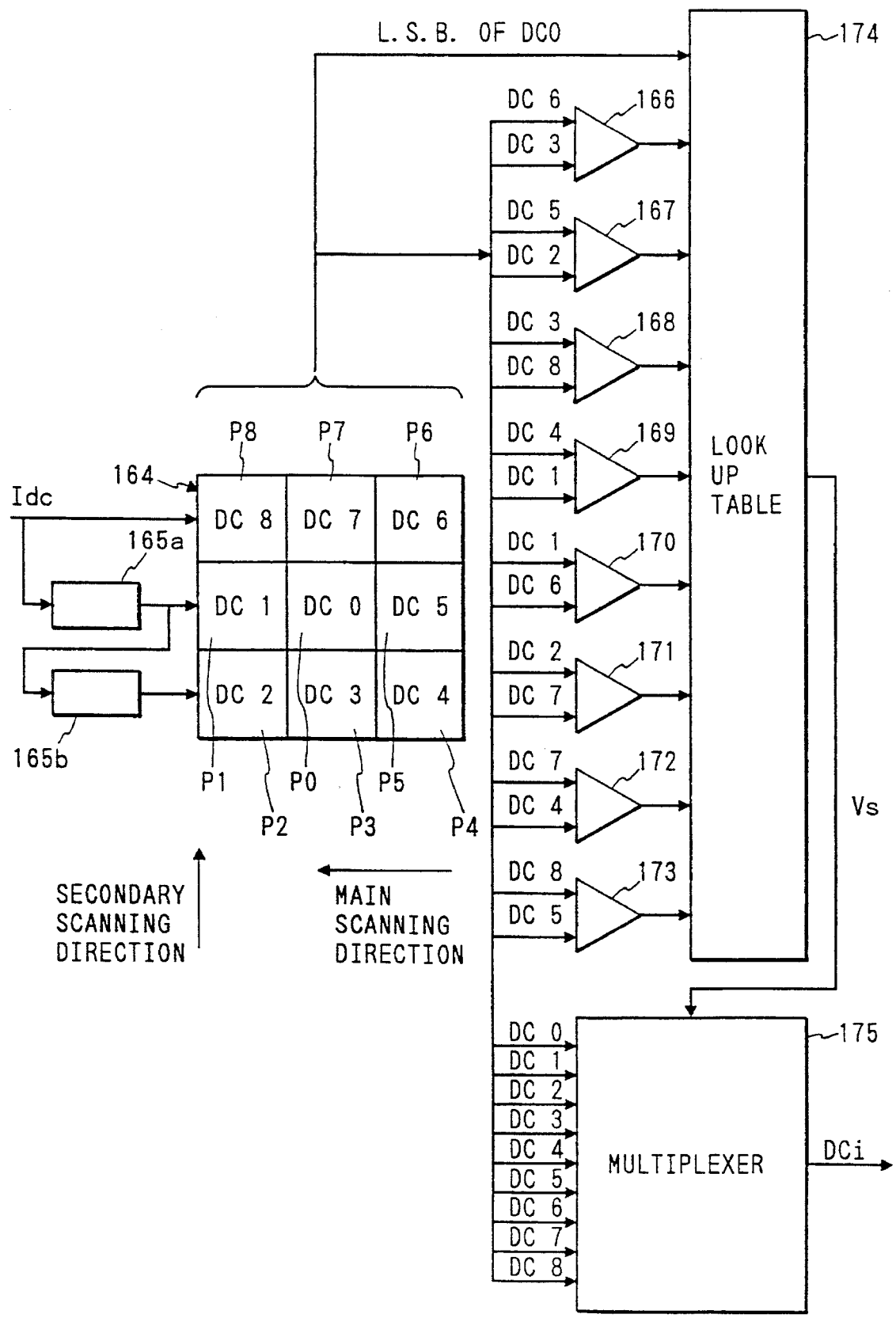
FIG. 42 is a constitutional block and circuit diagram of a first direction code changing circuit shown in FIG. 41 (or a second direction code changing circuit shown in FIG. 41)

FIG. 42 is a constitutional block and circuit diagram of the first direction code changing circuit 162 (or the second direction code changing circuit 163).

As shown in FIG. 42, the first direction code changing circuit 162 comprises a 3×3 scanning window circuit 164 for scanning nine (3×3) pixels P0 to P8 of the direction code image Idc with a 3×3 scanning window, a first line memory 165a for temporarily storing direction codes DC0,DC1 and DC5 of the pixels P0,P1 and P5, a second line memory 165b for temporarily storing direction codes DC2,DC3 and DC4 of the pixels P2,P3 and P4, a first comparator 166 for comparing the direction codes DC3, DC6 of the neighboring pixels P3, P6 and outputting a compared value "1" in cases where the direction codes DC3, DC6 are the same value, a second comparator 167 for comparing the direction codes DC2, DC5 of the neighboring pixels P2, P5 and outputting a compared value "1" 1 in cases where the direction codes DC2, DC5 are the same value, a third comparator 168 for comparing the direction codes DC3, DC8 of the neighboring pixels P3, P8 and outputting a compared value "1" in cases where the direction codes DC3, DC8 are the same value, a fourth comparator 169 for comparing the direction codes DC4, DC1 of the neighboring pixels P4, P1 and outputting a compared value "1" in cases where the direction codes DC4, DC1 are the same value, a fifth comparator 170 for comparing the direction codes DC1, DC6 of the neighboring pixels P1, P6 and outputting a compared value "1" in cases where the direction codes DC1, DC6 are the same value, a sixth comparator 171 for comparing the direction codes DC2, DC7 of the neighboring pixels P2, P7 and outputting a compared value "1" in cases where the direction codes DC2, DC7 are the same value, a seventh comparator 172 for comparing the direction codes DC7, DC4 of the neighboring pixels P7, P4 and outputting a compared value "1" in cases where the direction codes DC7, DC4 are the same value, an eighth comparator 173 for comparing the direction codes DC8, DC5 of the neighboring pixels P8, P5 and outputting a compared value "1" in cases where the direction codes DC8, DC5 are the same value, a look up table (LUT) 174 for receiving a least significant bit of the direction code DC0 and compared values of the comparators 166 to 173 and outputting a selecting value Vs, a multiplexer 175 for selecting one of the direction codes DC0 to DC8 of the pixel P0 to P8 transferred from the 3×3 scanning window circuit 164 according to the selecting value Vs transferred from the LUT 174 and changing the direction code DC0 of the remarked pixel P0 to the selected direction code.

In the above configuration, the pixels of the direction code image Idc produced in the direction code adding circuit 100 are scanned pixel by pixel with the 3×3 scanning window in the 3×3 scanning window circuit 164. In this case, the remarked pixel P0 and two neighboring pixels accord with three contour pixels of the wiring pattern Pw. Thereafter, the direction codes D1 to D8 of the neighboring pixels P1 to P8 are transferred to the comparators 166 to 173, and the direction codes D0 to D8 of the neighboring pixels P0 to P8 are transferred to the multiplexer 107.

Figures 43A, 43B, 43C, 43D:
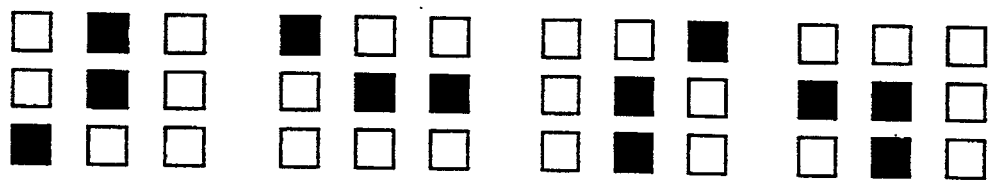
FIGS. 43A to 43H show eight arrangement patterns of three contour pixels of the wiring pattern scanned with a 3×3 scanning window.
Figures 43E, 43F, 43G, 43H:
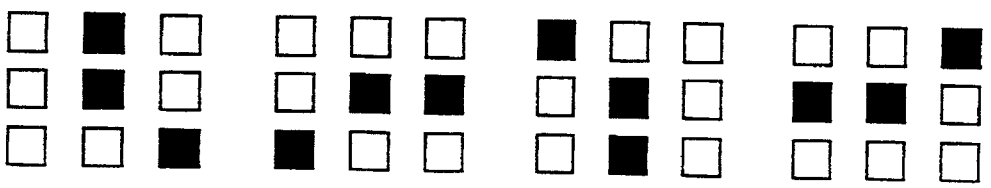

FIGS. 43A to 43H show eight arrangement patterns of three contour pixels of the wiring pattern Pw scanned with the 3×3 scanning window. In FIGS. 43A, 43H, block-colored pixels denote contour pixels composed of two neighboring pixels and the remarked pixel and have direction codes. White-colored pixels have non-direction codes "f", "0".

In cases where two neighboring pixels and the remarked pixel are placed to form one of eight arrangement patterns shown in FIG. 43 on condition that direction codes of the two neighboring pixels are the same value such as "1","2", "3", "4", "5", "6", "7" or "8", it is required to equalize the direction code DC0 of the remarked pixel P0 with the direction codes of the two neighboring pixels for the purpose of preventing the formation of an unstable feature code resulting from a quantization error which influences the remarked pixel P0.

Therefore, the direction codes DC3, DC6 of the neighboring pixels P3, P6 arranged to form the arrangement pattern shown in FIG. 43A are compared with each other in the first comparator 166, and a compared Value "1" is output from the first comparator 166 in cases where the direction codes DC3, DC6 of the neighboring pixels P3, P6 are the same value. Also, the direction codes DC2, DC5 of the neighboring pixels P2, P5 arranged to form the arrangement pattern shown in FIG. 43H are compared with each other in the second comparator 167, and a compared value "1" is output from the second comparator 167 in cases where the direction codes DC2, DC5 of the neighboring pixels P2, P5 are the same value. Also, the direction codes DC3, DC8 of the neighboring pixels P3, P8 arranged to form the arrangement pattern shown in FIG. 43E are compared with each other in the third comparator 168, and a compared value "1" is output from the third comparator 168 in cases where the direction codes DC3, DC8 of the neighboring pixels P3, P8 are the same value. Also the direction codes DC4, DC1 of the neighboring pixels P4, P1 arranged to form the arrangement pattern shown in FIG. 43B are compared with each other in the fourth comparator 169, and a compared value "1" is output from the fourth comparator 169 in cases where the direction codes DC4, DC1 of the neighboring pixels P4, P1 are the same value. Also, the direction codes DC1, DC6 of the neighboring pixels P1, P6 arranged to form the arrangement pattern shown in FIG. 43F are compared with each other in the fifth comparator 170, and a compared value "1" is output from the fifth comparator 170 in cases where the direction codes DC1, DC6 of the neighboring pixels P1, P6 are the same value. Also the direction codes DC2, DC7 of the neighboring pixels P2, P7 arranged to form the arrangement pattern shown in FIG. 43C are compared with each other in the sixth comparator 171, and a compared value "1" is output from the sixth comparator 171 in cases where the direction codes DC2, DC7 of the neighboring pixels P2, P7 are the same value. Also, the direction codes DC7, DC4 of the neighboring pixels P7, P4 arranged to form the arrangement pattern shown in FIG. 43G are compared with each other in the seventh comparator 172, and a compared value "1" is output from the seventh comparator 172 in cases where the direction codes DC7, DC4 of the neighboring pixels P7, P4 are the same value. Also, the direction codes DC8, DC5 of the neighboring pixels P8, P5 arranged to form the arrangement pattern shown in FIG. 43D are compared with each other in the eighth comparator 173, and a compared value "1" is output from the eighth comparator 173 in cases where the direction codes DC8, DC5 of the neighboring pixels P8, P5 are the same value. Therefore, a compared value "1" is output from one of the comparators 166 to 173, and a plurality of compared values "1" are not simultaneously output from a plurality of comparators. In contrast, in cases where direction codes of two neighboring pixels input to each of the comparators 166 to 173 are not the same value, a compared value "0" is output from each of the comparators 166 to 173.

Thereafter, the compared value "1" and/or the compared values "0" are input to the LUT 174. In the LUT 174, as shown in FIG. 44, a selecting value Vs having a value "0", "1", "2", "3", "4", "5", "6", "7" or "8" is selected and output to the multiplexer 175. In this case, the selecting value Vs is equal to a number i of a direction code DCi output to a comparator from which the compared value "1" is output in cases where a value of the direction code DC0 is an odd number. Therefore, the direction code DCi can be specified in the multiplexer 175 according to the selecting value Vs. Also, in cases where a value of the direction code DC0 is an even number or the compared value "1" is not output from any comparator, the selecting value Vs is equal to "0". Therefore, the direction code DC0 can be specified in the multiplexer 175 according to the selecting value Vs. The judgement whether a value of the direction code DC0 is an odd number or an even number is performed according to the least significant bit of the direction code DC0.

In the multiplexer 175, as shown in FIG. 44, a direction code DCi is selected from among the direction codes DC0 to DC8 according to the selecting value Vs having a value "i" and is output. Thereafter, the direction code DC0 of the remarked pixel P0 is changed to the direction code DCi. The change of the direction code DC0 to the direction code DCi is performed each time the pixels of the direction ode image Idc are scanned pixel by pixel with the 3×3 scanning window to produce a first-stage changed direction code image Icd1.

Therefore, because the direction code DC0 of the remarked pixel P0 is changed to the direction code Di of a neighboring pixel, direction codes of three contour pixels of the wiring pattern Pw scanned with the 3×3 scanning window can have the same value in cases where direction codes of a pair of neighboring pixels are the same value and the direction code DC0 is an odd number.

Thereafter, the first-stage changed direction code image Icd1 is transferred to the second direction code changing circuit 163. As shown in FIG. 42, the circuit 163 comprises the 3×3 scanning window circuit 164, the line memory 165a, 165b, the comparators 166, 173, a look up table (LUT) 176 functioning as shown in FIG. 45, and the multiplexer 175.

In the circuit 163, a selecting value Vs having a value "0", "1", "2", "3", "4", "5", "6", "7" or "8" is selected and output to the multiplexer 175 to produce a second-stage changed direction code image Icd2. In this case, the selecting value Vs is equal to a number i of a direction code DCi input to a comparator from which the compared value "1" is output in cases where a value of the direction cede DC0 is an even number. Also, in cases where a value of the direction code DC0 is an odd number or the compared value "1" is not output from any comparator, the selecting value Vs is equal to "0".

Therefore, because the direction code DC0 of the remarked pixel P0 is changed to the direction code DCi of a neighboring pixel, direction codes of three contour pixels of the wiring pattern Pw scanned with the 3×3 scanning window can have the same value in cases where direction codes of a pair of neighboring pixels are the same value and the direction code DC0 is an even number.

Accordingly, because the first and second direction code changing circuits 162, 163 are arranged in series, the formation of an unstable feature code resulting from a quantization error which influences the remarked pixel P0 can be prevented regardless of whether the direction code DC0 is an odd number or an even number.

A processing example performed in the direction code unit 161 is described with reference to FIGS. 46, 47.

Figure 46:
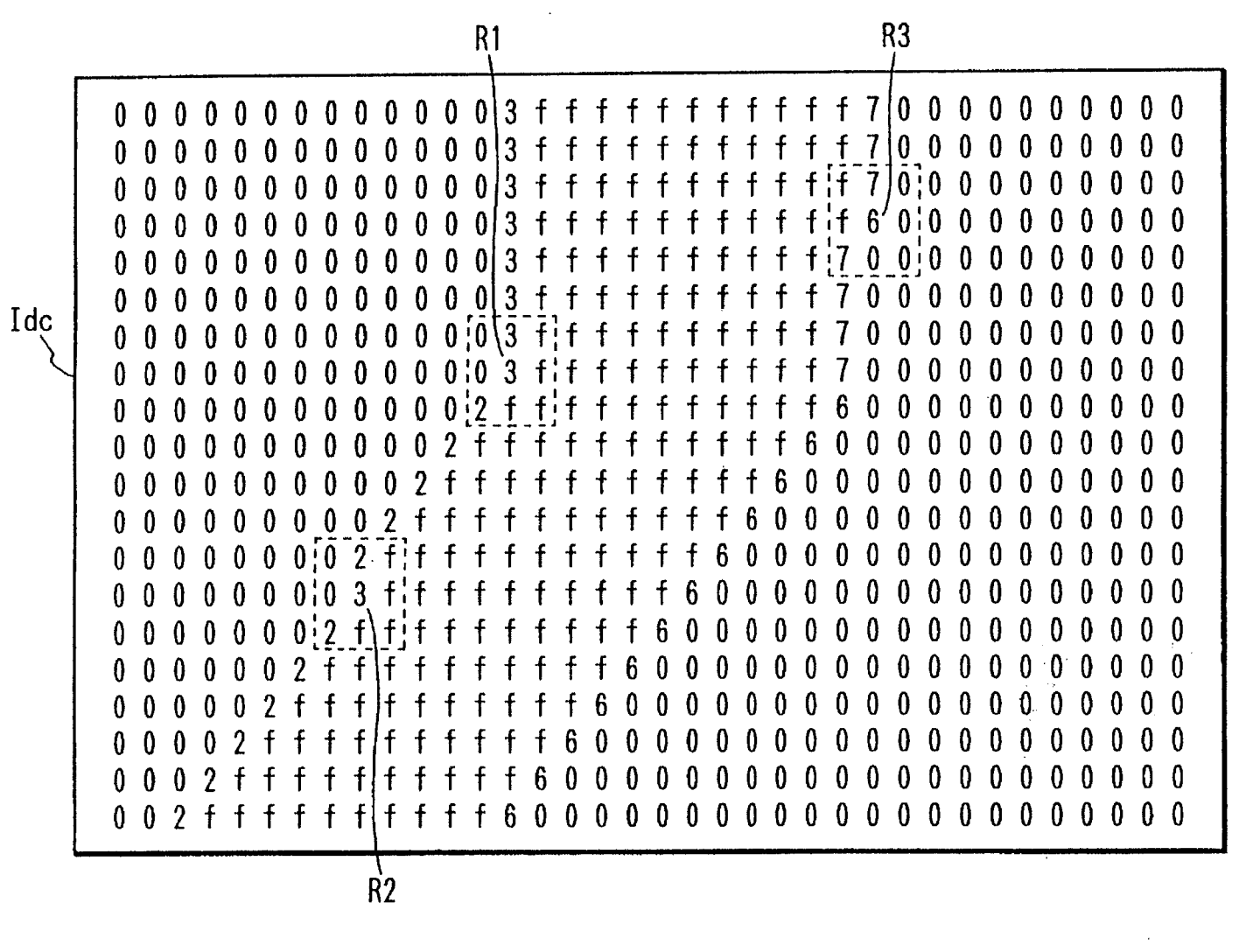

FIG. 46 shows an example of the direction code image Idc in which contour pixels of the wiring pattern Pw have direction codes.

In cases where a first region R1 shown in FIG. 46 is scanned with the 3×3 scanning window as shown in FIG. 47A, a direction code DC0 of the remarked pixel P0 has a value "3", a direction code DC3 of a first neighboring pixel P3 has a value "3", and a direction code DC6 of a second neighboring pixel P6 has a value "2". In this case, because the value of the direction code DC3 differs from that of the direction code DC6, as shown in FIG. 47D, the direction code DC0 of the remarked pixel P0 is not changed in the direction code unit 161. Also, in cases where a second region R2 shown in FIG. 46 is scanned with the 3×3 scanning window, as shown in FIG. 47B, a direction code DC0 of the remarked pixel P0 has a value "3", a direction code DC3 of a first neighboring pixel P3 has a value "2", and a direction code DC6 of a second neighboring pixel P6 has a value "2". In this case, because the direction codes DC3, DC6 have the same value, as shown in FIG. 47E, the direction code DC0="3" of the remarked pixel P0 is changed to "2" in the first direction code circuit 162 of the direction code unit 161. Also, in cases where a third region R3 shown in FIG. 46 is scanned with the 3×3 scanning window, as shown in FIG. 47C, a direction code DC0 of the remarked pixel P0 has a value "6", a direction code DC3 of a first neighboring pixel P3 has a value "7", and a direction code DC6 of a second neighboring pixel P6 has a value "7". In this case, because the direction codes DC3, DC6 have the same value, as shown in FIG. 47F, the direction code DC0="6" of the remarked pixel P0 is changed to "7" in the second direction code circuit 163 of the direction code unit 161.

Next, the reason that the direction code unit 161 comprises the first and second direction code changing circuits 162, 163 is described.

Assuming that contour pixels of the wiring pattern Pw having direction codes "2", "3", "2", "3", "2", "3", "2" and "3" in that order are processed in a single direction code changing circuit in which the direction code DC0 of the remarked pixel P0 is changed regardless of whether the direction code DC0 is an odd number or an even number, the direction codes of the contour pixels are changed to values "2", "2", "3", "2", "3", "2", "3" and "3". Therefore, in cases where a series of convexo-concave portions occurs at contour pixels of the wiring pattern Pw because of a series of quantization errors, the convexo-concave portions cannot be eliminated. In contrast, the contour pixels are processed in the direction code unit 161, the direction codes of the contour pixels are changed to values "2", "2", "2", "2", "2", "2", "2" and "3" in the first direction code changing circuit 162. Therefore the convexo-concave portions are eliminated, and an edge portion of the wiring pattern Pw can be smoothed.

Accordingly, because the direction codes of the contour pixels of the wiring pattern Pw are changed in the first and second direction code changing circuits 162, 163 of the direction code unit 161, a series of convexo-concave portions occurring at contour pixels of the wiring pattern Pw because of a series of quantization errors can be smoothed. Therefore, the inspection of the printed wiring board 13 can be stably performed.

Also, because a series of convexo-concave portions resulting from a series of quantization errors is smoothed, the number of feature codes Ic3 produced to indicate convexo-concave portions at edges of the wiring pattern Pw can be reduced, and pieces of fault defect information can be eliminated. Therefore, the inspection of the printed wiring board 13 can be performed at a high reliability.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. A wiring pattern inspection apparatus comprising:

direction code adding means for adding one of eight types direction codes to each of contour pixels placed in edges of a wiring pattern of a printed wiring board drawn in a processed bi-level image, each of the direction codes indicating a direction of an edge of the wiring pattern;

feature code extracting means for extracting a corner code from a pair of different types direction codes added to a pair of contour pixels adjacent to each other by the direction code adding means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes;

inspected serial codes registering means for registering a series of feature codes produced by serially connecting a plurality of feature codes output from the feature code extracting means, each of pairs of feature codes adjacent to each other being placed within an allowable distance and being placed nearest to each other;

referential serial codes registering means for serially connecting a plurality of referential feature codes stored in the referential feature code storing means to register a series of referential feature codes, each of pairs of referential feature codes adjacent to each other being placed within the allowable distance and being placed nearest to each other;

a serial codes comparing block for comparing the series of feature codes registered by the inspected serial codes registering means with the series of referential feature codes registered by the referential serial codes registering means; and a judging block for judging whether or not the corner codes and the positional coordinates of the series of feature codes agree with those of the series of referential feature codes according to a compared result obtained by the serial codes comparing block and reporting a piece of defect information in cases where the corner codes and the positional coordinates of the series of feature codes do not agree with those of the series of referential feature codes.

2. An apparatus according to claim 1 in which the serial codes comparing block comprises:

an average coordinates calculating unit for calculating average coordinates of the series of referential feature codes to set a referential allowable limit having its center placed at the average coordinates;

a searching unit for searching the serial codes producing circuit for a series of feature codes of which average coordinates are placed in the referential allowable limit set in the average coordinates calculating unit; and an examining unit for examining whether or not a series of corner codes of the series of feature code found out in the searching unit agrees with a series of referential corner codes of the series of referential feature codes to judge the wiring pattern defective in the judging block in cases where the series of corner codes does not agree with the series of referential corned codes.

3. An apparatus according to claim 1, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

4. An apparatus according to claim 3, further including:

design rule checking means for checking one or more feature types and those particular positions in the wiring pattern of the processed bi-level image formed by the through hole filling means as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

5. An apparatus according to claim 3, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

6. An apparatus according to claim 5, further including:

design rule checking means for checking one or more feature types and those particular positions in the wiring pattern of the processed bi-level image formed by the through hole filling means as pieces of feature information one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

7. A wiring pattern inspection apparatus comprising:

direction code adding means for adding one of eight types direction codes to each of contour pixels placed in edges of a wiring pattern of a printed wiring board drawn in a processed bi-level image, each of the direction codes indicating a direction of an edge of the wiring pattern;

feature code extracting leans for extracting a corner code from a pair of different types direction codes added to a pair of contour pixels adjacent to each other by the direction code adding means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes;

an inspected feature codes series file for registering an inspected feature codes series produced by serially connecting a plurality of feature codes output from the feature code extracting means, each of pairs of feature codes adjacent to each other being placed within an allowable distance and being placed nearest to each other;

a referential feature codes series file for registering a referential feature codes series produced by serially connecting a plurality of referential feature codes stored in the referential feature code storing means, each of pairs of referential feature codes adjacent to each other being placed within the allowable distance and being placed nearest to each other;

a serial codes correspondence examining block for examining correspondence of the feature codes in the inspected feature codes series registered in the inspected feature codes series file to the referential feature codes in the referential feature codes series registered in the referential feature codes series file to find paired feature codes not corresponding to any referential feature codes from the inspected feature codes series or to find paired referential feature codes not corresponding to any feature codes from the referential feature codes series;

a specific pair codes judging block for judging whether or not the paired feature codes or the paired referential feature codes found in the serial codes correspondence examining block are equivalent to specific pair codes, the specific pair codes being defined as paired codes placed in a narrow allowable limit; and a similarity judging block for judging that the inspected feature codes series registered in the inspected feature codes series file is similar to the referential feature codes series registered in the referential feature codes series file to regard the wiring pattern indicated by the inspected feature codes series non-defective in cases where it is judged in the specific pair codes judging block that the paired feature codes or the paired referential feature codes are equivalent to specific pair codes.

8. A wiring pattern inspection apparatus comprising:

direction code adding means for adding one of eight types direction codes to each of contour pixels placed in edges of a wiring pattern of a printed wiring board drawn in a processed bi-level image, each of the direction codes indicating a direction of an edge of the wiring pattern;

feature code extracting means for extracting a corner code from a pair of different types direction codes added to a pair of contour pixels adjacent to each other by the direction code adding means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes;

an inspected feature codes series file for registering an inspected feature codes series produced by serially connecting a plurality of feature codes output from the feature code extracting means, each of pairs of feature codes adjacent to each other being placed within an allowable distance and being placed nearest to each other;

a referential feature codes series file for registering a referential feature codes series produced by serially connecting a plurality of referential feature codes stored in the referential feature code storing means, each of pairs of referential feature codes adjacent to each other being placed within the allowable distance and being placed nearest to each other;

a specific pair codes judging block for judging whether or not paired feature codes of the inspected feature codes series existing in the inspected feature codes series file or paired referential feature codes of the referential feature codes series existing in the referential feature codes series file are equivalent to specific pair codes, the specific pair codes being defined as paired codes placed in a narrow allowable limit;

a specific pair code deleting block for deleting the specific pair codes judged in the specific pair codes judging block from the inspected feature codes series or the referential feature codes series;

a serial codes comparing block for comparing the inspected feature codes series produced in the specific pair code deleting block with the referential feature codes series produced in the specific pair code deleting block; and a judging block for judging whether or not the corner codes and the positional coordinates of the inspected feature codes series agree with those of the referential feature codes series according to a compared result obtained in the serial codes comparing block and reporting a piece of defect information in cases where the corner codes and the positional coordinates of the inspected feature codes do not agree with those of the referential feature codes series.

9. An apparatus according to claim 8, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

10. An apparatus according to claim 9, further including:

design rule checking means for checking one or more feature types and those particular positions in the wiring pattern of the processed bi-level image formed by the through hole filling means as pieces of feature information as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

11. A wiring pattern inspection apparatus comprising:

direction code adding means for adding one of eight types direction codes to each of contour pixels placed in edges of a wiring pattern of a printed wiring board drawn in a processed bi-level image, each of the direction code indicating a direction of an edge of the wiring pattern;

feature code extracting means for extracting a corner code from a pair of different types direction codes added to a pair of contour pixels adjacent to each other by the direction code adding means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes;

an inspected feature codes series file for registering an inspected feature codes series produced by serially connecting a plurality of feature codes output from the feature code extracting means, each of pairs of feature codes adjacent to each other being placed within an allowable distance and being placed nearest to each other;

a referential feature codes series file for registering a series of referential feature codes produced by serially connecting a plurality of referential feature codes stored in the referential feature code storing means, each of pairs of referential feature codes adjacent to each other being placed within the allowable distance and being placed nearest to each other;

a serial codes comparing and judging block for comparing the inspected feature code series registered in the inspected feature codes series file with the referential feature code series registered in the referential feature codes series file, and judging whether or not the inspected feature codes series agrees with the referential feature code series; and a defective shape judging block for inspecting whether or not one of a plurality of fundamental codes series indicating a plurality of defective shape types of the wiring pattern is included in the inspected feature codes series which is judged in the serial codes comparing and judging block not to agree with the referential feature code series, the wiring pattern indicated by the inspected feature codes series in which a fundamental codes series is included being judged to have a type of defective shape.

12. An apparatus according to claim 11 in which the defective shape types of the wiring pattern indicated by the fundamental codes series are a short, a disconnection, an open-end, a protrusion, a residue and a pinhole.

13. An apparatus according to claim 11, additionally including:

disconnection or protrusion detecting means for detecting a particular feature codes series with a fundamental codes series indicating a disconnection or a protrusion as a defective shape type from a plurality of inspected feature codes series with the fundamental codes series inspected in the defective shape judging block;

defect area calculating means for calculating a defect area of the disconnection or the protrusion indicated by the particular feature codes series detected in the disconnection or protrusion detecting means;

defect area size judging means for judging whether or not the defect area is larger than an allowable value; and codes series deleting means for deleting the particular feature codes series in cases where it is judged in the defect area size judging means that the defect area is not larger than the allowable value, the wiring pattern indicated by the particular feature codes series being regarded as nondefective.

14. An apparatus according to claim 11, further including:

image inputting means for producing a gray level image of the printed wiring board on which a holed wiring pattern including a pad seat and a through hole placed in the pad seat are formed; bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

15. An apparatus according to claim 14, further including:

design rule checking means for checking one or more feature types and those particular positions in the wiring pattern of the processed bi-level image formed by the through hole filling means as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information storied in the referential feature information storing means and judging one or more feature information pertaining to the defective feature types which differ from the referential feature information as one or more pieces of defect information.

16. A wiring pattern inspection apparatus comprising:

direction code adding means for adding one of eight types direction codes to each of contour pixels placed in edges of a wiring pattern or a printed wiring board drawn in a processed bi-level image, each of the direction codes indicating a direction of an edge of the wiring pattern;

feature code extracting means for extracting a corner code from a pair of different types direction codes added to a pair of contour pixels adjacent to each other by the direction code adding means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes;

an inspected feature codes series file for registering an inspected feature codes series produced by serially connecting a plurality of feature codes output from the feature code extracting means, each of pairs of feature codes adjacent to each other being placed within an allowable distance and being placed nearest to each other;

a referential feature codes series file for registering a series of referential feature codes produced by serially connecting a plurality of referential feature codes stored in the referential feature code storing means, each of pairs of referential feature codes adjacent to each other being placed within the allowable distance and being placed nearest to each other;

a serial codes correspondence examining block for examining correspondence of the feature codes in the inspected feature codes series registered in the inspected feature codes series file to the referential feature codes in the series of referential feature codes registered in the referential feature codes series file to find paired feature codes not corresponding to any referential feature codes from the inspected feature codes series or to find paired referential featurecodes not corresponding to any feature codes from the referential feature codes series;

a specific pair codes judging block for judging whether or not the paired feature codes or the paired referential feature codes found out in the serial codes correspondence examining block are equivalent to specific pair codes to judge whether or not the inspected feature codes series registered in the inspected feature codes series file is similar to the referential feature codes series registered in the referential feature codes series file, the specific pair codes being defined as paired codes placed in a narrow allowable limit, and the wiring pattern indicated by the inspected feature codes series which is judged to be similar to the referential feature codes series being regarded as non-defective; and a defective shape judging block for inspecting whether or not one of a plurality of fundamental codes series indicating a plurality of defective shape types of the wiring pattern is included in the inspected feature codes series which is judged in the specific pair codes judging block not to be similar to the referential feature codes series, the wiring pattern indicated by the inspected feature codes series in which a fundamental codes series is included being judged to have a type of defective shape.

17. An apparatus according to claim 16, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

18. An apparatus according to claim 17, further including:

design rule checking means for checking one or more feature types and those particular positions in the wiring pattern of the processed bi-level image formed by the through hole filling means as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

19. A wiring pattern inspection apparatus comprising:

direction code adding means for adding one of eight types direction codes to each of contour pixels placed in edges of a wiring pattern of a printed wiring board drawn in a processed bi-level image, each of the direction codes indicating a direction of an edge of the wiring pattern;

first direction code changing means for changing a direction code DCO of a remarked contour pixel added by the direction code adding means to another direction code DCn added to two neighboring contour pixels adjacent to the remarked contour pixel by the direction code adding circuit in cases where the direction codes DCn of the neighboring contour pixels are the same as each other and differ from the direction code DCO of the remarked contour pixel on condition that the direction code DCO is an odd number;

second direction code changing means for changing the direction code DCO of the remarked contour pixel passing through the first direction code changing means without any change of the direction code DCO to the direction code DCn on condition that the direction code DCO is an even number;

feature code extracting means for extracting a corner code from a pair of different types direction codes added to a pair of contour pixels adjacent to each other by the direction code adding means and changed by the first direction code changing means or the second direction code changing means to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes; and feature code comparing and judging means for comparing a plurality of feature codes sequentially output from the feature code extracting means with the referential feature codes stored in the referential feature code storing means and judging one or more feature codes pertaining to the defective shapes which differ from the referential feature codes as one or more defects.

20. An apparatus according to claim 19, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

21. An apparatus according to claim 20, further including:

design rule checking means for checking one or more feature types and those particular positions in the wiring pattern of the processed bi-level image formed by the through hole filling means as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

22. A wiring pattern inspection apparatus comprises:

direction code adding means for adding one of eight types direction codes to each of contour pixels placed in edges of a wiring pattern of a printed wiring board drawn in a processed bi-level image each of the direction codes indicating a direction of an edge of the wiring pattern, a direction code D0 being added to a remarked contour pixel, and eight direction codes DCi (i=1 to 8) being added to eight neighboring contour pixels Pi adjacent to the remarked contour pixel in that order;

a first comparator for comparing the direction codes DC3, DC6 of the neighboring contour pixels P3, P6 added by the direction code adding means with each other and outputting a compared value in cases where the direction codes DC3, DC6 are the same as each other;

a second comparator for comparing the direction codes DC2, DC5 of the neighboring contour pixels P2, P5 added by the direction code adding means with each other and outputting the compared value in cases where the direction codes DC2, DC5 are the same as each other;

a third comparator for comparing the direction codes DC3, DC8 of the neighboring contour pixels P3, P8 added by the direction code adding means with each other and outputting the compared value in cases where the direction codes DC3, DC8 are the same as each other;

a fourth comparator for comparing the direction codes DC1, DC4 of the neighboring contour pixels P1, P4 added by the direction code adding means with each other and outputting the compared value in cases where the direction codes DC1, DC 4 are the same as each other;

a fifth comparator for comparing the direction codes DC1, DC6 of the neighboring contour pixels P1, P6 added by the direction code adding means with each other and outputting the compared value in cases where the direction codes DC1, DC6 are the same as each other;

a sixth comparator for comparing the direction codes DC2, DC7 of the neighboring contour pixels P2, P7 added by the direction code adding means with each other and outputting the compared value in cases where the direction codes DC2, DC7 are the same as each other;

a seventh comparator for comparing the direction codes DC4, DC7 of the neighboring contour pixels P4, P7 added by the direction code adding means with each other and outputting the compared value in cases where the direction codes DC4, DC7 are the same as each other;

an eighth comparator for comparing the direction codes DC5, DC8 of the neighboring contour pixels P5, P8 added by the direction code adding means with each other and outputting the compared value in cases where the direction codes DC5, DC8 are the same as each other;

a look up table for outputting a selecting signal indicating one of the direction codes compared in one of the comparators from which the compared value is output;

a multiplexer for outputting a direction code Dn indicated by the selecting signal output from the look up table and changing the direction code DCO of the remarked contour pixel to the direction code DCn;

feature code extracting means for extracting a corner code from a pair of different types direction codes added to a pair of contour pixels adjacent to each other by the direction code adding means and changed by the multiplexer to indicate a corner of the wiring pattern existing in a feature point and outputting the corner code and positional coordinates of the feature point as a feature code;

referential feature code storing means for storing one or more referential corner codes and referential positional coordinates indicating one or more referential shapes and those referential positions in a non-defective printed wiring board of which a non-defective wiring pattern is formed according to a desired design as one or more referential feature codes; and feature code comparing and judging means for comparing a plurality of feature codes sequentially output from the feature code extracting means with the referential feature codes stored in the referential feature code storing means and judging one or more feature codes pertaining to the defective shapes which differ from the referential feature codes as one or more defects.

23. An apparatus according to claim 22, further including:

image inputting means for producing a gray level image of the printed wiring board on which a holed wiring pattern including a pad seat and a through hole placed in the pad seat are formed;

bi-level image producing means for converting the gray level image produced in the image inputting means into a bi-level image in which the holed wiring pattern including the pad seat is expressed by a group of black pixels and the through hole is expressed by a group of white pixels; and through hole filling means for virtually filling the through hole of the bi-level image produced in the bi-level image producing means by changing the group of white pixels expressing the through hole in the bi-level image to a group of black pixels to form a filled through hole and forming the processed bi-level image, in which the wiring pattern composed of the holed wiring pattern and the filled through hole is expressed by a group of black pixels, to add one direction code to each of the contour pixels placed in the edges of the wiring pattern of the processed bi-level image with the direction code adding means.

24. An apparatus according to claim 23, further including:

design rule checking means for checking one or more feature types and those particular positions in the wiring pattern of the processed bi-level image formed by the through hole filling means as pieces of feature information, one or more defective feature types which break one or more design rules of the wiring pattern or denote one or more open-ends or branches of the wiring pattern being included in the feature types;

referential feature information storing means for storing one or more referential feature types and those referential positions in a non-defective printed wiring board of which a non-defective wiring pattern is formed according to the design rules as pieces of referential feature information; and comparing and judging means for comparing the feature information detected in the design rule checking means with the referential feature information stored in the referential feature information storing means and judging one or more feature information pertaining to the defective feature types which differ from the referential feature information as one or more pieces of defect information.

\* \* \* \* \*